(12) United States Patent
Blaner et al.

(10) Patent No.: US 7,186,534 B1
(45) Date of Patent: Mar. 6, 2007

(54) POTENT INHIBITORS OF HUMAN 9-CIS RETINOL DEHYDROGENASE

(75) Inventors: William S. Blaner, New York, NY (US); Roseann Piantedosi Zott, River Edge, NJ (US); Mary V. Gamble, New York, NY (US); James R. Mertz, New York, NY (US)

(73) Assignee: The Trustees of Columbia University in the City of New York, New York, NY (US)

( * ) Notice: Subject to any disclaimer, the term of this patent is extended or adjusted under 35 U.S.C. 154(b) by 0 days.

(21) Appl. No.: 09/539,984

(22) Filed: Mar. 29, 2000

Related U.S. Application Data

(63) Continuation of application No. PCT/US98/20271, filed on Sep. 29, 1998, which is a continuation-in-part of application No. 08/940,424, filed on Sep. 29, 1997, now Pat. No. 6,171,837.

(51) Int. Cl.
*C12N 9/04* (2006.01)
*C12N 1/20* (2006.01)
*C12N 15/00* (2006.01)
*C12P 21/04* (2006.01)
*C12Q 1/32* (2006.01)
*C12Q 1/00* (2006.01)
*C07H 21/04* (2006.01)

(52) U.S. Cl. .............. 435/190; 435/4; 435/6; 435/252.3; 435/320.1; 435/69.1; 435/71.1; 435/440; 435/26; 536/23.2; 536/23.5

(58) Field of Classification Search ............... 435/189, 435/440, 6, 71.1, 252.3, 320.1, 190, 4, 69.7, 435/69.1; 536/23.1, 23.2, 24.1, 23.5
See application file for complete search history.

(56) References Cited

U.S. PATENT DOCUMENTS 5,731,195 A * 3/1998 Simon et al. ............ 435/252.3

FOREIGN PATENT DOCUMENTS

WO  WO 95/34580  * 12/1995

OTHER PUBLICATIONS

Sequence Search Result.*
Seidman. Curent Protocols in Molecular Biology (1994) 6.0.3-6.0.5.*
Sequence Alignment.*
Blaner, W. S. and Olson, J.A. (1994) The Retinoids, Biology, Chemistry, and Medicine (Sporn, M.B. et al., eds.), 229-255, Raven Press, New York.

Boerman, M.H. E. M. and Napoli, J. L. (1995) "Effects Of Sulfhydryl Reagents, Retinoids, and Solubilization On The Activity Of Microsomal Retinol Dehydrogenase," *Arch. Biochem Biophys.* 321:434-441.
Boerman, M. H. E. M. and Napoli, J. L. (1995) "Characterization Of A Microsomal Retinol Dehydrogenase: A Short-Chain Alcohol Dehydrogenase With Integral And Peripheral Membrane Forms That Interacts With Holo-CRBP (Type I)," Biochemistry 34:7027-7037.
Boleda, M. D. et al. (1993) "Physiological Substrates For Alcohol Dehydrogense Classes: Aldehydes Of Lipid Peroxidation ω-Hydroxyfatty Acids, And Retinoids," *Arch. Biochem. Biophys.* 307:85-90.
Chai, X. et al. (1995) "Cloning Of A cDNA For A Second Retinol Dehydrogenase Type II," *J. Biol. Chem.* 270:28408-28412.
Driessen, C. A. et al. (1995) "Cloning And Expression of a cDNA Encoding Bovine Retinal Pigment Epithelial 11-cis Retinol Dehydrogenase," *Invest. Ophthalmol. & Visual Sci.* 36, 1988-1996.
Duester, G. (1996) "Involvement Of Alcohol Dehydrogenase, Short-Chain Dehydrogenase/Reductase, Aldehyde Dehydrogenase, and Cytochrome P450 in the Control of Retinoid Signaling by Activation of Retinoic Acid Synthesis," *Biochemistry* 35:12221-12225.
El Akawi, Z. and Napoli, J. L. (1994) "Rat Liver Cytosolic Retinal Dehydrogenase: Comparison of 13-cis, 9-cis, and all-trans-Retinal as Substrates and Effects of Cellular Retinoid-Binding Proteins," *Biochemistry* 33:1938-1943.
Hebuterne, X. et al. (1995) "Intestinal Absorption and Metabolism of 9-cis-β-Carotene In Vivo: Biosynthesis Of 9-cis-retionoic Acid," *J. Lipid Res.* 36:1264-1273.
Labrecque, J. et al. (1993) "Purification and Partial Characterization of a Rat Kidney Aldehyde Dehydrogenase that Oxidizes Retinal to Retinoic Acid," *Biochem. Cell Biol.* 71: 85-89.
Labrecque, J. et al. (1995) "A Novel Isoenzyme of Aldehyde Dehydrogenase Specifically Involved in the Biosynthesis of 9-cis and 11-trans Retinoic Acid," *Biochem. J.* 305:681-684.
Mertz, et al. (1997) "Identification and Characterization of A Sterospecific Human Enzyme That Catalyzes 9-cis-Retinol Oxidation," *J. Biol. Chem.* 272 (18) :11744-11749.
Napoli, J. (1996) "Retinoic Acid Biosynthesis and Metabolism," *FASEB J.* 10:993-1001.
Romert et al. (1998) "The Identificationof a 9-cis retinol dehydrogenase in the mouse embryo reveals a pathway synthesis of 9-cis retinol c acid," Proceedings National Academy of Sciences USA. 95:4404-4409.
Simon, A. et al. (1995) "The Retinal Pigment Epithelial-specific 11-cis Retinol Dehydrogenase Belongs to the Family of Short Chain Alcohol Dehydrogenase," *J. Biol. Chem.* 270: 1107-1112.
Ang, H.L. et al. (1996) *J. Biol. Chem.* 271:9526-9534.
Chai, X. and Napoli, J.L. (1996) *Gene (Amst.)* 169:219-222.

* cited by examiner

*Primary Examiner*—P. Achutamurthy
*Assistant Examiner*—Yong D. Pak
(74) *Attorney, Agent, or Firm*—John P. White; Cooper & Dunham LLP

(57) ABSTRACT

The cDNA sequence of the human 9-cis-retinol dehydrogenase enzyme is disclosed.

13 Claims, 18 Drawing Sheets

FIG. 1A

```
GAGACTGGGAGCAGTCTCTTAAACAAAAGCAAAAGAATAAGCTTCGGGCCCTCTAGTACCTGCCAAGCTTT    70
CGCCACAGGAGGCTGCCACCTGTAGTCACTGGGCTCCAGCTATGGCTGCCTCTTCTGCTGGGTGCC          140
TTACTCTGGGCAGTGCTGTGTTGCTCAGGGACGGCAGANCCTGCCCGCCAGCAATGCCTTGTCTTCA         210
TCACCGGCTCTGACTCAGGGTTTGCCGCCCCTTCTGCACTGCAGCTCGACCAGAAAAGCTTCCGANTCCT      280
GGCCAGCTGCCTGACCCCTCCGGGGCCGAGGACCTGCAGGGGTGCCTTCTTCCGGCTTCAACACCACC        350
NTCTTGGATATCACTGATCCCCAGAGCTTCCAGCAGGCAGCCAAGTGGTCGAGATGCACGTTAAGGAAG       420
CAGGGCCTTTTGCTCTGCTGAATAATGCTGGTGTGCTATCATCGGACCACACCATGGCTGACCCG           490
GCACGATTCCAGCGGGTGCTGAATGCAACACAATGGGTCCATCGGGGTCACCCTTGCCCTGCTGCCT         560
CTGCTCAGCAAGCCCGGGTGATCAACATCACCAGCTCCTGGGCTCGCCTGCGCAGCCAATGGTG            630
GGGGCTACTGTCTCCAAATTTGCCCTGAGCCTTCTCTGACACCCTGAGGCGGATGTAGCTCATTT           700
TGGGATACGGAGTCCATNGTGACCGCCTGGTTTNTTCCGAACCGCTGTGACCAACTTGGAGAGTNTGGAG      770
AAAACCCTGCAGGCCCTGCTGGGACACCGGCTGCCTCCTCCTGCCACACAGGCCCACTATGGGGGCCTTCCTCA  840
CCAAGTACCTCAAAATGCAACAGCGCCATCATGAACCTCTGCACCCGGACCTAACCAAGGTGAGCCG         910
ATGCCTGAGCATGCCCTGACTGCTCGACACCCCGAGCCCTGACGCCCAGGTTGGGATGCCAAGCTG          980
CTCTGGCTGCCTGCCTCCTCCTACCTGCCGCCAGCCTGCTGATGCTGTGCTCACCTGGGTCCTTCCCAAGC    1050
CTGCCCAAGCAGTCTACTGAATCCAGCCTTCCAGCAAGAGATTGTTTTCAAGGACAAGGACTTTGATTT      1120
ATTTCTGCCCCACCCTGCTACTGCCTGTGCCTGCCACAAAATAAGCACTAACAAAAGTCTATTGTTTA       1190
AAAAATAAAAGAAGGTGGCAGAAATGCCCAGTGGAA 1230
```

FIG. 1B

```
              10         20         30         40         50         60         70
L1 - MWLPLLLGVLLNAALWLLRDRQCLPA-SDAEFIFITGCDSGFGRLLALRLDQRGFRVLASCLTPSGAEDLQ      69
L2 - MWLYLLALVGLWNLLRLFRERKVVSHLQDKYVFITGCDSGFGNLLARQLDRRGMRVLAACLTEKGAEQLR      70
l1 - MWLYLLALVGLWNLLRFLRERKVVSHLQDKYVFITGCDSGFGNLLARQLDRRGMRVLAACLTEKGAEQLR      70
9c - MWLPLLGALLLWAVLWLLRDRQXLPA-SNAFVFIIGCDSGFGRLLALQLDQKSFRXLASCLIPSGAEDLQ      69

80         90        100        110        120        130        140
L1 - RVASSRLHTTLLDVTDPQSIRQAVKWVETHVGEAGLFGLVNNAGIIGPTPWQTREDFQRVLNVNTLG        139
L2 - SKTSDRLETVILDVTKTESIVAATQWVKERVGNTGLWGLVNNAGISGHLGPNEWHNKQNIASVLDVNLLG     140
l1 - SKTSDRLETVILDVTKTESIVAATQWVKERVGNRGLWGLVNNAGISVPVGPNEWMRKKDFASVLDVNLLG     140
9c - GVASSGFNTTXLDITDPQSFQQAAKWVEMHVKEAGLFGLVNNAGVAGIIGPTPWLTRDDFQRVLNVNTMG     139

150        160        170        180        190        200        210
L1 - PIGVTLALLPLLQARGRVINITSVLGRLAANGGGYCVSKEGLEAFSDSLRRDVAPFGVRVSIVEPGFFR      209
L2 - MIEVTLSTVPLVRKARCRVVNVASIAGRLSFCGGGYCISKYGVGGYCISKYGVGEAFSDSLRRELSYFGVKVAIVEPGFFR  210
l1 - VIEVTLNMLPLVREVTLNMLPLVRKARGRVVNIASTMGRMSLVGGGYCISKYGVGGYCISKYGVEAFSDSLRRELTYFGVKVAIIEPGGFK 210
9c - PIGVTLALLPLLQQARGRVINITSVLGRLAANGGGYCVSKFGLEAFSDSLRRDVAHFGIRESXVEPGXFR     209

220        230        240        250        260        270        280
L1 - TPVTNLETLEDTLQACWARLPPATQALYGEAFLTKYLRVQQRIMNMICDPDLAKVSRCLEHALTARHPRT     279
L2 - TDVTNGVTLSSNFQMLWDQTSSEVREVYGENYLASYLKMLNGLDQR-CNKDLSLVTDCMEHALTSCHPRT     279
l1 - TNVTNMERLSDNLKKLWDQTTEEVKEIYGEKFQDSYMKAMESLVNT-CSGDLSLVTDCMEHALTSCHPRT     279
9c - TPVTNLESXEKTLQACWARLPPATQAHYGGAFLTKYLKMQQRIMNLICDPDLTKVSRCLEHALTARHPRI     279

290        300        310        320
L1 - RYSPGWDAKLLWLPASYLPARLVDAVLAWVLPKPAQTV-Y      318
L2 - RYSAGWDAKFFYLPMSYLPTFLVDALFYHTSPKPEKAL        317
l1 - RYSPGWDAKFFYLPMSYLPTFLSDAVIHWGSVKPARAL        317
9c - RYSPGWDAKLLWLPASYLPASLVDAVLTWVLPKPAQAVY.      319
```

FIG. 4A

```
                        XX-TXXXACXGGGCTCGGA--GCCXXXAGXAXCXGCX-CXXGTXTGCTXX
                                10            20            30          40         50
NMKT7.SEQ               T------- ----GGCTCNGA---G----- -----------------GCCAA    15
NMLRDH.SEQ              CT-TGGTACCGAGCTCGGA--NCCACTAGTAACGGCCGCCAGTGTGCTGG       47
PCRD4.SEQ               GAGTCACACAGGGATAGGTCTGCCCACACAGGACCAGCT-CAGGTTTATTTC     49

XATTCGGXACXAXG---CTTXXCCATAXXXXGT------XTXXG-----A
                                60            70           80          90        100
NMKT7.SEQ    Kid        GANTCGG----------------ACCATG--------------------------   29
NMLRDH.SEQ   Liv        AATTCGGCACGAGG--CTTAGCTGTAGT--------GTGGG----A           83
PCRD4.SEQ    Tes        -ATTAGCTACAAAGTGCTTGCCCATAATCTGTTTCACACAATAAGCCATA       98

GCXTGXXAAXXCT------AXGXXXAXAGTCTC--XXXXAGCAGAC-AGAAA
                                110           120          130         140        150
NMKT7.SEQ               -------------------------------AGCAGAC-AGAAA            40
NMLRDH.SEQ              GCCTGGGAAGTCT-----AGGAGCAAAGTCTC--TCAAGCAGAC-AGAAA      125
PCRD4.SEQ               GCCTTGCCAATCCTCTGCCAAGCATAGTCTCATCTGCTCAGACCAGACA       148

GCTACAGCTT--CACACATT--GTGTT----GCC
                                160           170          180         190        200
NMKT7.SEQ               GCTACAGCTT--CACACATT--GTGTT----GCC----------T            67
NMLRDH.SEQ              GCTACAGCTT--CACACATT--GTGTT----GCC----------T            152
PCRD4.SEQ               TTTCCAGCTAAGTGTTAGGGGCCAAGGCTAAAGGGCTAGAGGAAAT           198
```

FIG. 4B

```
             200                 220                 240
             |                   |                   |
NMKT7.SEQ    GCCAGCTTTCCCCAG--AGCCTAGG--AGCCTAGGCTGCCCTCAGCAGGGCATCTCATCC  115
NMLRDH.SEQ   GCCAGCTTTCCCCAG--AG----AG---GCTGCCCTCAGCAGGGCATCTCATCC        195
PCRD4.SEQ    GACAAGTTTTCCTGCCCAGCCTAAGCCTGCCCTCAGCAGGGCATCTCATCC           248

260                 280                 300
             |                   |                   |
NMKT7.SEQ    CATCATGTGGCTGCTGCCTCTGCCTTCTGCCTTGCTGGGTGCTGCCTTGCTGGGCAGTGCTGT  165
NMLRDH.SEQ   CATCATGTGGCTGCTGCCTCTGCCTTCTGCCTTGCTGGGTGCTGCCTTGCTGGGCAGTGCTGT  245
PCRD4.SEQ    CATCATGTGGCTGCTGCCTCTGCCTTCTGCCTTGCTGGGTGCTGCCTTGCTGGGCAGTGCTGT  298

320                 340
             |                   |
NMKT7.SEQ    GGTTGCTCAGAGACCGGCAGAGCCTGCCGGCCAGTGCCAGTGATGCTTTCATCTTC  215
NMLRDH.SEQ   GGTTGCTCAGAGACCGGCAGAGCCTGCCGGCCAGTGCCAGTGATGCTTTCATCTTC  295
PCRD4.SEQ    GGTTGCTCAGAGACCGGCAGAGCCTGCCGGCCAGTGCCAGTGATGCTTTCATCTTC  348

360                 380                 400
             |                   |                   |
NMKT7.SEQ    ATCACTGGCTGTGTGACTCTCTGGCTTTGGGCGCCTTCTCTGGCACTGCAACTTGA  265
NMLRDH.SEQ   ATCACTGGCTGTGTGACTCTCTGGCTTTGGGCGCCTTCTCTGGCACTGCAACTTGA  345
PCRD4.SEQ    ATCACTGGCTGTGTGACTCTCTGGCTTTGGGCGCCTTCTCTGGCACTGCAACTTGA  398
```

FIG. 4C

```
              400                410          420          430          440          450
NMKT7.SEQ     CCAGAAGGGCTTCCAAGTCCTGGCCGGCCTGGCCCGGCCTGCTGACCCCCTCTGGAGCAG  315
NMLRDH.SEQ    CCAGAAGGGCTTCCAAGTCCTGGCCGGCCTGGCCCGGCCTGCTGACCCCCTCTGGAGCAG  395
PCRD4.SEQ     CCAGAAGGGCTTCCAAGTCCTGGCCGGCCTGGCCCGGCCTGCTGACCCCCTCTGGAGCAG  448

460          470          480          490          500
NMKT7.SEQ     AAGACCTGCAGCAGAGATGGCCCTCCTCCCGCCCTCCACACAACACCACTACTGGAT     365
NMLRDH.SEQ    AAGACCTGCAGCAGAGATGGCCCTCCTCCCGCCCTCCACACAACACCACTACTGGAT     445
PCRD4.SEQ     AAGACCTGCAGCAGAGATGGCCCTCCTCCCGCCCTCCACACAACACCACTACTGGAT     498

510          520          530          540          550
NMKT7.SEQ     ATCACTGATCCCCAGAATGTCCAGCAAGTTGCCAAGTGGGTGAAGACACG            415
NMLRDH.SEQ    ATCACTGATCCCCAGAATGTCCAGCAAGTTGCCAAGTGGGTGAAGACACG            495
PCRD4.SEQ     ATCACTGATCCCCAGAATGTCCAGCAAGTTGCCAAGTGGGTGAAGACACG            548

560          570          580          590          600
NMKT7.SEQ     TGTTGGAGAAACTGGACTTTTTGGTCTGGTGAATAACGCTGGCGTAGCTG           461
NMLRDH.SEQ    TGTTGGAGAAACTGGACTTTTTGGTCTGGTGAATAACGCTGGCGTAGCTG           545
PCRD4.SEQ     TGTTGGAGAAACTGGACTTTTTGGTCTGGTGAATAACGCTGGCGTAGCTG           598
```

FIG. 4D

```
                        GTATCATCGGGGCCCCACACCATGGCTAACACAGGATGATTTCCAGAGAGTA        461
                             610       620       630       640       650
NMKT7.SEQ      GTATCATCGGGGCCCCACACCATGGCTAACACAGGATGATTTCCAGAGAGTA        595
NMLRDH.SEQ     GTATCATCGGGGCCCCACACCATGGCTAACACAGGATGATTTCCAGAGAGTA        648
PCRD4.SEQ

CTGAGTGTGAACACACTGGGGCCCCATCGGTGTCACCCCTTGCCCCTGCTGCC        461
                             660       670       680       690       700
NMKT7.SEQ      CTGAGTGTGAACACACTGGGGCCCCATCGGTGTCACCCCTTGCCCCTGCTGCC        645
NMLRDH.SEQ     CTGAGTGTGAACACACTGGGGCCCCATCGGTGTCACCCCTTGCCCCTGCTGCC        698
PCRD4.SEQ

CCTGCTACAGCAGGCCAGGGGGTCGGGTGGTCAAACATCACCAGTGTCTTGG        461
                             710       720       730       740       750
NMKT7.SEQ      CCTGCTACAGCAGGCCAGGGGGTCGGGTGGTCAAACATCACCAGTGTCTTGG        695
NMLRDH.SEQ     CCTGCTACAGCAGGCCAGGGGGTCGGGTGGTCAAACATCACCAGTGTCTTGG        748
PCRD4.SEQ

GCCGCATAGCAGCCCAATGGCGGGGGGCTACTGTGTCTCCAAGTTTGGCCTG        461
                             760       770       780       790       800
NMKT7.SEQ      GCCGCATAGCAGCCCAATGGCGGGGGGCTACTGTGTCTCCAAGTTTGGCCTG        745
NMLRDH.SEQ     GCCGCATAGCAGCCCAATGGCGGGGGGCTACTGTGTCTCCAAGTTTGGCCTG        798
PCRD4.SEQ
```

FIG. 4E

```
NMKT7.SEQ                                                                                    461
NMLRDH.SEQ   GAGGCCTTCTCTGACAGCCTGAGGCGGGGACATGGCTCCGTTCGGAGTACA   795
PCRD4.SEQ    GAGGCCTTCTCTGACAGCCTGAGGCGGGGACATGGCTCCGTTCGGAGTACA   848
                      810        820        830        840        850

NMKT7.SEQ                                                                                    461
NMLRDH.SEQ   AGTCTCCATTGTGGAGCCTGGCTTCTTTCGAACCCCTGTGACCAACCTGG    845
PCRD4.SEQ    AGTCTCCATTGTGGAGCCTGGCTTCTTTCGAACCCCTGTGACCAACCTGG    898
                      860        870        880        890        900

NMKT7.SEQ                                                                                    461
NMLRDH.SEQ   AGAGTCTGGAGAGCACCCCTGAAGGCTTGTTGGGCCCGGCTACCTCCAGCT   895
PCRD4.SEQ    AGAGTCTGGAGAGCACCCCTGAAGGCTTGTTGGGCCCGGCTACCTCCAGCT   948
                      910        920        930        940        950

NMKT7.SEQ                                                                                    461
NMLRDH.SEQ   ATACAGGCCCACTACGGGGAAGCCTTCCTCGATACTTATCTTCGAGTACA   945
PCRD4.SEQ    ATACAGGCCCACTACGGGGAAGCCTTCCTCGATACTTATCTTCGAGTACA   998
                      960        970        980        990       1000
```

FIG. 4F

```
NMKT7.SEQ                                                                                              461
NMLRDH.SEQ  GCGCCGCATCATGAACCTGATCTGTGACCCAGAACTAACGAAGGTGACCA                                         995
PCRD4.SEQ   GCGCCGCATCATGAACCTGATCTGTGACCCAGAACTAACGAAGGTGACCA                                        1048
                     1010         1020        1030         1040       1050

NMKT7.SEQ                                                                                              461
NMLRDH.SEQ  GCTGCCTGGAGCATGCCCXTGACTGCTCGCCACCCCCGAACACGCTACAGC                                       1045
PCRD4.SEQ   GCTGCCTGGAGCATGCCCCTGACTGCTCGCCACCCCCGAACACGTTACAGC                                       1098
                     1060         1070        1080         1090       1100

NMKT7.SEQ                                                                                              461
NMLRDH.SEQ  CCAGGCTGGGATGCCAAGCTGCTCTGGCTCTGCCTCCTACCTTCCAGC                                         1095
PCRD4.SEQ   CCAGGCTGGGATGCCAAGCTGCTCTGGCTCTGCCTCCTACCTTCCAGC                                         1148
                     1110         1120        1130         1140       1150

NMKT7.SEQ                                                                                              461
NMLRDH.SEQ  CAGGGTGGTGGATGCTGTGCTCACXTGGATCCTTCCCCGGCCCCGCCCAGT                                       1145
PCRD4.SEQ   CAGGGTGGTGGATGCTGTGCTCACATGGATCCTTCCCCGGCCCCGCCCAGT                                       1198
                     1160         1170        1180         1190       1200
```

FIG. 4G

```
                CAGTCTCCTGATTCCAGCTTTACAGCAAGAXGCTGATTTTGAAAAGCAAG
                         1210      1220      1230      1240      1250
NMKT7.SEQ                                                               461
NMLRDH.SEQ      CAGTCTCCTGATTCCAGCTTTACAGCAAGAAGCTGATTTTGAAAAGCAAG      1195
PCRD4.SEQ       CAGTCTCCTGATTCCAGCTTTACAGCAAGAAGCTGATTTTGAAAAGCAAG      1248

GCATCTATTTCTGTGTCTACCCCAGTGCCTGGTTTCTGATACCAATTA
                         1260      1270      1280      1290      1300
NMKT7.SEQ                                                               461
NMLRDH.SEQ      GCATCTATTTCTGTGTCTACCCCAGTGCCTGGTTTCTGATACCAATTA        1245
PCRD4.SEQ       GCATCTATTTCTGTGTCTACCCCAGTGCTGGTTTCTGATACCAATTA         1298

XGCTCTCAATAAATATXTXTXGCTTTXAATCAAAXX
                         1310      1320      1330
NMKT7.SEQ                                                               461
NMLRDH.SEQ      NGCTCTCAATAAATATNTNT-GCTTTNAATCAAA                      1278
PCRD4.SEQ       GGCTCTCAATAAATATATGTATTGCTTTAAATCAAAAA                  1334
```

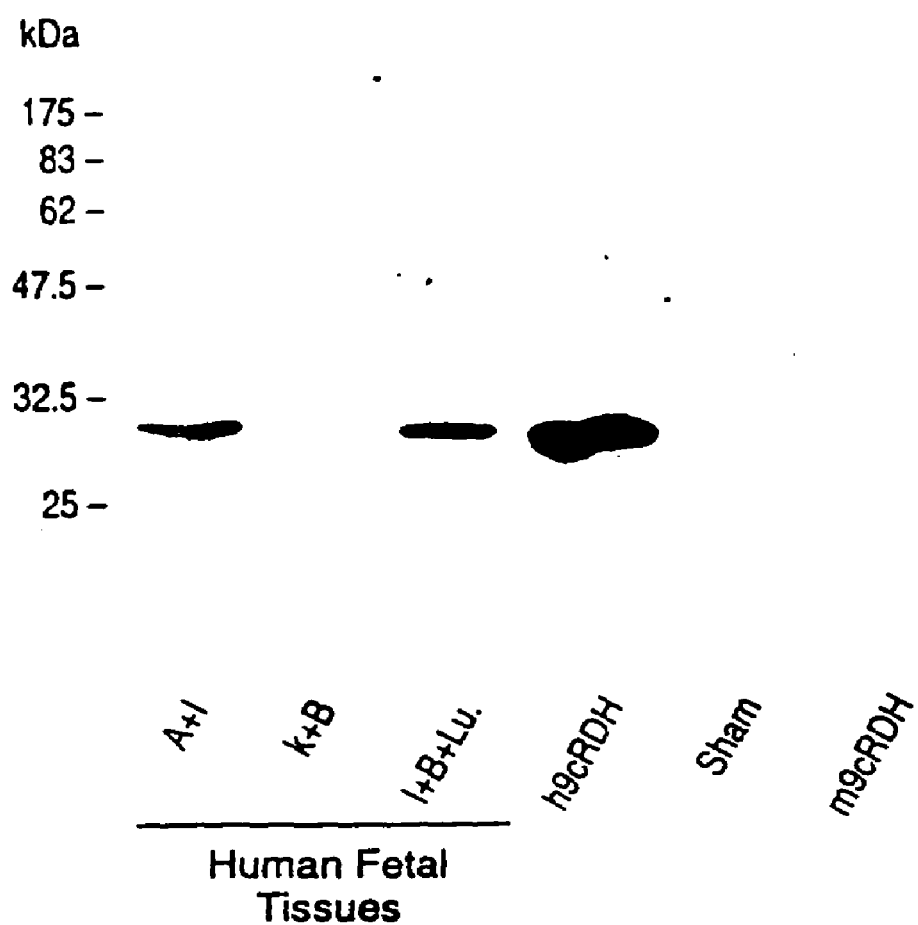

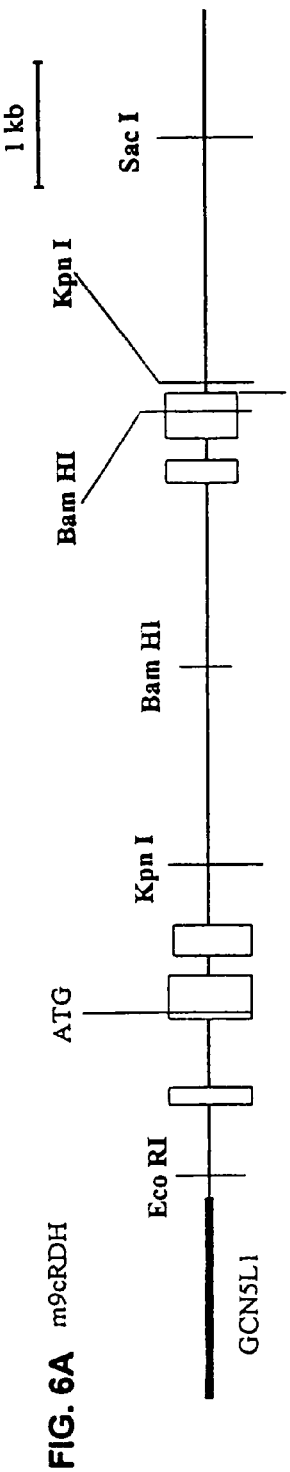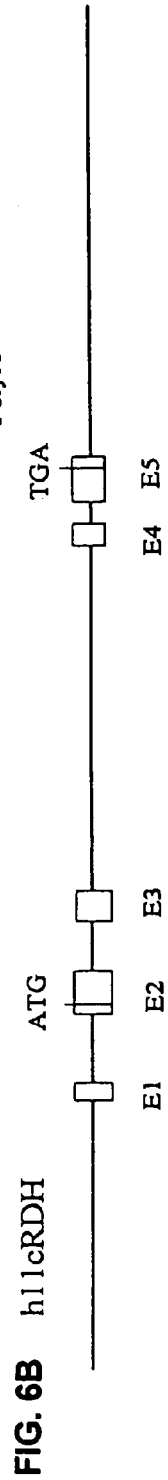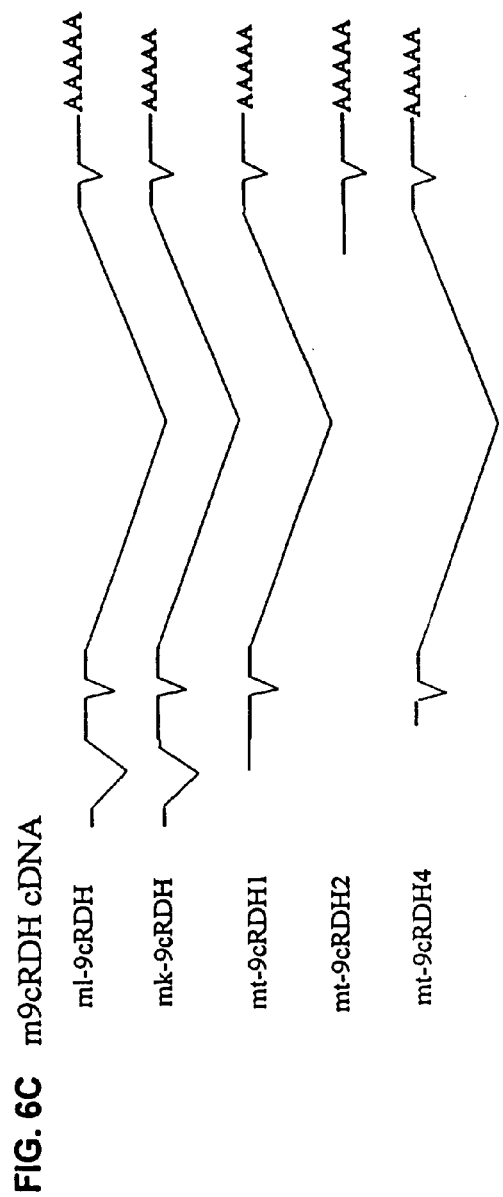
FIG. 6A m9cRDH
FIG. 6B h11cRDH
FIG. 6C m9cRDH cDNA

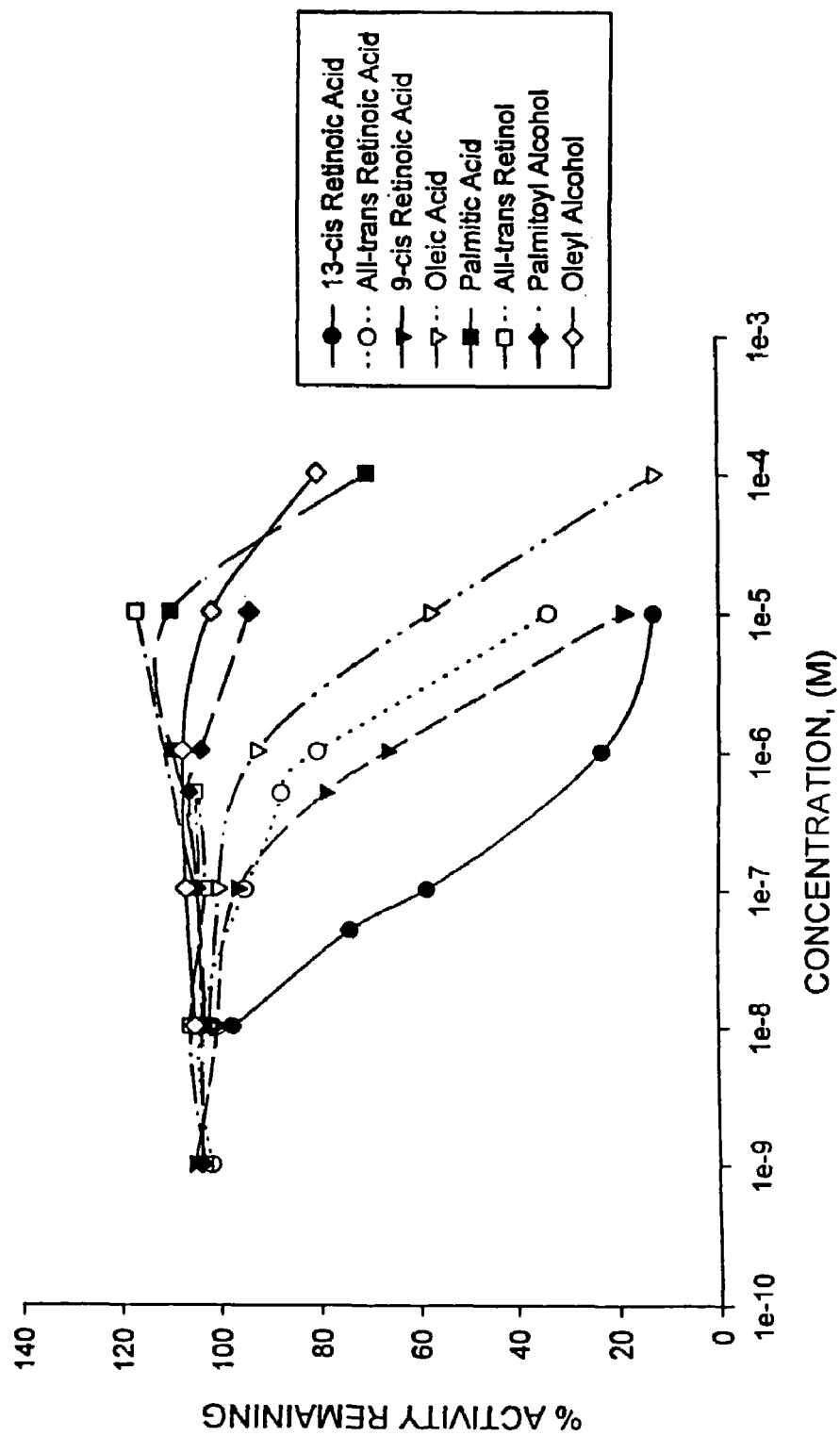
FIG. 8  INHIBITION OF HUMAN 9cRDH ACTIVITY

SEQUENCE LISTING

<160> NUMBER OF SEQ ID NOS: 13

<210> SEQ ID NO 1
<211> LENGTH: 1230
<212> TYPE: DNA
<213> ORGANISM: HOMO SAPIENS
<220> FEATURE:
<221> NAME/KEY: misc_feature
<222> LOCATION: (181)..(181)
<223> OTHER INFORMATION: N = UNKNOWN
<220> FEATURE:
<221> NAME/KEY: misc_feature
<222> LOCATION: (719)..(719)
<223> OTHER INFORMATION: N = UNKNOWN
<220> FEATURE:
<221> NAME/KEY: misc_feature
<222> LOCATION: (734)..(734)
<223> OTHER INFORMATION: N = UNKNOWN
<220> FEATURE:
<221> NAME/KEY: misc_feature
<222> LOCATION: (765)..(765)
<223> OTHER INFORMATION: N = UNKNOWN
<220> FEATURE:
<221> NAME/KEY: misc_feature
<222> LOCATION: (276)..(276)
<223> OTHER INFORMATION: N = UNKNOWN
<220> FEATURE:
<221> NAME/KEY: misc_feature
<222> LOCATION: (351)..(351)
<223> OTHER INFORMATION: N = UNKNOWN

<400> SEQUENCE: 1

```
gagactggga gcagtctctt aaacaaaagc aaaagaataa gcttcgggcg ctgtagtacc      60
tgccagcttt cgccacagga ggctgccacc tgtaggtcac ttgggctcca gctatgtggc     120
tgcctcttct gctgggtgcc ttactctggg cagtgctgtg gttgctcagg gaccggcaga     180
ncctgcccgc cagcaatgcc tttgtcttca tcaccggctg tgactcaggc tttgggcgcc     240
ttctggcact gcagctggac cagaaaagct tccgantcct ggccagctgc ctgaccccct     300
ccggggcgga ggacctgcag ggggtggctt cttccggctt caacaccacc ntgttggata     360
tcactgatcc ccagagcttc cagcaggcag ccaagtgggt ggagatgcac gttaaggaag     420
cagggctttt tggtctggtg aataatgctg gtgtggctgg tatcatcgga cccacaccat     480
ggctgacccg ggacgatttc cagcgggtgc tgaatgtgaa cacaatgggt cccatcgggg     540
tcacccttgc cctgctgcct ctgctgcagc aagcccgggg ccgggtgatc aacatcacca     600
gcgtcctggg tcgcctggca gccaatggtg ggggctactg tgtctccaaa tttggcctgg     660
aggccttctc tgacagcctg aggcgggatg tagctcattt tgggatacgg gagtccatng     720
tggagcctgg tttnttccga accctgtga ccaacttgga gagtntggag aaaaccctgc     780
aggcctgctg ggcacggctg cctcctgcca cacaggccca ctatgggggg gccttcctca     840
ccaagtacct gaaaatgcaa cagcgcatca tgaacctgat ctgtgacccg gacctaacca     900
aggtgagccg atgcctggag catgccctga ctgctcgaca ccccgaacc cgctacagcc     960
caggttggga tgccaagctg ctctggctgc ctgcctccta cctgccagcc agcctggtgg    1020
atgctgtgct cacctgggtc cttcccaagc ctgcccaagc agtctactga atccagcctt    1080
ccagcaagag attgttttttc aaggacaagg actttgattt atttctgccc ccaccctggt    1140
actgcctggt gcctgccaca aaataagcac taacaaaagt gtattgttta aaaaataaaa    1200
agaaggtggg cagaaatgtg cccagtggaa                                      1230
```

```
<210> SEQ ID NO 2
<211> LENGTH: 318
<212> TYPE: PRT
<213> ORGANISM: HOMO SAPIENS
<220> FEATURE:
<221> NAME/KEY: MISC_FEATURE
<222> LOCATION: (23)..(23)
<223> OTHER INFORMATION: x = unknown
<220> FEATURE:
<221> NAME/KEY: MISC_FEATURE
<222> LOCATION: (55)..(55)
<223> OTHER INFORMATION: x = unknown
<220> FEATURE:
<221> NAME/KEY: MISC_FEATURE
<222> LOCATION: (80)..(80)
<223> OTHER INFORMATION: x = unknown
<220> FEATURE:
<221> NAME/KEY: MISC_FEATURE
<222> LOCATION: (202)..(202)
<223> OTHER INFORMATION: x = unknown
<220> FEATURE:
<221> NAME/KEY: MISC_FEATURE
<222> LOCATION: (207)..(207)
<223> OTHER INFORMATION: x = unknown
<220> FEATURE:
<221> NAME/KEY: MISC_FEATURE
<222> LOCATION: (218)..(218)
<223> OTHER INFORMATION: x = unknown

<400> SEQUENCE: 2

Met Trp Leu Pro Leu Leu Gly Ala Leu Leu Trp Ala Val Leu Trp
1               5                   10                  15

Leu Leu Arg Asp Arg Gln Xaa Leu Pro Ala Ser Asn Ala Phe Val Phe
            20                  25                  30

Ile Thr Gly Cys Asp Ser Gly Phe Gly Arg Leu Leu Ala Leu Gln Leu
        35                  40                  45

Asp Gln Lys Ser Phe Arg Xaa Leu Ala Ser Cys Leu Thr Pro Ser Gly
    50                  55                  60

Ala Glu Asp Leu Gln Gly Val Ala Ser Ser Gly Phe Asn Thr Thr Xaa
65                  70                  75                  80

Leu Asp Ile Thr Asp Pro Gln Ser Phe Gln Gln Ala Ala Lys Trp Val
                85                  90                  95

Glu Met His Val Lys Glu Ala Gly Leu Phe Gly Leu Val Asn Asn Ala
            100                 105                 110

Gly Val Ala Gly Ile Ile Gly Pro Thr Pro Trp Leu Thr Arg Asp Asp
        115                 120                 125

Phe Gln Arg Val Leu Asn Val Asn Thr Met Gly Pro Ile Gly Val Thr
    130                 135                 140

Leu Ala Leu Leu Pro Leu Leu Gln Gln Ala Arg Gly Arg Val Ile Asn
145                 150                 155                 160

Ile Thr Ser Val Leu Gly Arg Leu Ala Ala Asn Gly Gly Gly Tyr Cys
                165                 170                 175

Gly Ser Lys Phe Gly Leu Glu Ala Phe Ser Asp Ser Leu Arg Arg Asp
            180                 185                 190

Val Ala His Phe Gly Ile Arg Glu Ser Xaa Val Glu Pro Gly Xaa Phe
        195                 200                 205

Arg Thr Pro Val Thr Asn Leu Glu Ser Xaa Glu Lys Thr Leu Gln Ala
    210                 215                 220

Cys Trp Ala Arg Leu Pro Pro Ala Thr Gln Ala His Tyr Gly Gly Ala
225                 230                 235                 240

Phe Leu Thr Lys Tyr Leu Lys Met Gln Gln Arg Ile Met Asn Leu Ile
                245                 250                 255
```

```
Cys Asp Pro Asp Leu Thr Lys Val Ser Arg Cys Leu Glu His Ala Leu
            260                 265                 270

Thr Ala Arg His Pro Arg Thr Arg Tyr Ser Pro Gly Trp Asp Ala Lys
            275                 280                 285

Leu Leu Trp Leu Pro Ala Ser Tyr Leu Pro Ala Ser Leu Val Asp Ala
            290                 295                 300

Val Leu Thr Trp Val Leu Pro Lys Pro Ala Gln Ala Val Tyr
305                 310                 315

<210> SEQ ID NO 3
<211> LENGTH: 313
<212> TYPE: PRT
<213> ORGANISM: HOMO SAPIENS

<400> SEQUENCE: 3

Met Trp Leu Pro Leu Leu Gly Val Leu Leu Trp Ala Ala Leu Trp
1               5                   10                  15

Leu Leu Arg Asp Arg Gln Cys Leu Pro Ala Ser Asp Ala Phe Ile Phe
            20                  25                  30

Ile Thr Gly Cys Asp Ser Gly Phe Gly Arg Leu Leu Ala Leu Arg Leu
            35                  40                  45

Asp Gln Arg Gly Phe Arg Val Leu Ala Ser Cys Leu Thr Pro Ser Gly
            50                  55                  60

Ala Glu Asp Leu Gln Arg Val Ala Ser Ser Arg Leu His Thr Thr Leu
65                  70                  75                  80

Leu Asp Val Thr Asp Pro Gln Ser Ile Arg Gln Ala Val Lys Trp Val
                85                  90                  95

Glu Thr His Val Gly Glu Ala Gly Leu Phe Gly Leu Val Asn Asn Ala
            100                 105                 110

Gly Val Ala Gly Ile Ile Gly Pro Thr Pro Trp Gln Thr Arg Glu Asp
            115                 120                 125

Phe Gln Arg Val Leu Asn Val Asn Thr Leu Gly Pro Ile Gly Val Thr
            130                 135                 140

Leu Ala Leu Leu Pro Leu Leu Gln Ala Arg Gly Arg Val Ile Asn
145                 150                 155                 160

Ile Thr Ser Val Leu Gly Arg Leu Ala Ala Asn Gly Gly Gly Tyr Cys
                165                 170                 175

Val Ser Lys Phe Gly Leu Glu Ala Phe Ser Asp Ser Leu Arg Arg Asp
            180                 185                 190

Val Ala Pro Phe Gly Val Arg Val Ser Ile Val Glu Pro Gly Phe Phe
            195                 200                 205

Arg Thr Pro Val Thr Asn Leu Glu Thr Leu Glu Cys Trp Ala Arg Leu
            210                 215                 220

Pro Pro Ala Thr Gln Ala Leu Tyr Gly Glu Ala Phe Leu Thr Lys Tyr
225                 230                 235                 240

Leu Arg Val Gln Gln Arg Ile Met Asn Met Ile Cys Asp Pro Asp Leu
                245                 250                 255

Ala Lys Val Ser Arg Cys Leu Glu His Ala Leu Thr Ala Arg His Pro
            260                 265                 270

Arg Thr Arg Tyr Ser Pro Gly Trp Asp Ala Lys Leu Leu Trp Leu Pro
            275                 280                 285

Ala Ser Tyr Leu Pro Ala Arg Leu Val Asp Ala Val Leu Ala Trp Val
            290                 295                 300

Leu Pro Lys Pro Ala Gln Thr Val Tyr
305                 310
```

-continued

<210> SEQ ID NO 4
<211> LENGTH: 317
<212> TYPE: PRT
<213> ORGANISM: RATTUS SP.

<400> SEQUENCE: 4

Met Trp Leu Tyr Leu Leu Ala Leu Val Gly Leu Trp Asn Leu Leu Arg
1               5                   10                  15

Leu Phe Arg Glu Arg Lys Val Val Ser His Leu Gln Asp Lys Tyr Val
            20                  25                  30

Phe Ile Thr Gly Cys Asp Ser Gly Phe Gly Asn Leu Leu Ala Arg Gln
        35                  40                  45

Leu Asp Arg Arg Gly Met Arg Val Leu Ala Ala Cys Leu Thr Glu Lys
    50                  55                  60

Gly Ala Glu Gln Leu Arg Ser Lys Thr Ser Asp Arg Leu Glu Thr Val
65                  70                  75                  80

Ile Leu Asp Val Thr Lys Thr Glu Ser Ile Val Ala Ala Thr Gln Trp
                85                  90                  95

Val Lys Glu Arg Val Gly Asn Thr Gly Leu Trp Gly Leu Val Asn Asn
            100                 105                 110

Ala Gly Ile Ser Gly His Leu Gly Pro Asn Glu Trp Met Asn Lys Gln
        115                 120                 125

Asn Ile Ala Ser Val Leu Asp Val Asn Leu Leu Gly Met Ile Glu Val
    130                 135                 140

Thr Leu Ser Thr Val Pro Leu Val Arg Lys Ala Arg Gly Arg Val Val
145                 150                 155                 160

Asn Val Ala Ser Ile Ala Gly Arg Leu Ser Phe Cys Gly Gly Gly Tyr
                165                 170                 175

Cys Ile Ser Lys Tyr Gly Val Glu Ala Phe Ser Asp Ser Leu Arg Arg
            180                 185                 190

Glu Leu Ser Tyr Phe Gly Val Lys Val Ala Ile Val Glu Pro Gly Phe
        195                 200                 205

Phe Arg Thr Asp Val Thr Asn Gly Val Thr Leu Ser Ser Asn Phe Gln
    210                 215                 220

Met Leu Trp Asp Gln Thr Ser Ser Glu Val Arg Glu Val Tyr Gly Glu
225                 230                 235                 240

Asn Tyr Leu Ala Ser Tyr Leu Lys Met Leu Asn Gly Leu Asp Gln Arg
                245                 250                 255

Cys Asn Lys Asp Leu Ser Leu Val Thr Asp Cys Met Glu His Ala Leu
            260                 265                 270

Thr Ser Cys His Pro Arg Thr Arg Tyr Ser Ala Gly Trp Asp Ala Lys
        275                 280                 285

Phe Phe Tyr Leu Pro Met Ser Tyr Leu Pro Thr Phe Leu Val Asp Ala
    290                 295                 300

Leu Phe Tyr Trp Thr Ser Pro Lys Pro Glu Lys Ala Leu
305                 310                 315

<210> SEQ ID NO 5
<211> LENGTH: 317
<212> TYPE: PRT
<213> ORGANISM: BOVINE SP.

<400> SEQUENCE: 5

Met Trp Leu Tyr Leu Leu Ala Leu Val Gly Leu Trp Asn Leu Leu Arg
1               5                   10                  15

Phe Leu Arg Glu Arg Lys Val Val Ser His Leu Gln Asp Lys Tyr Val
                20                  25                  30

Phe Ile Thr Gly Cys Asp Ser Gly Phe Gly Asn Leu Leu Ala Arg Gln
            35                  40                  45

Leu Asp Arg Arg Gly Met Arg Val Leu Ala Ala Cys Leu Thr Glu Lys
        50                  55                  60

Gly Ala Glu Gln Leu Arg Ser Lys Thr Ser Asp Arg Leu Glu Thr Val
65                  70                  75                  80

Ile Leu Asp Val Thr Lys Thr Glu Ser Ile Val Ala Ala Thr Gln Trp
                85                  90                  95

Val Lys Glu Arg Val Gly Asn Arg Gly Leu Trp Gly Leu Val Asn Asn
            100                 105                 110

Ala Gly Ile Ser Val Pro Val Gly Pro Asn Glu Trp Met Arg Lys Lys
        115                 120                 125

Asp Phe Ala Ser Val Leu Asp Val Asn Leu Leu Gly Val Ile Glu Val
130                 135                 140

Thr Leu Asn Met Leu Pro Leu Val Arg Lys Ala Arg Gly Arg Val Val
145                 150                 155                 160

Asn Ile Ala Ser Thr Met Gly Arg Met Ser Leu Val Gly Gly Gly Tyr
                165                 170                 175

Cys Ile Ser Lys Tyr Gly Val Glu Ala Phe Ser Asp Ser Leu Arg Arg
            180                 185                 190

Glu Leu Thr Tyr Phe Gly Val Lys Val Ala Ile Ile Glu Pro Gly Gly
        195                 200                 205

Phe Lys Thr Asn Val Thr Asn Met Glu Arg Leu Ser Asp Asn Leu Lys
210                 215                 220

Lys Leu Trp Asp Gln Thr Thr Glu Glu Val Lys Glu Ile Tyr Gly Glu
225                 230                 235                 240

Lys Phe Gln Asp Ser Tyr Met Lys Ala Met Glu Ser Leu Val Asn Thr
                245                 250                 255

Cys Ser Gly Asp Leu Ser Leu Val Thr Asp Cys Met Glu His Ala Leu
            260                 265                 270

Thr Ser Cys His Pro Arg Thr Arg Tyr Ser Pro Gly Trp Asp Ala Lys
        275                 280                 285

Phe Phe Tyr Leu Pro Met Ser Tyr Leu Pro Thr Phe Leu Ser Asp Ala
290                 295                 300

Val Ile His Trp Gly Ser Val Lys Pro Ala Arg Ala Leu
305                 310                 315

<210> SEQ ID NO 6
<211> LENGTH: 252
<212> TYPE: DNA
<213> ORGANISM: MOUSE SP.
<220> FEATURE:
<221> NAME/KEY: misc_feature
<222> LOCATION: (135)..(136)
<223> OTHER INFORMATION: n = unknown
<220> FEATURE:
<221> NAME/KEY: misc_feature
<222> LOCATION: (139)..(143)
<223> OTHER INFORMATION: n = unknown

<400> SEQUENCE: 6
cgccagtgtg ctggaattcg gcacgaggct tagctgtagc tagtgtggga gcctgggaag      60
tctaggagca aagtctctca agcagacaga aagctacagc ttcacacatt gtgttgcctg     120
ccagctttcc ccagnnagnn nnngctgccc tcagcagggc atctcatccc atcatgtggc     180

```
tgcctctgct tctgggtgcc ttgctgtggg cagtgctgtg gttgctcaga gaccggcaga      240
gcctgccggc ca                                                          252
```

<210> SEQ ID NO 7
<211> LENGTH: 200
<212> TYPE: DNA
<213> ORGANISM: MOUSE SP.
<220> FEATURE:
<221> NAME/KEY: misc_feature
<222> LOCATION: (7)..(7)
<223> OTHER INFORMATION: n = unknown
<220> FEATURE:
<221> NAME/KEY: misc_feature
<222> LOCATION: (18)..(18)
<223> OTHER INFORMATION: n = unknown
<220> FEATURE:
<221> NAME/KEY: misc_feature
<222> LOCATION: (44)..(44)
<223> OTHER INFORMATION: n = unknown
<220> FEATURE:
<221> NAME/KEY: misc_feature
<222> LOCATION: (45)..(45)
<223> OTHER INFORMATION: n = unknown
<220> FEATURE:
<221> NAME/KEY: misc_feature
<222> LOCATION: (83)..(84)
<223> OTHER INFORMATION: n = unknown

<400> SEQUENCE: 7

```
tggctcngag gccaagantc ggaccatgag cagacagaaa gctnnagctt cacacattgt      60
gttgcctgcc agctttcccc agnnagccta ggctgccctc agcagggcat ctcatcccat     120
catgtggctg cctctgcttc tgggtgcctt gctgtgggca gtgctgtggt tgctcagaga     180
ccggcagagc ctgccggcca                                                 200
```

<210> SEQ ID NO 8
<211> LENGTH: 254
<212> TYPE: DNA
<213> ORGANISM: MOUSE SP.

<400> SEQUENCE: 8

```
tgcccataat ctgtttcaca caataagcca tagcttgcca agcatatagt ctcatctgct      60
cagaccagac atttccagct aagtaaatgt taggggccaa ggctaagggg gtagaggaaa     120
tgacaagttt tcctgcccag cctaagctgc cctcagcagg gcatctcatc ccatcatgtg     180
gctgcctctg cttctgggtg ccttgctgtg ggcagtgctg tggttgctca gagaccggca     240
gagcctgccg gcca                                                       254
```

<210> SEQ ID NO 9
<211> LENGTH: 20
<212> TYPE: PRT
<213> ORGANISM: MOUSE SP.

<400> SEQUENCE: 9

```
His Tyr Gly Gly Ala Phe Leu Lys Tyr Leu Lys Met Gln Gln Arg Ile
1               5                   10                  15

Met Asn Leu Ile
            20
```

<210> SEQ ID NO 10
<211> LENGTH: 1229
<212> TYPE: DNA
<213> ORGANISM: MOUSE SP.

-continued

```
<400> SEQUENCE: 10
tacgggctcg gagccagacg ccgttgctat tcggacagct tccatagttg agctgaacta    60
gaagtctcag cagacagaaa gctacagctt cacacattgt gttgcctgcc agctttcccc   120
agagcctagc tgccctcagc agggcatctc atcccatcat gtggctgcct ctgcttctgg   180
gtgccttgct gtgggcagtg ctgtggttgc tcagagaccg gcagagcctg ccggccagtg   240
atgctttcat cttcatcact ggctgtgact ctggcttttgg gcgccttctg gcactgcaac   300
ttgaccagaa gggcttccaa gtcctggccg gctgcctgac ccctctggga gcagaagacc   360
tgcagcagat ggcctcctcc cgcctccaca caacactact ggatatcact gatcccaga    420 atgtccagca agttgccaag tgggtgaaga cacgtgttgg agaaactgga cttttttggtc   480 tggtgaataa cgctggcgta gctggtatca tcgggcccac accatggcta acacaggatg   540
atttccagag agtactgagt gtgaacacac tggggcccat cggtgtcacc cttgccctgc   600
tgcccctgct acagcaggcc aggggtcggg tggtcaacat caccagtgtc ttgggccgca   660
tagcagccaa tggcgggggc tactgtgtct ccaagtttgg cctggaggcc ttctctgaca   720
gcctgaggcg ggacatggct ccgttcggag tacaagtctc cattgtggag cctggcttct   780
ttcgaacccc tgtgaccaac ctggagagtc tggagagcac cctgaaggct gttgggccc    840 ggctacctcc agctatacag gcccactacg gggaagcctt cctcgatact tatcttcgag   900
tacagcgccg catcatgaac ctgatctgtg acccagaact aacgaaggtg accagctgcc   960
tggagcatgc ctgactgctc gccacccccg aacacgtaca gcccaggctg ggatgccaag  1020
ctgctctggc tgcctgcctc ctaccttcca gccagggtgg tggatgctgt gctcactgga  1080
tccttccccg gcccgcccag tcagtctcct gattccagct ttacagcaag agctgatttt  1140
gaaaagcaag gcatctattt ctgtgtctac ccagtgctgc ctggtttctg ataccaatta  1200
gctctcaata aatatttgct ttaatcaaa                                    1229

<210> SEQ ID NO 11
<211> LENGTH: 461
<212> TYPE: DNA
<213> ORGANISM: MOUSE SP.
<220> FEATURE:
<221> NAME/KEY: misc_feature
<222> LOCATION: (7)..(7)
<223> OTHER INFORMATION: n = UNKNOWN
<220> FEATURE:
<221> NAME/KEY: misc_feature
<222> LOCATION: (18)..(18)
<223> OTHER INFORMATION: n = UNKNOWN

<400> SEQUENCE: 11
tggctcngag gccaagantc ggaccatgag cagacagaaa gctacagctt cacacattgt    60
gttgcctgcc agctttcccc agagcctagg ctgccctcag cagggcatct catcccatca   120
tgtggctgcc tctgcttctg gtgccttgc tgtgggcagt gctgtggttg ctcagagacc   180
ggcagagcct gccggccagt gatgctttca tcttcatcac tggctgtgac tctggctttg   240
ggcgccttct ggcactgcaa cttgaccaga agggcttcca agtcctggcc ggctgcctga   300
ccccctctgg agcagaagac ctgcagcaga tggcctcctc ccgcctccac acaacaccac   360
tggatatcac tgatcccag aatgtccagc aagttgccaa gtgggtgaag acacgtgttg   420
gagaaactgg acttttttggt ctggtgaata acgctggcgt a                      461

<210> SEQ ID NO 12
<211> LENGTH: 1278
```

```
<212> TYPE: DNA
<213> ORGANISM: MOUSE SP.
<220> FEATURE:
<221> NAME/KEY: misc_feature
<222> LOCATION: (19)..(19)
<223> OTHER INFORMATION: n = unknown
<220> FEATURE:
<221> NAME/KEY: misc_feature
<222> LOCATION: (1246)..(1246)
<223> OTHER INFORMATION: n = unknown
<220> FEATURE:
<221> NAME/KEY: misc_feature
<222> LOCATION: (1262)..(1262)
<223> OTHER INFORMATION: n = unknown
<220> FEATURE:
<221> NAME/KEY: misc_feature
<222> LOCATION: (1264)..(1264)
<223> OTHER INFORMATION: n = unknown
<220> FEATURE:
<221> NAME/KEY: misc_feature
<222> LOCATION: (1271)..(1271)
<223> OTHER INFORMATION: n = Unknown

<400> SEQUENCE: 12
cttggtaccg agctcgganc cactagtaac ggccgccagt gtgctggaat tcggcacgag      60
gcttagctgt agctagtgtg ggagcctggg aagtctagga gcaaagtctc tcaagcagac     120
agaaagctac agcttcacac attgtgttgc ctgccagctt tccccagagg ctgccctcag     180
cagggcatct catcccatca tgtggctgcc tctgcttctg ggtgccttgc tgtgggcagt     240
gctgtggttg ctcagagacc ggcagagcct gccggccagt gatgctttca tcttcatcac     300
tggctgtgac tctggctttg ggcgccttct ggcactgcaa cttgaccaga agggcttcca     360
agtcctggcc ggctgcctga ccccctctgg agcagaagac ctgcagcaga tggcctcctc     420
ccgcctccac acaacactac tggatatcac tgatccccag aatgtccagc aagttgccaa     480
gtgggtgaag acacgtgttg agaaactgg acttttggt ctggtgaata cgctggcgt      540 agctggtatc atcgggccca caccatggct aacacaggat gatttccaga gagtactgag     600
tgtgaacaca ctggggccca tcggtgtcac ccttgccctg ctgcccctgc tacagcaggc     660 cagggtcgg gtggtcaaca tcaccagtgt cttgggccgc atagcagcca atggcggggg     720
ctactgtgtc tccaagtttg gcctggaggc cttctctgac agcctgaggc gggacatggc     780
tccgttcgga gtacaagtct ccattgtgga gcctggcttc tttcgaaccc ctgtgaccaa     840
cctggagagt ctggagagca ccctgaaggc ttgttgggcc cggctacctc cagctataca     900
ggcccactac ggggaagcct tcctcgatac ttatcttcga gtacagcgcc gcatcatgaa     960
cctgatctgt gacccagaac taacgaaggt gaccagctgc ctggagcatg ccctgactgc    1020
tcgccacccc cgaacacgct acagcccagg ctgggatgcc aagctgctct ggctgcctgc    1080
ctcctacctt ccagccaggg tggtggatgc tgtgctcacc tggatccttc cccggcccgc    1140
ccagtcagtc tcctgattcc agctttacag caagaagctg attttgaaaa gcaaggcatc    1200
tatttctgtg tctacccagt gctgcctggt ttctgatacc aattangctc tcaataaata    1260
tntntgcttt naatcaaa                                                  1278

<210> SEQ ID NO 13
<211> LENGTH: 1334
<212> TYPE: DNA
<213> ORGANISM: MOUSE SP.

<400> SEQUENCE: 13
gagtcacaca gggataggtc tgcccacagg accagctcag gtttatttca ttagctacaa      60
```

```
-continued
agtgcttgcc cataatctgt ttcacacaat aagccatagc ttgccaatcc tctgccaagc    120
atatagtctc atctgctcag accagacatt tccagctaag taaatgttag gggccaaggc    180
taaaggggta gaggaaatga caagttttcc tgcccagcct aagctgccct cagcagggca    240
tctcatccca tcatgtggct gcctctgctt ctgggtgcct tgctgtgggc agtgctgtgg    300
ttgctcagag accggcagag cctgccggcc agtgatgctt tcatcttcat cactggctgt    360
gactctggct ttgggcgcct tctggcactg caacttgacc agaagggctt ccaagtcctg    420
gccggctgcc tgaccccctc tggagcagaa gacctgcagc agatggcctc ctcccgcctc    480
cacacaacac tactggatat cactgatccc cagaatgtcc agcaagttgc caagtgggtg    540
aagacacgtg ttggagaaac tggacttttt ggtctggtga ataacgctgg cgtagctggt    600
atcatcgggc ccacaccatg gctaacacag gatgatttcc agagagtact gagtgtgaac    660
acactggggc ccatcggtgt caccttgcc ctgctgcccc tgctacagca ggccaggggt    720
cgggtggtca acatcaccag tgtcttgggc cgcatagcag ccaatggcgg gggctactgt    780
gtctccaagt ttggcctgga ggccttctct gacagcctga ggcgggacat ggctccgttc    840
ggagtacaag tctccattgt ggagcctggc ttctttcgaa ccctgtgac caacctggag    900
agtctggaga gcaccctgaa ggcttgttgg gcccggctac ctccagctat acaggcccac    960
tacggggaag ccttcctcga tacttatctt cgagtacagc gccgcatcat gaacctgatc    1020
tgtgacccag aactaacgaa ggtgaccagc tgcctggagc atgccgtgac tgctcgccac    1080
ccccgaaaca gttacagccc aggctgggat gccaagctgc tctggctgcc tgcctcctac    1140
cttccagcca gggtggtgga tgctgtgctc acatggatcc ttccccggcc cgcccagtca    1200
gtctcctgat tccagcttta cagcaagagg ctgattttga aaagcaaggc atctatttct    1260
gtgtctaccc agtgctgcct ggtttctgat accaattagg ctctcaataa atatgtattg    1320
ctttaaatca aaaa                                                      1334
```

POTENT INHIBITORS OF HUMAN 9-CIS RETINOL DEHYDROGENASE

This application is a continuation of PCT International Application No. PCT/US98/20271, filed 29 Sep. 1998, designating the United States of America, which is a continuation-in-part of and claims the priority of U.S. Ser. No. 08/940,424, filed Sep. 29, 1997 now U.S. Pat. No. 6,171,837, the contents of which are hereby incorporated by reference into the present application.

The invention disclosed was herein made in the course of work under under NIH Grant No. RO1DK 52444 from the The National Institutes of Health and from National Institutes of Health training grant T32 DK07328. Accordingly, the U.S. Government has certain rights in this invention.

Throughout this application, various references are referred to within parentheses. Disclosures of these publications in their entireties are hereby incorporated by reference into this application to more fully describe the state of the art to which this invention pertains. Full bibliographic citation for these references may be found at the end of this application, preceding the claims.

BACKGROUND OF THE INVENTION

All-trans- and 9-cis-retinoic acid are active retinoids for regulating expression of retinoid responsive genes, serving as ligands for two classes of ligand-dependent transcription factors, the retinoic acid receptors and retinoid X receptors. Little is known, however, regarding 9-cis-retinoic acid formation. We have obtained a 1.4-kilobase cDNA clone from a normalized human breast tissue library, which when expressed in CHO cells encodes a protein that avidly catalyzes oxidation of 9-cis-retinol to 9-cis-retinaldehyde. This protein also catalyzes oxidation of 13-cis-retinol at a rate approximately 10% of that of the 9-cis isomer but does not catalyze all-trans-retinol oxidation. NAD+ was the preferred electron acceptor for oxidation of 9-cis-retinol, although NADP+ supported low rates of 9-cis-retinol oxidation. The rate of 9-cis-retinol oxidation was optimal at pHs between 7.5 and 8. Sequence analysis indicates that the cDNA encodes a protein of 319 amino acids that resembles members of the short chain alcohol dehydrogenase protein family. mRNA for the protein is most abundant in human mammary tissue followed by kidney and testis, with lower levels of expression in liver, adrenals, lung, pancreas, and skeletal muscle. We propose that this cDNA encodes a previously unknown stereospecific enzyme, 9-cis-retinol dehydrogenase, which probably plays a role in 9-cis-retinoic acid formation.

Retinoids (vitamin A and its analogs) are essential dietary substances that are needed by mammals for reproduction, normal embryogenesis, growth, vision, and maintaining normal cellular differentiation and the integrity of the immune system (1–5). Within cells, retinoids regulate gene transcription acting through ligand-dependent transcription factors, the retinoic acid receptors (RARs)[1], and the retinoid X receptors (RXRs) (6,7). All-trans-retinoic acid binds only to RARs with high affinity, whereas its 9-cis isomer binds with high affinity to both RARs and RXRs. The actions of all-trans- and 9-cis-retinoic acid in regulating cellular responses are distinct and not interchangeable.

In contrast to the great explosion of information regarding the actions of retinoid receptors in regulating gene transcription, information regrading how the abundant precursor retinol is physiologically activated to form the ligands needed to activate retinoid receptors is only slowly emerging (see Refs. 8 and 9 for recent reviews). It is clear that the pathway for conversion of retinol to retinoic acid involves first the oxidation of retinol to retinaldehyde and then the oxidation of retinaldehyde to retinoic acid. Numerous enzymes that are able to catalyze either retinol or retinaldehyde oxidation have been identified, purified, and/or characterized (8–10). These enzymes are members of four distinct families: the alcohol dehydrogenases, the short chain alcohol dehydrogenases, the aldehyde dehydrogenases, and cytochrome P-450s (8–10). At present, the most attention has focused on enzymes responsible for the oxidation of all-trans-retinol to all-trans-retinaldehyde (11–15). Several recent reports have indicated that both alcohol dehydrogenases and short chain alcohol dehydrogenases may be responsible for catalyzing all-trans-retinol oxidation (11–15), but the exact in vivo roles of each of these dehydrogenases in all-trans-retinoic acid formation remains controversial (8).

9-cis-Retinoic acid has been reported to be present in mammalian tissues and cells (16–18), but it has not been convincingly established how 9-cis-retinoic acid is formed within tissues and cells. Urbach and Rando have reported that liver microsomes can nonenzymatically catalyze the isomerization of all-trans-retinoic acid to the 9-cis isomer (19). Others have demonstrated that 9-cis-5-carotene can be converted to 9-cis-retinoic acid within rat tissues (20). However, this latter pathway cannot be an essential one for 9-cis-retinoic acid formation because rats maintained on a β-carotene-free purified diet containing only retinol as a precursor for retinoic acid formation are normal. In this communication, we report the characterization of a cDNA clone for a novel human enzyme that we have designated 9-cis-retinol dehydrogenase (9cRDH) and that catalyzes in a stereospecific manner the oxidation of 9-cis-retinol to 9-cis-retinaldehyde, a first enzymatic step needed for 9-cis-retinoic acid formation. Because it has been established that 9-cis-retinaldehyde can be further oxidized to 9-cis-retinoic acid by abundant tissue retinaldehyde dehydrogenases (21–23), it is possible that 9cRDH catalyzes a key oxidation step in the formation of 9-cis-retinoic acid.

SUMMARY OF THE INVENTION

This invention provides an isolated nucleic acid molecule encoding a mammalian 9-cis-retinol dehydrogenase. In a preferred embodiment the isolated nucleic acid is a cDNA molecule which encodes a human 9-cis-retinol dehydrogenase. In an embodiment the cDNA molecule encodes a mouse 9-cis-retinol dehydrogenase. In another preferred embodiment the isolated nucleic acid molecule has the nucleotide sequence shown in FIG. 1A (SEQ. ID NO: 1). In another embodiment the isolated nucleic acid molecule has the nucleotide sequence shown in SEQ. ID NO: 6. In yet another embodiment the isolated nucleic acid molecule has the nucleotide sequence shown in SEQ. ID NO: 7. In still another embodiment the isolated nucleic acid molecule has the nucleotide sequence shown in SEQ. ID NO: 8.

This invention provides a purified 9-cis-retinol dehydrogenase. In an embodiment a 9-cis-retinol dehydrogenase is encoded by the isolated nucleic acid molecule encoding a mammalian 9-cis-retinol dehydrogenase. In a preferred embodiment the 9-cis-retinol dehydrogenase has the amino acid sequence set forth in FIG. 1B (SEQ. ID NO: 2).

This invention provides a mouse 9-cis-retinol dehydrogenase, wherein the nucleic acid molecule encoding the 9-cis-retinol dehydrogenase has the nucleotide sequence shown in any of SEQ. ID NOS: 6, 7, and 8.

This invention also provides a vector comprising the isolated mammalian nucleic acid molecule encoding a mammalian 9-cis-retinol dehydrogenase. In an embodiment the vector is a plasmid.

In an embodiment, a full-length cDNA nucleic acid molecule encoding a human 9-cis-retinol dehydrogenase is inserted by EcoR1/Not1 into a pcDNA3 plasmid (Invitrogen®) and the resulting plasmid is designated as pcDNA3-1. In an embodiment, a full-length cDNA nucleic acid molecule encoding a mouse liver 9-cis-retinol dehydrogenase is inserted by EcoR1/Not1 into a pcDNA3 plasmid (Invitrogen®) and the resulting plasmid is designated as pcDNA3-2. In an embodiment, a full-length cDNA nucleic acid molecule encoding a mouse kidney 9-cis-retinol dehydrogenase is inserted by EcoR1/Not1 into a pcDNA3 plasmid (Invitrogen®) and the resulting plasmid is designated as pcDNA3-3. In an embodiment, a full-length cDNA nucleic acid molecule encoding a mouse testis 9-cis-retinol dehydrogenase is inserted by EcoR1/Not1 into a pcDNA3 plasmid (Invitrogen®) and the resulting plasmid is designated as pcDNA3-4.

This invention provides a nucleic acid probe comprising a nucleic acid molecule of at least 15 nucleotides capable of specifically hybridizing with a unique sequence included within the sequence of an isolated nucleic acid molecule encoding a mammalian 9-cis-retinol dehydrogenase.

This invention provides a nucleic acid probe comprising a nucleic acid molecule of at least 15 nucleotides which is complementary to a sequence of the isolated nucleic acid molecule encoding a mammalian 9-cis-retinol dehydrogenase.

This invention provides a method of detecting expression of a mammalian 9-cis-retinol dehydrogenase in a cell which comprises: a) incubating a sample of cells with a retinol and an electron acceptor under conditions permitting oxidation of retinol to retinaldehyde; b) separating the resulting retinol and the retinaldehyde; and c) determining the quantities of the retinol and the retinaldehyde separated in step (b), thereby detecting expression of a mammalian 9-cis-retinol dehydrogenase in the cell.

This invention provides a method of detecting expression of a mammalian 9-cis-retinol dehydrogenase in a tissue which comprises: a) isolating total mRNA from a sample of the tissue; b) contacting the total mRNA with a nucleic acid probe capable of specifically hybridizing with a unique sequence included within the sequence of a nucleic acid molecule encoding a mammalian 9-cis-retinol dehydrogenase, wherein the sequence of a nucleic acid molecule encoding a mammalian 9-cis-retinol dehydrogenase is labeled with a detectable marker, under hybridizing conditions; and c) detecting the presence of mRNA which has hybridized to the nucleic acid probe capable of specifically hybridizing with a unique sequence included within the sequence of a nucleic acid molecule encoding a mammalian 9-cis-retinol dehydrogenase, thereby detecting expression of a mammalian 9-cis-retinol dehydrogenase in the tissue.

This invention further provides a method of detecting an compound capable of inhibiting a 9-cis-retinol dehydrogenase which comprises: a) incubating a 9-cis-retinol dehydrogenase and an electron acceptor under conditions permitting oxidation of a retinol to a retinaldehyde; b) separating the resulting retinol and the retinaldehyde produced in step (a); c) incubating a compound capable of inhibiting a 9-cis-retinol dehydrogenase with a 9-cis-retinol dehydrogenase and an electron acceptor under conditions permitting inhibition of oxidation of a retinol to a retinaldehyde, the 9-cis-retinol dehydrogenase and the electron acceptor being the same 9-cis-retinol dehydrogenase and the same electron acceptor incubated in step (a); d) separating the resulting retinol and the retinaldehyde produced in step (c); e) determining the quantities of the retinol and the retinaldehyde separated in steps (b) and (d), respectively, a smaller quantity of retinaldehyde and a greater quantity of retinol determined in step (d) indicating an inhibition of 9-cis-retinol dehydrogenase activity; and f) comparing the amount of inhibition of 9-cis-retinol dehydrogenase activity in step (d) with the amount of retinaldehyde and retinol resulting in step (b), a 50% inhibition of oxidation of retinol to retinaldehyde in step (d) indicating that the compound is capable of inhibiting the 9-cis-retinol dehydrogenase.

This invention provides a method of detecting an compound capable of inhibiting a 9-cis-retinol dehydrogenase in vitro, comprising: a) incubating a sample of cells with retinol and an electron acceptor under conditions permitting oxidation of retinol to retinaldehyde; b) separating the resulting retinol and the retinaldehyde produced in step (a); c) incubating a sample of cells, the cells being the same type of cells as the cells incubated in step (a), with a compound capable of inhibiting a 9-cis-retinol dehydrogenase under conditions permitting inhibition of oxidation of retinol to retinaldehyde; d) separating the resulting retinol and the retinaldehyde produced in step (c); e) determining the quantities of the retinol and the retinaldehyde separated in steps (b) and (d), respectively, a smaller quantity of retinaldehyde and a greater quantity of retinol determined in step (d) indicating an inhibition of 9-cis-retinol dehydrogenase activity; and f) comparing the amount of inhibition of 9-cis-retinol dehydrogenase activity in step (d) with the amount of retinaldehyde and retinol resulting in step (b), a 50% inhibition of oxidation of retinol to retinaldehyde in step (d) indicating that the compound is capable of inhibiting the 9-cis-retinol dehydrogenase in vitro.

This invention provides a method of detecting an compound capable of inhibiting a 9-cis-retinol dehydrogenase in vivo, comprising: a) administering a suitable dose of a compound capable of inhibiting a 9-cis-retinol dehydrogenase to a mammal; b) detecting in a tissue sample from the mammal in step (a) a presence of a retinol and a retinaldehyde; c) detecting in a tissue sample from a second mammal a presence of a retinol and a retinaldehyde; d) determining the quantities of the retinol and the retinaldehyde detected in steps (b) and (c), respectively, a smaller quantity of retinaldehyde and a greater quantity of retinol determined in step (b) indicating an inhibition of 9-cis-retinol dehydrogenase activity; and e) determining the amount of inhibition of 9-cis-retinol dehydrogenase activity in step (d), a 50% inhibition of 9-cis-retinol dehydrogenase activity indicating that the compound is capable of inhibiting the 9-cis-retinol dehydrogenase in vivo.

This invention provides a method of detecting an compound capable of inhibiting a 9-cis-retinol dehydrogenase which comprises: a) incubating a 9-cis-retinol dehydrogenase and an electron donor under conditions permitting reduction of a retinaldehyde to a retinol; b) separating the resulting retinol and the retinaldehyde produced in step (a); c) incubating a compound capable of inhibiting a 9-cis-retinol dehydrogenase with a 9-cis-retinol dehydrogenase and an electron donor under conditions permitting reduction of a retinaldehyde to a retinol, the 9-cis-retinol dehydrogenase and the electron donor being the same 9-cis-retinol dehydrogenase and the same electron donor incubated in step (a); d) separating the resulting retinol and the retinaldehyde produced in step (c); e) determining the quantities of the retinol and the retinaldehyde separated in steps (b) and (d), respectively, a larger quantity of retinaldehyde and a smaller quantity of retinol determined in step (d) indicating an inhibition of 9-cis-retinol dehydrogenase activity; and f) determining the amount of inhibition of 9-cis-retinol dehydrogenase activity in step (e), a 50% inhibition of reduction of retinaldehyde to retinol indicating that the compound is capable of inhibiting the 9-cis-retinol dehydrogenase.

This invention provides a method of detecting an compound capable of inhibiting a 9-cis-retinol dehydrogenase in vitro, comprising: a) incubating a sample of cells with retinol and an electron donor under conditions permitting reduction of a retinaldehyde to a retinol; b) separating the resulting retinol and the retinaldehyde produced in step (a); c) incubating a sample of cells, the cells being the same type of cells as the cells incubated in step (a), with a compound capable of inhibiting a 9-cis-retinol dehydrogenase under conditions permitting reduction of a retinaldehyde to a retinol, the 9-cis-retinol dehydrogenase and the electron donor being the same 9-cis-retinol dehydrogenase and the same electron donor incubated in step (a); d) separating the resulting retinol and the retinaldehyde produced in step (c); e) determining the quantities of the retinol and the retinaldehyde separated in steps (b) and (d), respectively, a larger quantity of retinaldehyde and a smaller quantity of retinol determined in step (d) indicating an inhibition of 9-cis-retinol dehydrogenase activity; and f) determining the amount of inhibition of 9-cis-retinol dehydrogenase activity in step (e), a 50' inhibition of reduction of retinaldehyde to retinol indicating that the compound is capable of inhibiting the 9-cis-retinol dehydrogenase in vitro.

This invention provides a method of detecting an compound capable of inhibiting a 9-cis-retinol dehydrogenase in vivo, comprising: a) administering a suitable dose of a compound capable of inhibiting a 9-cis-retinol dehydrogenase to a mammal; b) detecting in a tissue sample from the mammal in step (a) a presence of a retinol and a retinaldehyde; c) detecting in a tissue sample from a second mammal a presence of a retinol and a retinaldehyde; d) determining the quantities of the retinol and the retinaldehyde detected in steps (b) and (c), respectively, a larger quantity of retinaldehyde and a smaller quantity of retinol determined in step (b) indicating an inhibition of 9-cis-retinol dehydrogenase activity; e) determining the amount of inhibition of 9-cis-retinol dehydrogenase activity in step (d), a 50% inhibition of 9-cis-retinol dehydrogenase activity indicating that the compound is capable of inhibiting the 9-cis-retinol dehydrogenase in vivo.

This invention also provides a method of determining a toxic compound capable of inhibiting a 9-cis-retinol dehydrogenase comprising the method of any of the above-described methods of detecting an compound capable of inhibiting a 9-cis-retinol dehydrogenase, wherein an ability of a small concentration of the compound to inhibiting 50% of the 9-cis-retinol dehydrogenase activity indicates that the compound is toxic.

This invention provides a method for detecting a predisposition to cancer associated with the expression of a 9-cis-retinol dehydrogenase in a sample from a subject which comprises: a) determining the amount of expression of a 9-cis-retinol dehydrogenase in a cancerous tissue by performing the method of either of claims 40 and 43 on a sample of cells from the cancerous tissue; b) determining the amount of expression of a 9-cis-retinol dehydrogenase in a sample from a subject; and c) comparing the level of expression of 9-cis-retinol dehydrogenase in the sample from the subject with the level of expression of 9-cis-retinol dehydrogenase in the sample from the cancerous tissue, a comparable level of expression of 9-cis-retinol dehydrogenase indicating a predisposition to cancer in the subject.

This invention provides a method for detecting a predisposition to to a cancer or to a disease associated with the either an overexpression or an underexpression of a human 9-cis-retinol dehydrogenase in a sample from a subject which comprises: a) obtaining DNA from the sample of the subject suffering from cancer or from the disease associated with either an overexpression or an underexpression of a human 9-cis-retinol dehydrogenase; b) performing a restriction digest of the DNA with a panel of restriction enzymes; c) separating the resulting DNA fragments by size fractionation; d) contacting the resulting DNA fragments with a nucleic acid probe capable of specifically hybridizing with a unique sequence included within the sequence of a nucleic acid molecule encoding a human 9-cis-retinol dehydrogenase, wherein the sequence of a nucleic acid molecule encoding a human 9-cis-retinol dehydrogenase is labeled with a detectable marker; e) detecting labeled DNA fragments which have hybridized to the nucleic acid probe capable of specifically hybridizing with a unique sequence included within the sequence of a nucleic acid molecule encoding a human 9-cis-retinol dehydrogenase, wherein the sequence of a nucleic acid molecule encoding a human 9-cis-retinol dehydrogenase creates a unique band pattern specific to the DNA of subjects suffering from cancer; f) preparing DNA obtained from a sample of a subject for diagnosis by steps (a–e); and g) comparing the detected band pattern specific to the DNA obtained from a sample of subjects suffering from cancer or from the disease associated with either an overexpression or an underexpression of a human 9-cis-retinol dehydrogenase from step (e) and the DNA obtained from a sample of the subject for diagnosis from step (f) to determine whether the patterns are the same or different and to diagnose thereby predisposition to the cancer or the disease associated with the overexpression or the underexpression of the human 9-cis-retinol dehydrogenase if the patterns are the same.

This invention provides a method for detecting a predisposition to to a cancer or to a disease associated with an overexpression of a human 9-cis-retinol dehydrogenase in a sample from a subject which comprises: a) obtaining DNA from the sample of the subject suffering from cancer or from the disease associated with an overexpression of a human 9-cis-retinol dehydrogenase; b) performing a restriction digest of the DNA with a panel of restriction enzymes; c) separating the resulting DNA fragments by size fractionation; d) contacting the resulting DNA fragments with a nucleic acid probe capable of specifically hybridizing with a unique sequence included within the sequence of a nucleic acid molecule encoding a human 9-cis-retinol dehydrogenase, wherein the sequence of a nucleic acid molecule encoding a human 9-cis-retinol dehydrogenase is labeled with a detectable marker; e) detecting labeled DNA fragments which have hybridized to the nucleic acid probe capable of specifically hybridizing with a unique sequence included within the sequence of a nucleic acid molecule encoding a human 9-cis-retinol dehydrogenase, wherein the sequence of a nucleic acid molecule encoding a human 9-cis-retinol dehydrogenase creates a unique band pattern specific to the DNA of subjects suffering from cancer; f) preparing DNA obtained from a sample of a subject for diagnosis by steps (a–e) and g) comparing the detected band pattern specific to the DNA obtained from a sample of subjects suffering from the cancer or from the disease associated with the overexpression of a human 9-cis-retinol dehydrogenase from step (e) and the DNA obtained from a sample of the subject for diagnosis from step (f) to determine whether the patterns are the same or different and to diagnose thereby predisposition to the cancer or the disease associated with the overexpression of the human 9-cis-retinol dehydrogenase if the patterns are the same.

This invention provides a method for detecting a predisposition to to a cancer or to a disease associated with an underexpression of a human 9-cis-retinol dehydrogenase in a sample from a subject which comprises: a) obtaining DNA from the sample of the subject suffering from cancer or from the disease associated with an underexpression of a human 9-cis-retinol dehydrogenase; b) performing a restriction digest of the DNA with a panel of restriction enzymes; c) separating the resulting DNA fragments by size fractionation; d) contacting the resulting DNA fragments with a nucleic acid probe capable of specifically hybridizing with a unique sequence included within the sequence of a nucleic acid molecule encoding a human 9-cis-retinol dehydrogenase, wherein the sequence of a nucleic acid molecule encoding a human 9-cis-retinol dehydrogenase is labeled with a detectable marker; e) detecting labeled DNA fragments which have hybridized to the nucleic acid probe capable of specifically hybridizing with a unique sequence included within the sequence of a nucleic acid molecule encoding a human 9-cis-retinol dehydrogenase, wherein the sequence of a nucleic acid molecule encoding a human 9-cis-retinol dehydrogenase creates a unique band pattern specific to the DNA of subjects suffering from cancer; f) preparing DNA obtained from a sample of a subject for diagnosis by steps (a–e); and g) comparing the detected band pattern specific to the DNA obtained from a sample of subjects suffering from cancer or from the disease associated with the underexpression of a human 9-cis-retinol dehydrogenase from step (e) and the DNA obtained from a sample of the subject for diagnosis from step (f) to determine whether the patterns are the same or different and to diagnose thereby predisposition to the cancer or the disease associated with the underexpression of the human 9-cis-retinol dehydrogenase if the patterns are the same.

This invention provides a method for detecting a predisposition to a cancer or a disease associated with the overexpression or under expression of a human 9-cis-retinol dehydrogenase in a sample from a subject which comprises: a) obtaining RNA from the sample of the subject suffering from the cancer or the disease associated with the overexpression or under expression of the human 9-cis-retinol dehydrogenase; b) separating the RNA sample by size fractionation; c) contacting the resulting RNA species with a nucleic acid probe capable of specifically hybridizing with a unique sequence included within the sequence of a nucleic acid molecule encoding a human 9-cis-retinol dehydrogenase, wherein the sequence of a nucleic acid molecule encoding a human 9-cis-retinol dehydrogenase is labeled with a detectable marker; d) detecting labeled bands which have hybridized to the RNA species to create a unique band pattern specific to the RNA of subjects suffering from the cancer or the disease associated with the overexpression or under expression of the human 9-cis-retinol dehydrogenase; e) preparing RNA obtained from a sample of a subject for diagnosis by steps (a–d); and f) comparing the detected band pattern specific to the RNA obtained from a sample of subjects suffering from the cancer or the disease associated with the overexpression or under expression of a human 9-cis-retinol dehydrogenase from step (d) and the RNA obtained from a sample of the subject for diagnosis from step (f) to determine whether the patterns are the same or different and to diagnose thereby predisposition to the cancer or the disease associated with the overexpression or underexpression of the human 9-cis-retinol dehydrogenase if the patterns are the same.

This invention provides an antisense oligonucleotide having a sequence capable of specifically hybridizing to an mRNA molecule encoding a human 9-cis-retinol dehydrogenase so as to prevent expression of the mRNA molecule. In an embodiment the antisense oligonucleotide has a sequence capable of specifically hybridizing to the isolated cDNA molecule encoding a mammalian 9-cis-retinol dehydrogenase.

This invention provides a purified 9-cis-retinol dehydrogenase, wherein the 9-cis-retinol dehydrogenase is a human 9-cis-retinol dehydrogenase.

This invention provides an antibody directed to a purified 9-cis-retinol dehydrogenase or to a purified 9-cis-retinol dehydrogenase, wherein the 9-cis-retinol dehydrogenase is a human 9-cis-retinol dehydrogenase.

This invention provides an antibody capable of specifically recognizing 9-cis-retinol dehydrogenase. In an embodiment the antibody may be a polyclonal antibody. In another embodiment the antibody may be a monoclonal antibody.

This invention provides an antibody capable of specifically recognizing unique amino acid residues of 9-cis-retinol dehydrogenase. In a preferred embodiment of the antibody the unique amino acid residues of 9-cis-retinol dehydrogenase are HYGGAFLKYLKMQQRIMNLI (SEQ ID NO: 9).

This invention provides a method of detecting expression of a mammalian 9-cis-retinol dehydrogenase in a tissue or cells from a sample which comprises: a) incubating a sample of the tissue or cells from a sample with an antibody which specifically recognizes 9-cis-retinol dehydrogenase and is labeled with a detectable marker under conditions permitting a binding of the antibody to the tissue or the cells; and b) detecting labeled tissue or cells, thereby detecting expression of the mammalian 9-cis-retinol dehydrogenase in the tissue or the cells.

This invention provides a method of detecting human 9-cis-retinol dehydrogenase in a sample which comprises: a) contacting the sample with of any of the above-described antibodies under conditions permitting the formation of a complex between the antibody and the human 9-cis-retinol dehydrogenase in the sample; and b) detecting the complex formed in step (a) thereby detecting the presence of human 9-cis-retinol dehydrogenase in the sample.

This invention provides a method of detecting a disease which is responsive to treatment with a retinoid, comprising the method of detecting human 9-cis-retinol dehydrogenase in a tissue or cells from a sample, wherein the detection of the expression of the mammalian 9-cis-retinol dehydrogenase indicates the disease is responsive to retinoic acid treatment.

This invention provides a method of detecting a disease which is refractory to treatment with a retinoid comprising the method of detecting human 9-cis-retinol dehydrogenase in a tissue or cells from a sample, wherein the detection of the expression of the mammalian 9-cis-retinol dehydrogenase indicates the disease is refractory to retinoic acid treatment.

This invention provides a pharmaceutical composition comprising an amount of any of the above-described oligonucleotides and effective to prevent overexpression of a human 9-cis-retinol dehydrogenase and a pharmaceutically acceptable carrier capable of passing through a cell membrane.

This invention provides a recombinant non-human vertebrate animal wherein the functional 9-cis-retinol dehydrogenase is not expressed.

This invention provides a recombinant non-human vertebrate animal wherein the functional 9-cis-retinol dehydrogenase is underexpressed.

This invention provides a method of treating any of the above-described recombinant non-human vertebrate animals comprising administration of a vector comprising an isolated mammalian nucleic acid molecule encoding a 9-cis-retinol dehydrogenase.

BRIEF DESCRIPTION OF THE FIGURES

FIGS. 1A–1B. FIG. 1A, the nucleotide sequence for the cDNA clone encoding 9cRDH. The start and termination codons for the cDNA sequence of 9cRDH are underlined. FIG. 1B, the deduced amino acid sequence for the protein encoded by the cDNA clone obtained from a normalized human breast tissue library (9c) and, for comparison, the amino acid sequences for bovine 11cis-retinol dehydrogenase (11) (27), rat liver retinol dehydrogenase, type I (L1) (11), and rat liver retinol dehydrogenase, type II (L2) (13). Amino acids that are identical in each of the four protein sequences are underlined.

In FIG. 2D, 10, µM 9-cis-retinol was incubated with 38 µg of CHO cell homogenate protein obtained from cells transfected with vector alone and 2 mM NAD+. The elution positions of 13-cis-retinaldehyde (1), 9-cis-retinaldehyde (2), all-trans-retinaldehyde (3), 13-cis-retinol (4), 9-cis-retinol (5), and alltrans-retinol (6) are indicated with arrows.

FIGS. 4A–4G. Sequence analysis of full-length cDNA clones for mouse 9-cis retinol dehydrogenase obtained from kidney (NMKT7.SEQ), liver (NMLRDH. SEQ), and testis (PCRD4.SEQ) cDNA libraries. Alignment using cluster method with weighted residue weight table. X is a space, i.e. no nucleotide.

FIG. 5. Immunoblot analysis for 9cRDH expression in 11-week old human fetal tissues. Equal protein loads from cell homogenates of CHO cells transfected with a cDNA for human 9cRDH (h9cRDH), with a cDNA for mouse 9cRDH (m9cRDH) or with the vector alone (Sham) were employed as controls for this analysis. First trimester (week 11) human fetal tissue pools examined consist of adrenals and small intestine (A+I), kidney and brain (k+B) and small intestine, brain and lung (I+B+Lu.). Tissues and immunoblots were processed exactly as described in "Experimental Procudures".

FIG. 6. FIG. 6A. Exon-intron organization of mouse 9cRDH gene. The sizes of the five exons are: Exon 1, 167 bp; exon 2, 342 bp; exon 3, 259 bp; exon 4, 164 bp; and exon 5, 349 bp. The sizes of the four introns are: intron 1, 554 bp; intron 2, 114 bp; intron 3, 3.5 kb; and the intron 4, 198 bp. FIG. 6B. Exon-intron organization of human 11cRDH gene. The size of exon 2, exon 3 and exon 4 are exactly same between mouse 9cRDH and human 11cRDH. FIG. 6C. Mouse 9cRDH cDNAs. The liver clone of 1281 bp aligned to the mouse 9cRDH gene. It appeared to be spliced normally according to the AG/GU rule. As compared to the liver clone, the kidney clone has 5 bp of intron 1 that is unspliced. Testis clone 1 has 58 bp of intron 3 and 222 bp of intron 1 that are unspliced; testis clone 2 has 340 bp of unspliced intron 3 and did not reach exon 3; testis clone 3 did not contain any intron sequences and was identical to the liver clone but was missing the translation initiation codon.

FIG. 8. In situ hybridization localization of 9cRDH in day 12.5 embryos. FIG. 8A. Sagittal section showing 9cRDH expression in the floor of the fourth ventricle. FIG. 8B. Transverse section through the thoracic region revealed that 9cRDH was expressed in the roof plate of the neural tube. Abbreviations: IV V—fourth ventricle; MO—medula oblongata; R—roof of the forth ventricle; CC—central canal; RP—roof plate of neural tube.

FIG. 10. Chromosome mapping of mouse 9cRDH gene. FIG. 10A. Map figures from The Jackson BSB and BSS backcrosses showing part of Chromosome 10. The maps are depicted with the centromeres toward the top. A 3 cM scale bar is shown to the right of the figures. There are large portions of the chromosome not shown, as indicated by the dashed lines. Loci mapping to the same position are listed in alphabetical order. Missing typings were inferred from surrounding data where assignment was unambiguous. FIG. 10B. Haplotype figure from the combined data of The Jackson BSB and BSS backcross showing part of Chromosome 10 with loci linked to 9cRDH. Loci are listed in order with the most proximal at the top. The black boxes represent the C57BL6/JEi allele and the white boxes the SPRET/Ei allele. The number of animals with each haplotype is given at the bottom of each column of boxes. The percent recombination (R) between adjacent loci is given to the right of the figure, with the standard error (SE) for each R. Raw data from The Jackson Laboratory can be obtained from the World Wide Web address http://www.jax.org/resources/documents/cmd atas.

DETAILED DESCRIPTION OF THE INVENTION

Figure 2A:
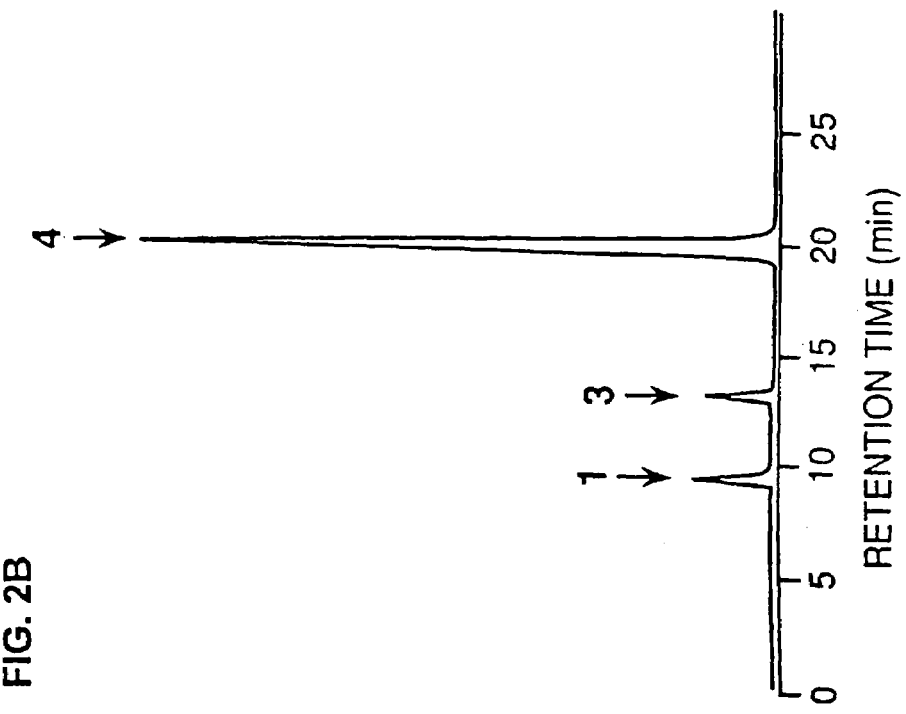
FIGS. 2A–2D. Representative HPLC profiles for extracts of incubation mixtures consisting of 10 µM 9-cis-retinol (FIG. 2A), 10 µM 13-cis-retinol (FIG. 2B), or 10 µM all-trans-retinol (FIG. 2C) and 32 µg of CHO cell homogenate protein obtained from cells transfected with vector (pcDNA3, Invitrogen) containing the cDNA insert and 2 mM NAD+.
Figure 2B:
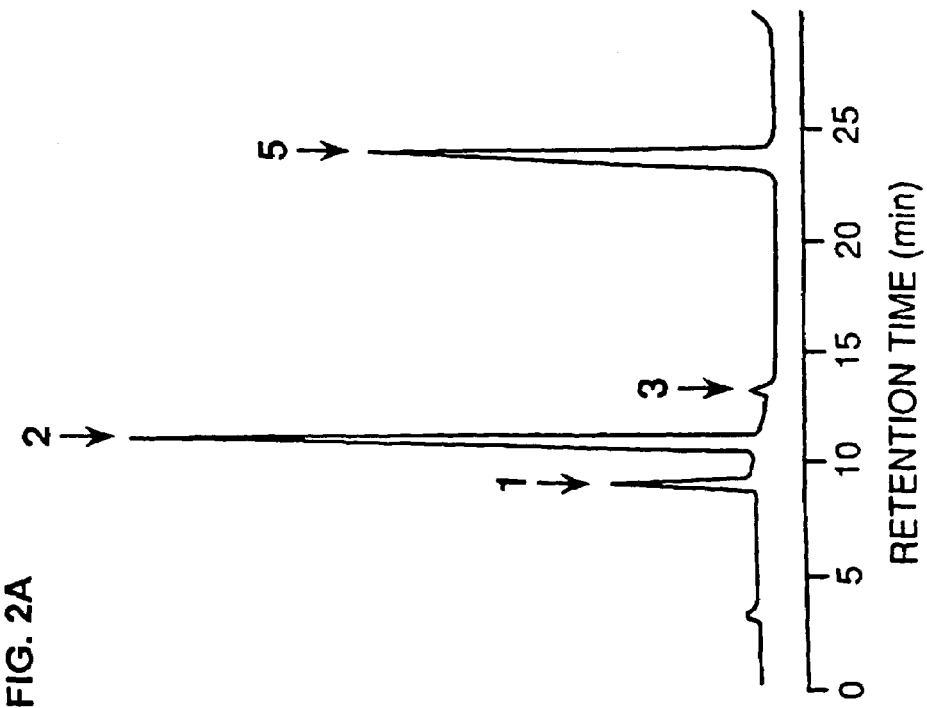
Figure 2D:
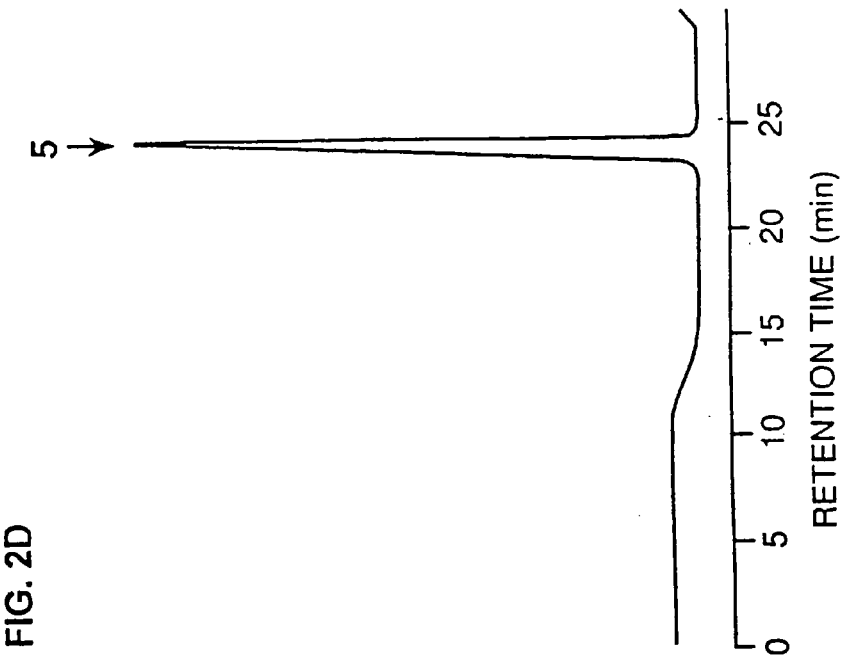
Figure 2C:
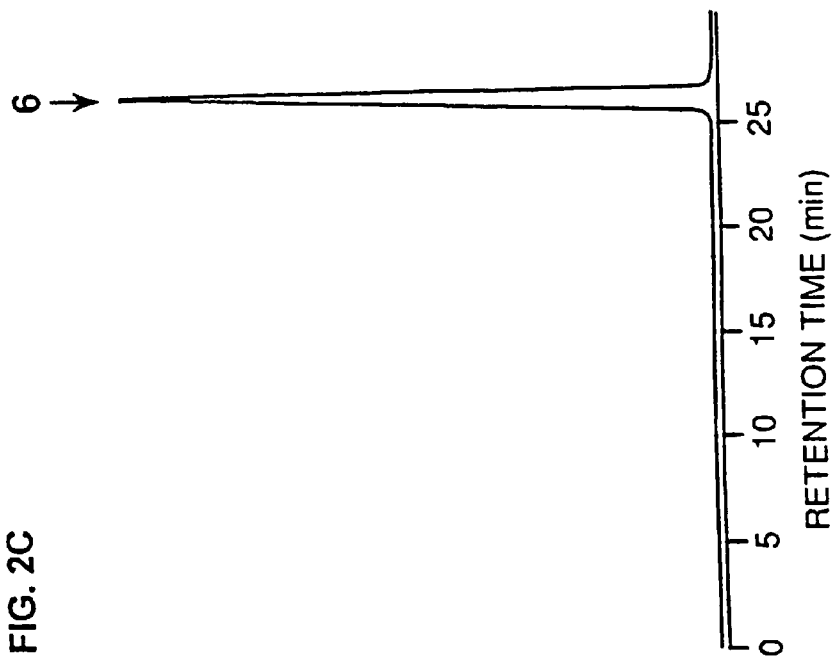

The following standard abbreviations are used throughout the specification to indicate specific nucleotides:
C=cytosine A=adenosine
T=thymidine G=guanosine This invention provides an isolated nucleic acid molecule encoding a mammalian 9-cis-retinol dehydrogenase. In an embodiment the isolated nucleic acid molecule is a DNA molecule. In another embodiment the isolated DNA molecule is a full-length DNA molecule. In an embodiment the isolated DNA molecule is a cDNA molecule. In a preferred embodiment the cDNA molecule encodes a human 9-cis-retinol dehydrogenase. In an embodiment the cDNA molecule encodes a mouse 9-cis-retinol dehydrogenase. In another preferred embodiment the isolated nucleic acid molecule has the nucleotide sequence shown in FIG. 1A (SEQ. ID NO: 1). In another embodiment the isolated nucleic acid molecule has the nucleotide sequence shown in SEQ. ID NO: 6. In yet another embodiment the isolated nucleic acid molecule has the nucleotide sequence shown in SEQ. ID NO: 7. In still another embodiment the isolated nucleic acid molecule has the nucleotide sequence shown in SEQ. ID NO: 8. In a preferred embodiment of the isolated nucleic acid molecule, the encoded 9-cis-retinol dehydrogenase catalyzes oxidation of 9-cis-retinol. In another preferred embodiment of the isolated nucleic acid molecule, the encoded 9-cis-retinol dehydrogenase catalyzes oxidation of 13-cis-retinol. In still another embodiment the isolated DNA molecule is genomic DNA molecule. In another embodiment the isolated nucleic acid molecule is an RNA molecule.

The DNA molecules of the subject invention also include DNA molecules coding for polypeptide analogs, fragments or derivatives of antigenic polypeptides which differ from naturally-occurring forms in terms of the identity or location of one or more amino acid residues (deletion analogs containing less than all of the residues specified for the protein, substitution analogs wherein one or more residues specified are replaced by other residues and addition analogs where in one or more amino acid residues is added to a terminal or medial portion of the polypeptides) and which share some or all properties of naturally-occurring forms. These molecules include: the incorporation of codons "preferred" for expression by selected non-mammalian hosts; the provision of sites for cleavage by restriction endonuclease enzymes; and the provision of additional initial, terminal or intermediate DNA sequences that facilitate construction of readily expressed vectors.

The DNA molecules described and claimed herein are useful for the information which they provide concerning the amino acid sequence of the polypeptide, 9-cis-retinol dehydrogenase, and as products for the large scale synthesis of the polypeptide (9-cis-retinol dehydrogenase) by a variety of recombinant techniques. The molecule is useful for generating new cloning and expression vectors, transformed and transfected prokaryotic and eukaryotic host cells, and new and useful methods for cultured growth of such host cells capable of expression of the polypeptide (9-cis-retinol dehydrogenase) and related products.

This invention provides a purified 9-cis-retinol dehydrogenase. In an embodiment a 9-cis-retinol dehydrogenase is encoded by the isolated nucleic acid molecule encoding a mammalian 9-cis-retinol dehydrogenase. In a preferred embodiment the 9-cis-retinol dehydrogenase has substantially the same amino acid sequence as shown in FIG. 1B (SEQ. ID NO: 2). In another preferred embodiment the 9-cis-retinol dehydrogenase of claim 16, wherein the 9-cis-retinol dehydrogenase has the amino acid sequence as shown in FIG. 1B (SEQ. ID NO: 2). In yet another preferred embodiment of the 9-cis-retinol dehydrogenase which may be a purified 9-cis-retinol dehydrogenase, a purified 9-cis-retinol dehydrogenase encoded by the isolated nucleic acid molecule encoding a mammalian 9-cis-retinol dehydrogenase, said purified 9-cis-retinol dehydrogenase having substantially the same amino acid sequence as shown in FIG. 1B (SEQ. ID NO: 2) or said purified 9-cis-retinol dehydrogenase having the amino acid sequence as shown in FIG. 1B (SEQ. ID NO: 2), the 9-cis-retinol dehydrogenase is a human 9-cis-retinol dehydrogenase. In another embodiment of the 9-cis-retinol dehydrogenase which may be a purified 9-cis-retinol dehydrogenase or a purified 9-cis-retinol dehydrogenase encoded by the isolated nucleic acid molecule encoding a mammalian 9-cis-retinol dehydrogenase, the 9-cis-retinol dehydrogenase is a mouse 9-cis-retinol dehydrogenase.

This invention provides a mouse 9-cis-retinol dehydrogenase, wherein the nucleic acid molecule encoding the 9-cis-retinol dehydrogenase has the nucleotide sequence shown in any of SEQ. ID NOS: 6, 7, and 8.

This invention provides an isolated nucleic acid molecule of claim 1 operatively linked to a promoter of RNA transcription.

This invention also provides a vector comprising the isolated mammalian nucleic acid molecule encoding a mammalian 9-cis-retinol dehydrogenase. In an embodiment the vector is a plasmid.

In an embodiment, a full-length cDNA nucleic acid molecule encoding a human 9-cis-retinol dehydrogenase is inserted by EcoR1/Not1 into a pcDNA3 plasmid (Invitrogen®) and the resulting plasmid is designated as pcDNA3-1. Plasmid pcDNA3-1 was deposited on Sep. 19, 1997 with the American Type Culture Collection (ATCC), 12301 Parklawn Drive, Rockville, Md. 20852, U.S.A. under the provisions of the Budapest Treaty for the International Recognition of the Deposit of Microorganisms for the Purposes of Patent Procedure. Plasmid pcDNA3-1 was accorded ATCC Accession Number 209285.

Numerous vectors for expressing the inventive proteins may be employed. Such vectors, including plasmid vectors, cosmid vectors, bacteriophage vectors and other viruses, are well known in the art. For example, one class of vectors utilizes DNA elements which are derived from animal viruses such as bovine papilloma virus, polyoma virus, adenovirus, vaccinia virus, baculovirus, retroviruses (RSV, MMTV or MoMLV), Semliki Forest virus or SV40 virus. Additionally, cells which have stably integrated the DNA into their chromosomes may be selected by introducing one or more markers which allow for the selection of transfected host cells. The markers may provide, for example, prototrophy to an auxotrophic host, biocide resistance or resistance to heavy metals such as copper. The selectable marker gene can be either directly linked to the DNA sequences to be expressed, or introduced into the same cell by cotransformation.

Regulatory elements required for expression include promoter sequences to bind RNA polymerase and transcription initiation sequences for ribosome binding. Additional elements may also be needed for optimal synthesis of mRNA. These additional elements may include splice signals, as well as enhancers and termination signals. For example, a bacterial expression vector includes a promoter such as the lac promoter and for transcription initiation the Shine-Dalgarno sequence and the start codon AUG. Similarly, a eukaryotic expression vector includes a heterologous or homologous promoter for RNA polymerase II, a downstream polyadenylation signal, the start codon AUG, and a termination codon for detachment of the ribosome. Such vectors may be obtained commercially or assembled from the sequences described by methods well known in the art, for example the methods described above for constructing vectors in general.

These vectors may be introduced into a suitable host cell to form a host vector system for producing the inventive proteins. Methods of making host vector systems are well known to those skilled in the art.

Suitable host cells include, but are not limited to, bacterial cells (including gram positive cells), yeast cells, fungal cells, insect cells and animal cells. Suitable animal cells include, but are not limited to HeLa cells, Cos cells, CV1 cells and various primary mammalian cells. Numerous mammalian cells may be used as hosts, including, but not limited to, the mouse fibroblast cell NIH-3T3 cells, CHO cells, HeLa cells, Ltk$^-$ cells and COS cells. Mammalian cells may be transfected by methods well known in the art such as calcium phosphate precipitation, electroporation and microinjection.

One of ordinary skill in the art will easily obtain unique sequences from the cDNA cloned in the pcDNA3-1 plasmid. Such unique sequences may be used as probes to screen various mammalian cDNA libraries and genomic DNAs, e.g. mouse, rat and bovine, to obtain homologous nucleic acid sequences and to screen different cDNA tissue libraries to obtain isoforms of the obtained nucleic acid sequences. Nucleic acid probes from the cDNA cloned in the pcDNA3-1 plasmid may further be used to screen other human tissue cDNA libraries to obtain isoforms of the nucleic acid sequences encoding 9-cis-retinol dehydrogenase as well as to screen human genomic DNA to obtain the analogous nucleic acid sequences. The homologous nucleic acid sequences and isoforms may be used to produce the proteins encoded thereby.

In an embodiment, a full-length cDNA nucleic acid molecule encoding a mouse liver 9-cis-retinol dehydrogenase is inserted by EcoR1/Not1 into a pcDNA3 plasmid (Invitrogen®) and the resulting plasmid is designated as pcDNA3-2.

In an embodiment, a full-length cDNA nucleic acid molecule encoding a mouse kidney 9-cis-retinol dehydrogenase is inserted by EcoR1/Not1 into a pcDNA3 plasmid (Invitrogen®) and the resulting plasmid is designated as pcDNA3-3.

In an embodiment, a full-length cDNA nucleic acid molecule encoding a mouse testis 9-cis-retinol dehydrogenase is inserted by EcoR1/Not1 into a pcDNA3 plasmid (Invitrogen®) and the resulting plasmid is designated as pcDNA3-4. In further embodiments the vector comprising any of the plasmids designated as pcDNA3-1, pcDNA3-2, pcDNA3-3, or pcDNA3-4 may be introduced into a suitable host cell. In still further embodiments the host cell is selected from a group consisting of a bacterial cell, a plant cell, and insect cell and a mammalian cell.

This invention provides a method of producing a polypeptide having the biological activity of a mammalian 9-cis-retinol dehydrogenase which comprises growing any of the above described host cells of a vector containing the nucleic acid molecule encoding a mammalian 9-cis-retinol dehydrogenase under suitable conditions permitting production of the polypeptide and recovering the polypeptide so produced.

As used herein, the biological activity of a 9-cis-retinol dehydrogenase is defined as the ability to catalyze oxidation of retinol to retinaldehyde, as well as the ability to catalyze the reverse reaction, i.e. reduction of retinaldehyde to retinol. Accordingly, a 9-cis-retinol dehydrogenase may also be defined as a "retinaldehyde reductase", i.e. a 9-cis-retinaldehyde reductase.

This invention provides a nucleic acid probe comprising a nucleic acid molecule of at least 15 nucleotides capable of specifically hybridizing with a unique sequence included within the sequence of an isolated nucleic acid molecule encoding a mammalian 9-cis-retinol dehydrogenase. In an embodiment of the nucleic acid probe the nucleic acid molecule is DNA. In another embodiment of the nucleic acid probe the nucleic acid molecule is RNA.

This invention provides a nucleic acid probe comprising a nucleic acid molecule of at least 15 nucleotides which is complementary to a sequence of the isolated nucleic acid molecule encoding a mammalian 9-cis-retinol dehydrogenase.

In an embodiment of the nucleic acid probe the nucleic acid molecule is DNA. In another embodiment of the nucleic acid probe the nucleic acid molecule is RNA. In further embodiment any of the above described nucleic acid probes may be labeled with a detectable marker. In an embodiment of these nucleic acid probes the detectable marker may be selected from the group consisting of a radioactive isotope, enzyme, dye, biotin, a fluorescent label or a chemiluminescent label.

This invention provides a method of detecting expression of a mammalian 9-cis-retinol dehydrogenase in a cell which comprises: a) incubating a sample of cells with a retinal and an electron acceptor under conditions permitting oxidation of retinol to retinaldehyde; b) separating the resulting retinol and the retinaldehyde; and c) determining the quantities of the retinol and the retinaldehyde separated in step (b), thereby detecting expression of a mammalian 9-cis-retinol dehydrogenase in the cell. In an embodiment of this method, the retinol in step (a) is selected from the group consisting of 9-cis-retinol, 11-cis-retinol, and 13-cis-retinol. In a further embodiment of this method, the electron acceptor in step (a) is selected from the either NAD$^+$ or NADP$^+$.

This invention provides a method of detecting expression of a mammalian 9-cis-retinol dehydrogenase in a tissue which comprises: a) isolating total mRNA from a sample of the tissue; b) contacting the total mRNA with a nucleic acid probe capable of specifically hybridizing with a unique sequence included within the sequence of a nucleic acid molecule encoding a mammalian 9-cis-retinol dehydrogenase, wherein the sequence of a nucleic acid molecule encoding a mammalian 9-cis-retinol dehydrogenase is labeled with a detectable marker, under hybridizing conditions; and c) detecting the presence of mRNA which has hybridized to the nucleic acid probe capable of specifically hybridizing with a unique sequence included within the sequence of a nucleic acid molecule encoding a mammalian 9-cis-retinol dehydrogenase, thereby detecting expression of a mammalian 9-cis-retinol dehydrogenase in the tissue.

This invention further provides a method of detecting an compound capable of inhibiting a 9-cis-retinol dehydrogenase which comprises: a) incubating a 9-cis-retinol dehydrogenase and an electron acceptor under conditions permitting oxidation of a retinol to a retinaldehyde; b) separating the resulting retinol and the retinaldehyde produced in step (a); c) incubating a compound capable of inhibiting a 9-cis-retinol dehydrogenase with a 9-cis-retinol dehydrogenase and an electron acceptor under conditions permitting inhibition of oxidation of a retinol to a retinaldehyde, the 9-cis-retinol dehydrogenase and the electron acceptor being the same 9-cis-retinol dehydrogenase and the same electron acceptor incubated in step (a); d) separating the resulting retinol and the retinaldehyde produced in step (c); e) determining the quantities of the retinol and the retinaldehyde separated in steps (b) and (d), respectively, a smaller quantity of retinaldehyde and a greater quantity of retinol determined in step (d) indicating an inhibition of 9-cis-retinol dehydrogenase activity; f) comparing the amount of inhibition of 9-cis-retinol dehydrogenase activity in step (d) with the amount of retinaldehyde and retinol resulting in step (b), a 50% inhibition of oxidation of retinol to retinaldehyde in step (d) indicating that the compound is capable of inhibiting the 9-cis-retinol dehydrogenase.

In a preferred embodiment of this method, the compound capable of inhibiting a 9-cis-retinol dehydrogenase is selected from the group consisting of naturally occurring and synthetic retinoids and lipids. In another preferred embodiment the retinoids are selected from the group consisting of naturally occurring and synthetic retinoic acids and synthetic retinoic acid analogs. The retinoids include but are not limited to 13-cis retinoic acid, 9-cis retinoic acid, and lipids with chemical structures similar to 13-cis retinoic acid, e.g. oleic acid. One of skill in the art would know how to select compounds with structures similar to these or other retinoids for use in an assay(s) to determine the above described inhibition.

This invention provides a method of detecting an compound capable of inhibiting a 9-cis-retinol dehydrogenase in vitro, comprising: a) incubating a sample of cells with retinol and an electron acceptor under conditions permitting oxidation of retinol to retinaldehyde; b) separating the resulting retinol and the retinaldehyde produced in step (a); c) incubating a sample of cells, the cells being the same type of cells as the cells incubated in step (a), with a compound capable of inhibiting a 9-cis-retinol dehydrogenase under conditions permitting inhibition of oxidation of retinol to retinaldehyde; d) separating the resulting retinol and the retinaldehyde produced in step (c); e) determining the quantities of the retinol and the retinaldehyde separated in steps (b) and (d), respectively, a smaller quantity of retinaldehyde and a greater quantity of retinol determined in step (d) indicating an inhibition of 9-cis-retinol dehydrogenase activity; f) comparing the amount of inhibition of 9-cis-retinol dehydrogenase activity in step (d) with the amount of retinaldehyde and retinol resulting in step (b), a 50% inhibition of oxidation of retinol to retinaldehyde in step (d) indicating that the compound is capable of inhibiting the 9-cis-retinol dehydrogenase in vitro.

In a preferred embodiment of this method, the compound capable of inhibiting a 9-cis-retinol dehydrogenase is selected from the group consisting of naturally occurring and synthetic retinoids and lipids. In another preferred embodiment the retinoids are selected from the group consisting of naturally occurring and synthetic retinoic acids and synthetic retinoic acid analogs. The retinoids include but are not limited to 13-cis retinoic acid, 9-cis retinoic acid, and lipids with chemical structures similar to 13-cis retinoic acid, e.g. oleic acid. One of skill in the art would know how to select compounds with structures similar to these or other retinoids for use in an assay(s) to determine the above described inhibition.

This invention provides a method of detecting an compound capable of inhibiting a 9-cis-retinol dehydrogenase in vivo, comprising: a) administering a suitable dose of a compound capable of inhibiting a 9-cis-retinol dehydrogenase to a mammal; b) detecting in a tissue sample from the mammal in step (a) a presence of a retinol and a retinaldehyde; c) detecting in a tissue sample from a second mammal a presence of a retinol and a retinaldehyde; d) determining the quantities of the retinol and the retinaldehyde detected in steps (b) and (c), respectively, a smaller quantity of retinaldehyde and a greater quantity of retinol determined in step (b) indicating an inhibition of 9-cis-retinol dehydrogenase activity; e) determining the amount of inhibition of 9-cis-retinol dehydrogenase activity in step (d), a 50% inhibition of 9-cis-retinol dehydrogenase activity indicating that the compound is capable of inhibiting the 9-cis-retinol dehydrogenase in vivo.

In a preferred embodiment of this method, the compound capable of inhibiting a 9-cis-retinol dehydrogenase is selected from the group consisting of naturally occurring and synthetic retinoids and lipids. In another preferred embodiment the retinoids are selected from the group consisting of naturally occurring and synthetic retinoic acids and synthetic retinoic acid analogs. The retinoids include but are not limited to 13-cis retinoic acid, 9-cis retinoic acid, and lipids with chemical structures similar to 13-cis retinoic acid, e.g. oleic acid. One of skill in the art would know how to select compounds with structures similar to these or other retinoids for use in an assay(s) to determine the above described inhibition.

This invention provides a method of detecting an compound capable of inhibiting a 9-cis-retinol dehydrogenase which comprises: a) incubating a 9-cis-retinol dehydrogenase and an electron donor under conditions permitting reduction of a retinaldehyde to a retinol; b) separating the resulting retinol and the retinaldehyde produced in step (a); c) incubating a compound capable of inhibiting a 9-cis-retinol dehydrogenase with a 9-cis-retinol dehydrogenase and an electron donor under conditions permitting reduction of a retinaldehyde to a retinol, the 9-cis-retinol dehydrogenase and the electron donor being the same 9-cis-retinol dehydrogenase and the same electron donor incubated in step (a); d) separating the resulting retinol and the retinaldehyde produced in step (c); e) determining the quantities of the retinol and the retinaldehyde separated in steps (b) and (d), respectively, a larger quantity of retinaldehyde and a smaller quantity of retinol determined in step (d) indicating an inhibition of 9-cis-retinol dehydrogenase activity; f) determining the amount of inhibition of 9-cis-retinol dehydrogenase activity in step (e), a 50% inhibition of reduction of retinaldehyde to retinol indicating that the compound is capable of inhibiting the 9-cis-retinol dehydrogenase. In a preferred embodiment of this method, the compound capable of inhibiting a 9-cis-retinol dehydrogenase is selected from the group consisting of naturally occurring and synthetic retinoids and lipids. In another preferred embodiment the retinoids are selected from the group consisting of naturally occurring and synthetic retinoic acids and synthetic retinoic acid analogs. The retinoids include but are not limited to 13-cis retinoic acid, 9-cis retinoic acid, and lipids with chemical structures similar to 13-cis retinoic acid, e.g. oleic acid. One of skill in the art would know how to select compounds with structures similar to these or other retinoids for use in an assay(s) to determine the above described inhibition.

This invention provides a method of detecting an compound capable of inhibiting a 9-cis-retinol dehydrogenase in vitro, comprising: a) incubating a sample of cells with retinol and an electron donor under conditions permitting reduction of a retinaldehyde to a retinol; b) separating the resulting retinol and the retinaldehyde produced in step (a); c) incubating a sample of cells, the cells being the same type of cells as the cells incubated in step (a), with a compound capable of inhibiting a 9-cis-retinol dehydrogenase under conditions permitting reduction of a retinaldehyde to a retinol, the 9-cis-retinol dehydrogenase and the electron donor being the same 9-cis-retinol dehydrogenase and the same electron donor incubated in step (a); d) separating the resulting retinol and the retinaldehyde produced in step (c); e) determining the quantities of the retinol and the retinaldehyde separated in steps (b) and (d), respectively, a larger quantity of retinaldehyde and a smaller quantity of retinol determined in step (d) indicating an inhibition of 9-cis-retinol dehydrogenase activity; f) determining the amount of inhibition of 9-cis-retinol dehydrogenase activity in step (e), a 50% inhibition of reduction of retinaldehyde to retinol indicating that the compound is capable of inhibiting the 9-cis-retinol dehydrogenase in vitro.

In a preferred embodiment of this method, the compound capable of inhibiting a 9-cis-retinol dehydrogenase is selected from the group consisting of naturally occurring and synthetic retinoids and lipids. In another preferred embodiment the retinoids are selected from the group consisting of naturally occurring and synthetic retinoic acids and synthetic retinoic acid analogs. The retinoids include but are not limited to 13-cis retinoic acid, 9-cis retinoic acid, and lipids with chemical structures similar to 13-cis retinoic acid, e.g. oleic acid. One of skill in the art would know how to select compounds with structures similar to these or other retinoids for use in an assay(s) to determine the above described inhibition.

This invention provides a method of detecting an compound capable of inhibiting a 9-cis-retinol dehydrogenase in vivo, comprising: a) administering a suitable dose of a compound capable of inhibiting a 9-cis-retinol dehydrogenase to a mammal; b) detecting in a tissue sample from the mammal in step (a) a presence of a retinol and a retinaldehyde; c) detecting in a tissue sample from a second mammal a presence of a retinol and a retinaldehyde; d) determining the quantities of the retinol and the retinaldehyde detected in steps (b) and (c), respectively, a larger quantity of retinaldehyde and a smaller quantity of retinol determined in step (b) indicating an inhibition of 9-cis-retinol dehydrogenase activity; e) determining the amount of inhibition of 9-cis-retinol dehydrogenase activity in step (d), a 50% inhibition of 9-cis-retinol dehydrogenase activity indicating that the compound is capable of inhibiting the 9-cis-retinol dehydrogenase in vivo.

In a preferred embodiment of this method, the compound capable of inhibiting a 9-cis-retinol dehydrogenase is selected from the group consisting of naturally occurring and synthetic retinoids and lipids. In another preferred embodiment the retinoids are selected from the group consisting of naturally occurring and synthetic retinoic acids and synthetic retinoic acid analogs. The retinoids include but are not limited to 13-cis retinoic acid, 9-cis retinoic acid, and lipids with chemical structures similar to 13-cis retinoic acid, e.g. oleic acid. One of skill in the art would know how to select compounds with structures similar to these or other retinoids for use in an assay(s) to determine the above described inhibition. Accordingly, the above-described methods may be used to screen compounds with chemical structures similar to but not limited to 13-cis retinoic acid (e.g. synthetic or naturally occurring retinoids or analogs thereof which inhibit a 9-cis-retinol dehydrogenase) so as to "screen out" drugs which have teratogenic effects. The inhibition of 9-cis-retinol dehydrogenase by the screened compounds having chemical structures similar to but not limited to 13-cis retinoic acid would thus be an indicator of an adverse effect of the compounds. Such a screen detecting inhibition of 9-cis-retinol dehydrogenase would indicate that these inhibitory drugs (compounds having chemical structures similar to but not limited to 13-cis retinoic acid) may have a teratogenic effect and the use of these compounds as an alternative treatment (e.g. for acne or cancer treatment) to 13-cis retinoic acid (or analogs or derivatives thereof) would be a negated, i.e. drugs which have teratogenic effects wouild be "screened out" (not chosen) as alternative drugs to 13-cis retinoic acid or analogs or derivatives thereof. This invention also provides a method of determining a toxic compound capable of inhibiting a 9-cis-retinol dehydrogenase comprising the method of any of the above-described methods of detecting an compound capable of inhibiting a 9-cis-retinol dehydrogenase, wherein an ability of a small concentration of the compound to inhibiting 50% of the 9-cis-retinol dehydrogenase activity indicates that the compound is toxic.

The above-described methods may be used to develop, e.g. synthesize new or improved drugs, e.g. less toxic retinoids, or more specific drugs, e.g. retinoids binding to or interacting with particular retinoid receptors, e.g. such as all-trans retinoic acid which binds to or interacts with retinoic acid receptors (RARs), or 9-cis retinoic acid which binds to or interacts with retinoid X receptors (RXRs). RARs regulate retinoid responsive genes. RXRs regulate retinoid, thyroid hormone, vitamn D, proxisomal proliferator and other responsive genes. Accordingly, above-described screening methods may be used to develop new or improved drugs relating to any regulatory aspects of retinoids, e.g. the gene expression or at the receptor(s) ligand binding site(s) for enhancing interaction or stimulating interaction between ligands and receptors.

The above-described methods may be used to develop synthetic inhibitors (or regulators) of the 9-cis-retinol dehydrogenase or 13-cis-retinol dehydrogenase based on the interaction of the 9-cis-retinol dehydrogenase or 13-cis-retinol dehydrogenase and their respective substrates and the determination of their lower toxicity (as compared to the highly toxic compounds screened supra) so as to produce drugs which are therapeutic. Moreover, new drugs may be developed which regulate the pathway of the 9-cis-retinol dehydrogenase or 13-cis-retinol dehydrogenase, e.g. biological activities catalyzed thereby.

The new or improved drugs, include but are not limited to retinoids, and may be used to treat a variety of diseases, including but not limited to dermatologic conditions such as acne or psoriasis, diabetes or lipid disorders indiabetes, for blocking collagenase production in arthritis, for pulmonary diseases such as asthma, and for chemoprevention induction (lessening the toxicity of chemotherapy) and continuation of remission in the treatment of cancer. One of skill in the art will appreciate the many applications of new or improved drugs such as retinoids.

The above-described methods may be used to determine the toxicity of compounds other than retinoids. In an embodiment the compounds may be steroids. Accordingly, any of the above-described methods for detecting a compound capable of inhibiting a 9-cis-retinol dehydrogenase in vitro or in vivo may be used to detect an inhibition of a 9-cis-retinol dehydrogenase by a steroid. In another embodiment, of any the above-described methods, an ability of a small concentration of a steroid to inhibit 50% of the 9-cis-retinol dehydrogenase activity indicates that the steroid is toxic.

In an embodiment of the above-described for determining a toxic compound, the method may be used for screening for a potential therapeutic compound, wherein the 50% inhibition of a 9-cis-retinol dehydrogenase by a small concentration of several compounds is compared to determine the respective toxicities of the compounds, a determination of a higher toxicity by a smaller concentration of a compound indicating that the compound is not a potential therapeutic compound.

This invention provides a method for detecting a predisposition to cancer associated with the expression of a 9-cis-retinol dehydrogenase in a sample from a subject which comprises: a) determining the amount of expression of a 9-cis-retinol dehydrogenase in a cancerous tissue by performing the method of either of claims 40 and 43 on a sample of cells from the cancerous tissue; b) determining the amount of expression of a 9-cis-retinol dehydrogenase in a sample from a subject; and c) comparing the level of expression of 9-cis-retinol dehydrogenase in the sample from the subject with the level of expression of 9-cis-retinol dehydrogenase in the sample from the cancerous tissue, a comparable level of expression of 9-cis-retinol dehydrogenase indicating a predisposition to cancer in the subject.

As used herein a subject may be any animal, preferably a mammal, and most preferably a human.

This invention provides a method for detecting a predisposition to to a cancer or to a disease associated with the either an overexpression or an underexpression of a human 9-cis-retinol dehydrogenase in a sample from a subject which comprises: a) obtaining DNA from the sample of the subject suffering from cancer or from the disease associated with either an overexpression or an underexpression of a human 9-cis-retinol dehydrogenase; b) performing a restriction digest of the DNA with a panel of restriction enzymes; c) separating the resulting DNA fragments by size fractionation; d) contacting the resulting DNA fragments with a nucleic acid probe capable of specifically hybridizing with a unique sequence included within the sequence of a nucleic acid molecule encoding a human 9-cis-retinol dehydrogenase, wherein the sequence of a nucleic acid molecule encoding a human 9-cis-retinol dehydrogenase is labeled with a detectable marker; e) detecting labeled DNA fragments which have hybridized to the nucleic acid probe capable of specifically hybridizing with a unique sequence included within the sequence of a nucleic acid molecule encoding a human 9-cis-retinol dehydrogenase, wherein the sequence of a nucleic acid molecule encoding a human 9-cis-retinol dehydrogenase creates a unique band pattern specific to the DNA of subjects suffering from cancer; f) preparing DNA obtained from a sample of a subject for diagnosis by steps (a–e); and g) comparing the detected band pattern specific to the DNA obtained from a sample of subjects suffering from cancer or from the disease associated with either an overexpression or an underexpression of a human 9-cis-retinol dehydrogenase from step (e) and the DNA obtained from a sample of the subject for diagnosis from step (f) to determine whether the patterns are the same or different and to diagnose thereby predisposition to the cancer or the disease associated with the overexpression or the underexpression of the human 9-cis-retinol dehydrogenase if the patterns are the same.

In an embodiment of the above-described methods for detecting a predisposition to a cancer or to a disease associated with either an overexpression or an underexpression of a human 9-cis-retinol dehydrogenase in a sample from a subject, the size fractionation in step (c) is effected by a polyacrylamide or agarose gel. In another embodiment of the above-described method, the detectable marker is radioactive isotope, enzyme, dye, biotin, a fluorescent label or a chemiluminescent label.

This invention provides a method for detecting a predisposition to to a cancer or to a disease associated with an overexpression of a human 9-cis-retinol dehydrogenase in a sample from a subject which comprises: a) obtaining DNA from the sample of the subject suffering from cancer or from the disease associated with an overexpression of a human 9-cis-retinol dehydrogenase; b) performing a restriction digest of the DNA with a panel of restriction enzymes; c) separating the resulting DNA fragments by size fractionation; d) contacting the resulting DNA fragments with a nucleic acid probe capable of specifically hybridizing with a unique sequence included within the sequence of a nucleic acid molecule encoding a human 9-cis-retinol dehydrogenase, wherein the sequence of a nucleic acid molecule encoding a human 9-cis-retinol dehydrogenase is labeled with a detectable marker; e) detecting labeled DNA fragments which have hybridized to the nucleic acid probe capable of specifically hybridizing with a unique sequence included within the sequence of a nucleic acid molecule encoding a human 9-cis-retinol dehydrogenase, wherein the sequence of a nucleic acid molecule encoding a human 9-cis-retinol dehydrogenase creates a unique band pattern specific to the DNA of subjects suffering from cancer; f) preparing DNA obtained from a sample of a subject for diagnosis by steps (a–e); and g) comparing the detected band pattern specific to the DNA obtained from a sample of subjects suffering from the cancer or from the disease associated with the overexpression of a human 9-cis-retinol dehydrogenase from step (e) and the DNA obtained from a sample of the subject for diagnosis from step (f) to determine whether the patterns are the same or different and to diagnose thereby predisposition to the cancer or the disease associated with the overexpression of the human 9-cis-retinol dehydrogenase if the patterns are the same.

In an embodiment of any of the above-described methods for detecting a predisposition to a cancer or to a disease associated with an overexpression of a human 9-cis-retinol dehydrogenase in a sample from a subject, the human 9-cis-retinol dehydrogenase is overexpressed in a mammary tissue sample from a subject, thereby detecting a predisposition to mammary cancer. Accordingly, the detection of an elevated level of human 9-cis-retinol dehydrogenase in a human mammary tissue sample, i.e. a biopsy of human breast tissue or human mammary tissue in cell culture, using any of the above-described methods may indicate a predisposition of the subject to a mammary cancer. Accordingly, elevated levels of the human enzyme 9-cis-retinol dehydrogenase may be a marker for transformation, initiation of cancer or the progression of cancer.

This invention provides a method for detecting a predisposition to to a cancer or to a disease associated with an underexpression of a human 9-cis-retinol dehydrogenase in a sample from a subject which comprises: a) obtaining DNA from the sample of the subject suffering from cancer or from the disease associated with an underexpression of a human 9-cis-retinol dehydrogenase; b) performing a restriction digest of the DNA with a panel of restriction enzymes; c) separating the resulting DNA fragments by size fractionation; d) contacting the resulting DNA fragments with a nucleic acid probe capable of specifically hybridizing with a unique sequence included within the sequence of a nucleic acid molecule encoding a human 9-cis-retinol dehydrogenase, wherein the sequence of a nucleic acid molecule encoding a human 9-cis-retinol dehydrogenase is labeled with a detectable marker; e) detecting labeled DNA fragments which have hybridized to the nucleic acid probe capable of specifically hybridizing with a unique sequence included within the sequence of a nucleic acid molecule encoding a human 9-cis-retinol dehydrogenase, wherein the sequence of a nucleic acid molecule encoding a human 9-cis-retinol dehydrogenase creates a unique band pattern specific to the DNA of subjects suffering from cancer; f) preparing DNA obtained from a sample of a subject for diagnosis by steps (a–e); and g) comparing the detected band pattern specific to the DNA obtained from a sample of subjects suffering from cancer or from the disease associated with the underexpression of a human 9-cis-retinol dehydrogenase from step (e) and the DNA obtained from a sample of the subject for diagnosis from step (f) to determine whether the patterns are the same or different and to diagnose thereby predisposition to the cancer or the disease associated with the underexpression of the human 9-cis-retinol dehydrogenase if the patterns are the same.

In an embodiment of the above-described methods for detecting a predisposition to a cancer or to a disease associated with either an overexpression or an underexpression of a human 9-cis-retinol dehydrogenase in a sample from a subject, the size fractionation in step (c) is effected by a polyacrylamide or agarose gel. In another embodiment of the above-described method, the detectable marker is radioactive isotope, enzyme, dye, biotin, a fluorescent label or a chemiluminescent label.

This invention provides a method for detecting a predisposition to a cancer or a disease associated with the overexpression or under expression of a human 9-cis-retinol dehydrogenase in a sample from a subject which comprises: a) obtaining RNA from the sample of the subject suffering from the cancer or the disease associated with the overexpression or under expression of the human 9-cis-retinol dehydrogenase; b) separating the RNA sample by size fractionation; c) contacting the resulting RNA species with a nucleic acid probe capable of specifically hybridizing with a unique sequence included within the sequence of a nucleic acid molecule encoding a human 9-cis-retinol dehydrogenase, wherein the sequence of a nucleic acid molecule encoding a human 9-cis-retinol dehydrogenase is labeled with a detectable marker; d) detecting labeled bands which have hybridized to the RNA species to create a unique band pattern specific to the RNA of subjects suffering from the cancer or the disease associated with the overexpression or under expression of the human 9-cis-retinol dehydrogenase; e) preparing RNA obtained from a sample of a subject for diagnosis by steps (a–d); and f) comparing the detected band pattern specific to the RNA obtained from a sample of subjects suffering from the cancer or the disease associated with the overexpression or under expression of a human 9-cis-retinol dehydrogenase from step (d) and the RNA obtained from a sample of the subject for diagnosis from step (f) to determine whether the patterns are the same or different and to diagnose thereby predisposition to the cancer or the disease associated with the overexpression or underexpression of the human 9-cis-retinol dehydrogenase if the patterns are the same.

In an embodiment of the above-described methods for detecting a predisposition to a cancer or to a disease associated with either an overexpression or an underexpression of a human 9-cis-retinol dehydrogenase in a sample from a subject, the size fractionation in step (c) is effected by a polyacrylamide or agarose gel. In another embodiment of the above-described method, the detectable marker is radioactive isotope, enzyme, dye, biotin, a fluorescent label or a chemiluminescent label. In a further embodiment of any of the above-described methods for detecting a predisposition to a cancer or a disease associated with the overexpression or under expression of a human 9-cis-retinol dehydrogenase in a sample from a subject, the cancer or the disease associated with the overexpression or underexpression of the human 9-cis-retinol dehydrogenase is diagnosed.

This invention provides an antisense oligonucleotide having a sequence capable of specifically hybridizing to an mRNA molecule encoding a human 9-cis-retinol dehydrogenase so as to prevent expression of the mRNA molecule. In an embodiment the antisense oligonucleotide has a sequence capable of specifically hybridizing to the isolated cDNA molecule encoding a mammalian 9-cis-retinol dehydrogenase. In another embodiment the antisense oligonucleotide has a sequence capable of specifically hybridizing to the isolated genomic DNA molecule encoding a mammalian 9-cis-retinol dehydrogenase. In an embodiment the antisense oligonucleotide has a sequence capable of specifically hybridizing to the isolated RNA molecule encoding a mammalian 9-cis-retinol dehydrogenase.

As used herein, the phrase "specifically hybridizing" means the ability of a nucleic acid molecule to recognize a nucleic acid sequence complementary to its own and to form double-helical segments through hydrogen bonding between complementary base pairs. As used herein, a "unique sequence" is a sequence specific to only the nucleic acid molecules encoding the 9-cis-retinol dehydrogenase protein. Nucleic acid probe technology is well known to those skilled in the art who will readily appreciate that such probes may vary greatly in length and may be labeled with a detectable label, such as a radioisotope or fluorescent dye, to facilitate detection of the probe. Detection of nucleic acid molecules encoding the 9-cis-retinol dehydrogenase protein is useful as a diagnostic test for any disease process in which levels of expression of the corresponding 9-cis-retinol dehydrogenase protein is altered. DNA probe molecules are produced by insertion of a DNA molecule which encodes mammalian 9-cis-retinol dehydrogenase protein or fragments thereof into suitable vectors, such as plasmids or bacteriophages, followed by insertion into suitable bacterial host cells and replication and harvesting of the DNA probes, all using methods well known in the art. For example, the DNA may be extracted from a cell lysate using phenol and ethanol, digested with restriction enzymes corresponding to the insertion sites of the DNA into the vector (discussed above), electrophoresed, and cut out of the resulting gel. Examples of such DNA molecules are shown in FIGS. 1A–1B and 4A–4G. The probes are useful for 'in situ' hybridization or in order to locate tissues which express this gene family, or for other hybridization assays for the presence of these genes or their mRNA in various biological tissues. In addition, synthesized oligonucleotides (produced by a DNA synthesizer) complementary to the sequence of a DNA molecule which encodes a mammalian 9-cis-retinol dehydrogenase protein, e.g. human 9-cis-retinol dehydrogenase are useful as probes for this gene, for its associated mRNA, or for the isolation of related genes by homology screening of genomic or cDNA libraries, or by the use of amplification techniques such as the Polymerase Chain Reaction.

A preferred embodiment of a nucleic acid molecule probe of a mammalian 9-cis-retinol dehydrogenase protein is a DNA molecule probe.

This invention provides a purified 9-cis-retinol dehydrogenase, wherein the 9-cis-retinol dehydrogenase is a human 9-cis-retinol dehydrogenase.

This invention provides an antibody directed to a purified 9-cis-retinol dehydrogenase or to a purified 9-cis-retinol dehydrogenase, wherein the 9-cis-retinol dehydrogenase is a human 9-cis-retinol dehydrogenase.

This invention provides an antibody capable of specifically recognizing 9-cis-retinol dehydrogenase. In an embodiment the antibody may be a polyclonal antibody. In another embodiment the antibody may be a monoclonal antibody.

This invention provides an antibody capable of specifically recognizing unique amino acid residues of 9-cis-retinol dehydrogenase. In a preferred embodiment of the antibody the unique amino acid residues of 9-cis-retinol dehydrogenase are HYGGAFLKYLKMQQRIMNLI (SEQ ID NO: 9).

Polyclonal antibodies may be produced by injecting a host animal such as rabbit, rat, goat, mouse or other animal with the immunogen of this invention. The sera are extracted from the host animal and are screened to obtain polyclonal antibodies which are specific to the immunogen. Methods of screening for polyclonal antibodies are well known to those of ordinary skill in the art such as those disclosed in Harlow & Lane, *Antibodies: A Laboratory Manual*, (Cold Spring Harbor Laboratories, Cold Spring Harbor, N.Y.: 1988) the contents of which are hereby incorporated by reference.

The monoclonal antibodies may be produced by immunizing for example, mice with an immunogen. The mice are inoculated intraperitoneally with an immunogenic amount of the above-described immunogen and then boosted with similar amounts of the immunogen. Spleens are collected from the immunized mice a few days after the final boost and a cell suspension is prepared from the spleens for use in the fusion.

Hybridomas may be prepared from the splenocytes and a murine tumor partner using the general somatic cell hybridization technique of Kohler, B. and Milstein, C., Nature (1975) 256: 495–497. Available murine myeloma lines, such as those from the American Type Culture Collection (ATCC) 12301 Parklawn Drive, Rockville, Md. 20852 USA, may be used in the hybridization. Basically, the technique involves fusing the tumor cells and splenocytes using a fusogen such as polyethylene glycol. After the fusion the cells are separated from the fusion medium and grown in a selective growth medium, such as HAT medium, to eliminate unhybridized parent cells. The hybridomas may be expanded, if desired, and supernatants may be assayed by conventional immunoassay procedures, for example radioimmunoassay, using the immunizing agent as antigen. Positive clones may be characterized further to determine whether they meet the criteria of the invention antibodies.

Hybridomas that produce such antibodies may be grown in vitro or in vivo using known procedures. The monoclonal antibodies may be isolated from the culture media or body fluids, as the case may be, by conventional immunoglobulin purification procedures such as ammonium sulfate precipitation, gel electrophoresis, dialysis, chromatography, and ultrafiltration, if desired.

In the practice of the subject invention any of the above-described antibodies may be labeled with a detectable marker. In one embodiment, the labeled antibody is a purified labeled antibody. The term "antibody" includes, by way of example, both naturally occurring and non-naturally occurring antibodies. Specifically, the term "antibody" includes polyclonal and monoclonal antibodies, and fragments thereof. Furthermore, the term "antibody" includes chimeric antibodies and wholly synthetic antibodies, and fragments thereof. A "detectable moiety" which functions as detectable labels are well known to those of ordinary skill in the art and include, but are not limited to, a fluorescent label, a radioactive atom, a paramagnetic ion, biotin, a chemiluminescent label or a label which may be detected through a secondary enzymatic or binding step. The secondary enzymatic or binding step may comprise the use of digoxigenin, alkaline phosphatase, horseradish peroxidase, β-galactosidase, fluorescein or steptavidin/biotin. Methods of labeling antibodies are well known in the art.

This invention provides a method of detecting expression of a mammalian 9-cis-retinol dehydrogenase in a tissue or cells from a sample which comprises: a) incubating a sample of the tissue or cells from a sample with an antibody which specifically recognizes 9-cis-retinol dehydrogenase and is labeled with a detectable marker under conditions permitting a binding of the antibody to the tissue or the cells; b) detecting labeled tissue or cells, thereby detecting expression of the mammalian 9-cis-retinol dehydrogenase in the tissue or the cells.

As used herein, "sample" means body tissue or fluid, including but not limited to blood, urine, saliva, and cerebrospinal fluid.

This invention provides a method of detecting human 9-cis-retinol dehydrogenase in a sample which comprises: a) contacting the sample with of any of the above-described antibodies under conditions permitting the formation of a complex between the antibody and the human 9-cis-retinol dehydrogenase in the sample; and b) detecting the complex formed in step (a) thereby detecting the presence of human 9-cis-retinol dehydrogenase in the sample. In an embodiment the antibody is labeled with a detectable marker. In an embodiment the the detectable marker is radioactive isotope, enzyme, dye, biotin, a fluorescent label or a chemiluminescent label.

This invention provides a method of detecting a disease which is responsive to treatment with a retinoid, comprising the method of detecting human 9-cis-retinol dehydrogenase in a tissue or cells from a sample, wherein the detection of the expression of the mammalian 9-cis-retinol dehydrogenase indicates the disease is responsive to retinoic acid treatment.

This invention provides a method of detecting a disease which is refractory to treatment with a retinoid comprising the method of detecting human 9-cis-retinol dehydrogenase in a tissue or cells from a sample, wherein the detection of the expression of the mammalian 9-cis-retinol dehydrogenase indicates the disease is refractory to retinoic acid treatment. This invention provides a pharmaceutical composition comprising an amount of any of the above-described oligonucleotides and effective to prevent overexpression of a human 9-cis-retinol dehydrogenase and a pharmaceutically acceptable carrier capable of passing through a cell membrane.

This invention provides a pharmaceutical composition comprising an amount of any compounds, e.g. retinoids, which are determined to be potentially therapeutic, i.e. their toxicity as determined by any of the methods described supra is less than that of compounds which in a smaller concentration have a higher toxicity, administered in effective amounts and a pharmaceutically acceptable carrier capable of passing through a cell membrane.

This invention provides a method of administering the above-described pharmaceutical composition comprising an amount of any of the above-described oligonucleotides or compounds which are determined to be potentially therapeutic, wherein the administration is intravenous, intraperitoneal, intrathecal, intralymphatical, intramuscular, intralesional, parenteral, epidural, subcutaneous; by infusion, liposome-mediated delivery, aerosol delivery; topical, oral, nasal, anal, ocular or otic delivery.

The present invention also provides a pharmaceutical composition comprising a effective amount of any of the above-described oligonucleotides or compounds which are determined to be potentially therapeutic and a pharmaceutically acceptable carrier. In the subject invention an "effective amount" is any amount of the above-described oligonucleotides or compounds which are determined to be potentially therapeutic, which, when administered to a subject suffering from a disease or abnormality against which the above-described oligonucleotides or compounds which are determined to be potentially therapeutic, are effective, causes reduction, remission, or regression of the disease or abnormality. In the practice of this invention the "pharmaceutically acceptable carrier" is any physiological carrier known to those of ordinary skill in the art useful in formulating pharmaceutical compositions.

In one preferred embodiment the pharmaceutical carrier may be a liquid and the pharmaceutical composition would be in the form of a solution. In another equally preferred embodiment, the pharmaceutically acceptable carrier is a solid and the composition is in the form of a powder or tablet. In a further embodiment, the pharmaceutical carrier is a gel and the composition is in the form of a suppository or cream. In a further embodiment the compound may be formulated as a part of a pharmaceutically acceptable transdermal patch.

A solid carrier can include one or more substances which may also act as flavoring agents, lubricants, solubilizers, suspending agents, fillers, glidants, compression aids, binders or tablet-disintegrating agents; it can also be an encapsulating material. In powders, the carrier is a finely divided solid which is in admixture with the finely divided active ingredient. In tablets, the active ingredient is mixed with a carrier having the necessary compression properties in suitable proportions and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, polyvinylpyrrolidine, low melting waxes and ion exchange resins.

Liquid carriers are used in preparing solutions, suspensions, emulsions, syrups, elixirs and pressurized compositions. The active ingredient can be dissolved or suspended in a pharmaceutically acceptable liquid carrier such as water, an organic solvent, a mixture of both or pharmaceutically acceptable oils or fats. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (partially containing additives as above, e.g. cellulose derivatives, preferably sodium carboxymethyl cellulose solution), alcohols (including monohydric alcohols and polyhydric alcohols, e.g. glycols) and their derivatives, and oils (e.g. fractionated coconut oil and arachis oil). For parenteral administration, the carrier can also be an oily ester such as ethyl oleate and isopropyl myristate. Sterile liquid carriers are useful in sterile liquid form compositions for parenteral administration. The liquid carrier for pressurized compositions can be halogenated hydrocarbon or other pharmaceutically acceptable propellent.

Liquid pharmaceutical compositions which are sterile solutions or suspensions can be utilized by for example, intramuscular, intrathecal, epidural, intraperitoneal or subcutaneous injection. Sterile solutions can also be administered intravenously. The compounds may be prepared as a sterile solid composition which may be dissolved or suspended at the time of administration using sterile water, saline, or other appropriate sterile injectable medium. Carriers are intended to include necessary and inert binders, suspending agents, lubricants, flavorants, sweeteners, preservatives, dyes, and coatings.

The above-described oligonucleotides or compounds which are determined to be potentially therapeutic can be administered orally in the form of a sterile solution or suspension containing other solutes or suspending agents, for example, enough saline or glucose to make the solution isotonic, bile salts, acacia, gelatin, sorbitan monoleate, polysorbate 80 (oleate esters of sorbitol and its anhydrides copolymerized with ethylene oxide) and the like.

The above-described oligonucleotides or compounds which are determined to be potentially therapeutic can also be administered orally either in liquid or solid composition form. Compositions suitable for oral administration include solid forms, such as pills, capsules, granules, tablets, and powders, and liquid forms, such as solutions, syrups, elixirs, and suspensions. Forms useful for parenteral administration include sterile solutions, emulsions, and suspensions.

Optimal dosages to be administered may be determined by those skilled in the art, and will vary with the particular oligonucleotide in use, the strength of the preparation, the mode of administration, and the advancement of the disease condition or abnormality. Additional factors depending on the particular subject being treated will result in a need to adjust dosages, including subject age, weight, gender, diet, and time of administration.

This invention provides a recombinant non-human vertebrate animal wherein the functional 9-cis-retinol dehydrogenase is not expressed. In an embodiment the recombinant non-human vertebrate animal is a rodent. In a preferred embodiment the rodent is a mouse.

This invention provides a recombinant non-human vertebrate animal wherein the functional 9-cis-retinol dehydrogenase is underexpressed. In an embodiment the recombinant non-human vertebrate animal is a rodent. In a preferred the rodent is a mouse.

This invention provides a method of treating any of the above-described recombinant non-human vertebrate animals comprising adminitration of a vector comprising an isolated mammalian nucleic acid molecule encoding a 9-cis-retinol dehydrogenase.

This invention will be better understood from the Experimental Details which follow. However, one skilled in the art will readily appreciate that the specific methods and results discussed are merely illustrative of the invention as described more fully in the claims which follow thereafter.

EXPERIMENTAL DETAILS

First Series of Experiments

All-trans- and 9-cis-retinoic acid are active retinoids for regulating expression of retinoid responsive genes, serving as ligands for two classes of ligand-dependent transcription factors, the retinoic acid receptors and retinoid X receptors. Little is known, however, regarding 9-cis-retinoic acid formation. We have obtained a 1.4-kilobase cDNA clone from a normalized human breast tissue library, which when expressed in CHO cells encodes a protein that avidly catalyzes oxidation of 9-cis-retinol to 9-cis-retinaldehyde. This protein also catalyzes oxidation of 13-cis-retinol at a rate approximately 10% of that of the 9-cis isomer but does not catalyze all-trans-retinol oxidation. NAD+ was the preferred electron acceptor for oxidation of 9-cis-retinol, although NADP+ supported low rates of 9-cis-retinol oxidation. The rate of 9-cis-retinol oxidation was optimal at pHs between 7.5 and 8. Sequence analysis indicates that the cDNA encodes a protein of 319 amino acids that resembles members of the short chain alcohol dehydrogenase protein family. mRNA for the protein is most abundant in human mammary tissue followed by kidney and testis, with lower levels of expression in liver, adrenals, lung, pancreas, and skeletal muscle. We propose that this cDNA encodes a previously unknown stereospecific enzyme, 9-cis-retinol dehydrogenase, which probably plays a role in 9-cis-retinoic acid formation.

Retinoids (vitamin A and its analogs) are essential dietary substances that are needed by mammals for reproduction, normal embryogenesis, growth, vision, and maintaining normal cellular differentiation and the integrity of the immune system (1–5). Within cells, retinoids regulate gene transcription acting through ligand-dependent transcription factors, the retinoic acid receptors (RARs)[1], and the retinoid X receptors (RXRs) (6,7). All-trans-retinoic acid binds only to RARs with high affinity, whereas its 9-cis isomer binds with high affinity to both RARs and RXRs. The actions of all-trans- and 9-cis-retinoic acid in regulating cellular responses are distinct and not interchangeable.

In contrast to the great explosion of information regarding the actions of retinoid receptors in regulating gene transcription, information regrading how the abundant precursor retinol is physiologically activated to form the ligands needed to activate retinoid receptors is only slowly emerging (see Refs. 8 and 9 for recent reviews). It is clear that the pathway for conversion of retinol to retinoic acid involves first the oxidation of retinol to retinaldehyde and then the oxidation of retinaldehyde to retinoic acid. Numerous enzymes that are able to catalyze either retinol or retinaldehyde oxidation have been identified, purified, and/or characterized (8–10). These enzymes are members of four distinct families: the alcohol dehydrogenases, the short chain alcohol dehydrogenases, the aldehyde dehydrogenases, and cytochrome P-450s (8–10). At present, the most attention has focused on enzymes responsible for the oxidation of all-trans-retinol to all-trans-retinaldehyde (11–15). Several recent reports have indicated that both alcohol dehydrogenases and short chain alcohol dehydrogenases may be responsible for catalyzing all-trans-retinol oxidation (11–15), but the exact in vivo roles of each of these dehydrogenases in all-trans-retinoic acid formation remains controversial (8).

9-cis-Retinoic acid has been reported to be present in mammalian tissues and cells (16–18), but it has not been convincingly established how 9-cis-retinoic acid is formed within tissues and cells. Urbach and Rando have reported that liver microsomes can nonenzymatically catalyze the isomerization of all-trans-retinoic acid to the 9-cis isomer (19). Others have demonstrated that 9-cis-β-carotene can be converted to 9-cis-retinoic acid within rat tissues (20). However, this latter pathway cannot be an essential one for 9-cis-retinoic acid formation because rats maintained on a β-carotene-free purified diet containing only retinol as a precursor for retinoic acid formation are normal. In this communication, we report the characterization of a cDNA clone for a novel human enzyme that we have designated 9-cis-retinol dehydrogenase (9cRDH) and that catalyzes in a stereospecific manner the oxidation of 9-cis-retinol to 9-cis-retinaldehyde, a first enzymatic step needed for 9-cis-retinoic acid formation. Because it has been established that 9-cis-retinaldehyde can be further oxidized to 9-cis-retinoic acid by abundant tissue retinaldehyde dehydrogenases (21–23), it is possible that 9cRDH catalyzes a key oxidation step in the formation of 9-cis-retinoic acid.

EXPERIMENTAL PROCEDURES cDNA Characterization and Sequence Analysis. Using a primer homology strategy based on sequence information provided by Napoli and colleagues (11–14), we screened a mouse testis library for a retinol dehydrogenase cDNA clone We obtained a 550-bp cDNA that we submitted for automated DNA sequence analysis (ABI Applied Biosystems, model 373A, Columbia, Md.) through the Columbia University Comprehensive Cancer Center Core DNA Sequencing Facility. When this partial cDNA sequence was compared with sequences that had been deposited in GenBank™ (National Center for Biotechnology Information, Bethesda, Md.), a very high degree of sequence homology was observed with an unidentified cDNA sequence that had been partially sequenced (330 of approximately 1400 bp) and deposited with GenBank™ by the IMAGE Consortium (accession number R50456) We obtained the cDNA through Research Genetics, Inc (Huntsville, Ala.), and its complete nucleotide sequence was determined. The 1.4-kb cDNA was subcloned so that overlapping sequences were obtained for all regions of the cDNA and was used for all studies reported below Expression of 9-cis-Retinol Dehydrogenase. The 1.4-kb human cDNA was directionally cloned as a BamHI-EcoRI insert into the mammalian expression vector pcDNA3 (Invitrogen, San Diego, Calif.) where expression is driven by the strong promoter from the immediate early gene of the human cytomegalovirus. Both the expression vector containing the cDNA insert and vector alone were transfected using calcium phosphate into CHO cells according to standard procedures (24). Routinely, 20, μg of plasmid DNA (with or without the cDNA insert) was transfected into $2 \times 10_6$ CHO cells maintained on 100-mm tissue culture plates. At the time of transfection, the CHO cells were approximately 80~o confluent. 27 h after transfection, the transfection medium was removed from the CHO cells, and they were washed with 5 ml of ice-cold 10 mM sodium phosphate, 150 mM NaCl, pH 7.4 (PBS). Washed CHO cells were scraped from the plate and collected by centrifugation at 500×g at 4° C. for 10 min. The pelleted cells were washed with 5 ml of ice-cold PBS two additional times and stored as a cell pellet at −20° C. for up to 2 weeks prior to assay for retinol dehydrogenase activity.

Retinoids. All-trans-retinol was obtained as a gift from Dr. Christian Eckhoff of Hoffmann-LaRoche, Inc. (Nutley, N.J.), and 13-cis-retinol was purchased from Sigma. 9-cis-Retinol was synthesized by $NaBH_4$ reduction of authentic 9-cis-retinaldehyde (Sigma) and subsequently purified by normal phase HPLC essentially as we have described for 11-cis-retinol synthesis and purification (25). All-trans-, 13-cis-, and 9-cis-retinaldehydes were purchased from Sigma.

Enzymatic Assay of Retinol Dehydrogenase Activity. Transfected CHO cell pellets were homogenized in PBS at 4° C. using 50 strokes of a Dounce homogenizer For assay of retinol dehydrogenase activity, aliquots of unfractionated CHO cell homogenate were incubated with 10, μM retinol (either as the all-trans, 13-cis, or 9-cis isomer added in ethanol) and either 2 mM NAD+ or 2 mM NADP+ in 10 mM Hepes containing 150 mM KCl, 1 mM EDTA, and 10, μg/ml phosphotidyl choline at pH 8.0 and 37° C. for prechosen time intervals. The final assay volume was 0.6 ml. Assays were routinely carried out in amber glass tubes that had been flushed with $N_2$ to shield the retinoids from both light and $O_2$ All subsequent extractions and procedures were carried out in a manner that minimized exposure of the retinoids to light and $O_2$.

Immediately following incubation, the assay mixture was denatured with an equal volume of absolute ethanol (0.6 ml), and the retinoids were extracted into 3 ml of HPLC grade hexane. Following one backwash of the hexane extract with 0.5 ml of deionized water, the hexane was evaporated to dryness under a gentle stream of $N_2$, and the extracted retinoids were immediately redissolved in 120 µl of hexane and analyzed by normal phase HPLC (see below).

For assay of 9cRDH activity in rat tissues, 300-g male Sprague-Dawley rats were sacrificed in a $CO_2$-saturated atmosphere and liver, kidney, spleen, testis, and epididymis were quickly removed and placed on ice. Immediately after dissection, each tissue was finely minced with razor blades, placed into a Dounce homogenizer containing 4 volumes of ice-cold PBS and homogenized with 50 strokes of the homogenizer. The resulting homogenate was centrifuged at 500×g for 10 min to remove debris and was maintained on ice prior to its use for 9cRDH assay. Assays of 9cRDH activity were carried out exactly as described above for CHO cell homogenates. For each assay, a blank containing substrate and homogenate was maintained on ice for 1 h and was subsequently extracted to correct for possible endogenous 9-cis-retinaldehyde presence in the enzyme sources; however, in no homogenate was any 9-cis—retinaldehyde observed.

The protein concentrations of CHO cell homogenates and of each homogenate from the rat tissues were determined using the Bradford reagent (Pierce) according to the manufacturer's instructions.

HPLC Procedures. Stereoisomers of both retinol and retinaldehyde were separated on a 4.6×250-mm Vydac 101HS54 silica column using hexane:n-propanol:1-octanol (98.9:1.0:0.1 v/v) flowing at 1.5 ml/min as the mobile phase. The running column was preceded by a silica guard column. Retinols and retinaldehydes were detected by UV absorbance at 350 nm. Retention times for all-trans-, 13-cis-, and 9-cis-retinols were established using purified compounds obtained as described above. Retention times for all-trans-, 13-cis-, and 9-cis-retinaldehyde were determined using commercial standards (Sigma). Quantities of each retinol and retinaldehyde isomer present in extracts were determined by comparisons of the integrated areas under the HPLC peaks with a standard curve constructed relating integrated peak area with known masses of each retinoid isomer. The concentrations of each retinoid isomer were determined by UV-visible spectrophotometry using published extinction coefficients for each retinol and retinaldehyde isomer (26).

Northern Blot Analysis for 9cRDH Expression in Human Tissues. Northern blot analysis was used to explore 9cRDH expression in human testis, kidney, lung, liver, heart, adrenals, pancreas, thyroid, skeletal muscle, placenta, mammary gland, and a mammary tumor. All tissues, with the exception of mammary gland and mammary tumor, were obtained at autopsy. The mammary gland and mammary tumor were obtained as frozen blocks embedded for diagnosis. Total RNA was isolated from each tissue sample using standard procedures (24). Total RNA samples were electorphoresed on 0.8% agarose containing 2.2 M formaldehyde at 0.5 V/cm for 14 h. After electrophoresis the gel was soaked in 20×SSC for 1 h and blotted overnight onto a nitrocellulose membrane using 10×SSC. The total RNA transferred to the nitrocellulose membrane was baked at 80° C. in a vacuum oven for 2 h. The blot was probed with a cRNA probe generated from the full-length human 9cRDH cDNA clone in pcDNA3 (as used for CHO cell expression studies). The cRNA probe was labeled using SP6 polymerase and [$^{32}$P] UTP. Hybridization was carried out at 65° C. in 5×SSC, 60% formamide, 1% SDS, 5×Denhardt's solution, 100, µg/ml salmon sperm DNA, 100 µg/ml yeast tRNA, and 7% dextran sulfate. After hybridization, the final wash f the RNA—RNA blot was at 80° C. in 0.2×SSC and 0.1% SDS for 1 h.

EXPERIMENTAL RESULTS

We were interested in obtaining a cDNA clone for a retinol dehydrogenase from a mouse testis library for use in study of the cellular sites of retinoic acid formation within the testis. Using a primer homology strategy similar to strategies described by Napoli and colleagues (11–14), we obtained a partial length product (550 bp) which, upon search of known sequences present in GenBank™, was found to have a very high sequence homology to a previously unidentified cDNA having a length of 1.4 kb and for which a partial sequence had been obtained as part of the Human Genome Project. Because this cDNA was much larger than the one we obtained from the screen of the mouse testis library, we obtained the cDNA for preliminary study. Our preliminary characterizations of this human cDNA suggested to us that the cDNA encoded a protein that could catalyze the reduction of NAD+ when a mixture of retinol isomers was incubated with expressed protein encoded by the cDNA; consequently, we set out to characterize more extensively this human cDNA and the protein that it encodes.

Because only 330 bp of the approximately 1400 bp present in the human cDNA had been sequenced, we completed the sequencing of this cDNA. The complete nucleotide sequence for the cDNA is provided in FIG. 1 along with the deduced amino acid sequence for the protein that it encodes. Sequence analysis of the cDNA revealed the presence of a putative translation start site approximately 80 bp downstream from its 5'-end and continuing for approximately 170 bp after the occurrence of a translation stop codon. The cDNA consisted of 1239 bp and could encode a protein of 319 amino acids. A search of the GenBank™ for homologous sequences indicated that bovine retinal pigment epithelial 11-cis-retinol dehydrogenase and rat liver all-trans-retinol dehydrogenases, types I, II, and III, were highly homologous to that of the 1.4-kb cDNA. For comparison, the deduced amino acid sequences for bovine 11-cis-retinol dehydrogenase and rat all-trans-retinol dehydrogenases, types I and II, are also provided in FIG. 1. No other sequences present in the GenBank™ data base were similarly homologous to the sequence that we obtained. Computer analysis of the predicted amino acid sequence indicated that the protein contained no membrane spanning domains. Furthermore, computer analysis of the amino acid sequences indicated that the protein encoded by the cDNA clone is most probably a member of the family of short chain alcohol dehydrogenases, like the bovine 11-cis-retinol dehydrogenase (27, 28) and the rat liver retinol dehydrogenases, types I, II, and III (11–14).

Based on these sequence homologies and the results from our preliminary studies, it seemed likely to us that we had obtained a human cDNA clone for a retinol dehydrogenase.

However, based on our preliminary studies, it was not fully clear whether this cDNA was a human homolog of one of the rat liver all-trans-retinol dehydrogenases (11–14) or whether we had cloned a new and previously undescribed retinol dehydrogenase. Because 11-cis-retinol dehydrogenase is expressed only in the retinal pigment epithelium (27, 28) and 11-cis-retinol is found only in the eye (4), we could not have cloned the human homolog for this enzyme. To determine the substrate specificity of the enzyme encoded by our cDNA, we expressed the cDNA in CHO cells and incubated homogenate from these CHO cells with all-trans-, 9-cis-, or 13-cis-retinol. As is seen in FIG. 2, in the presence of 2 mM NAD+, homogenate from the transfected CHO cells avidly oxidized 9-cis-retinol to 9-cis-retinaldehyde but was unable to catalyze the oxidation of all-trans-retinol to all-trans-retinaldehyde. The CHO cell homogenate catalyzed the oxidation of 13-cis-retinol to its corresponding aldehyde, but at a rate that was only 10% of that observed for the oxidation of 9-cis-retinol. Over 60% of the 9-cis-retinol added (at an in assay concentration of 10 μM) could be oxidized to 9-cis-retinaldehyde by the CHO cell homogenate. Oxidation of 9-cis-retinol was both protein- and time-dependent, and NADP+ was a poor co-factor for the reaction (8% of the activity of NAD+ when both are provided at concentrations of 2 mM) The CHO cell homogenates were unable to catalyze any detectable oxidation of all-trans-retinol, regardless of whether this retinoid was added to the CHO homogenate in organic solvents, bound to rat testis cellular retinol-binding protein, type I, bound to albumin, or in detergent emulsions. We conclude from these experiments that the 1.4-kb cDNA encodes a stereospecific 9-cis-retinol dehydrogenase (9cRDH) that has not been previously identified.

Further characterization of 9cRDH activity expressed in CHO cells indicated that the enzyme has a pH optimum in the range of 7.5–8 0 and that 9cRDH activity is not inhibited by ethanol or zinc chelators like EDTA or o-phenanthroline, unlike cytosolic alcohol dehydrogenases that can oxidize retinol to retinaldehyde (15, 29) Neither exposure to high NaCl concentrations (up to 1 M) nor exposure to reducing reagents (1 mM, β-mercaptoethanol and 1 mM dithiothreitol) influenced 9cRDH activity. CHO cell expressed 9cRDH activity, however, is sensitive to detergents and is rapidly inactivated by exposure to 1% (w/v) Triton X-100 or to 1% (w/v) sodium cholate. In addition, the 9cRDH activity present in CHO cell homogenates is rapidly lost upon storage at −20° C., although the activity does not appear to be lost when CHO cells are frozen intact.

Figure 3:
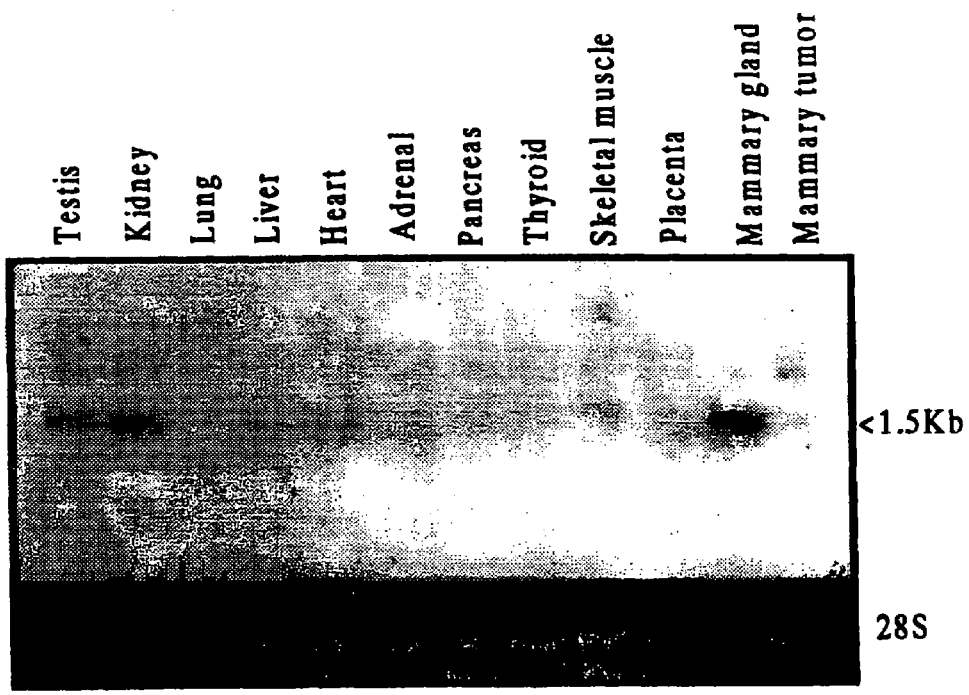
FIG. 3. Northern blot analysis of 9cRDH expression in human testis, kidney, lung, liver, heart, adrenals, pancreas, thyroid, skeletal muscle, placenta, mammary gland, and mammary tumor. All tissues, with the exception of placenta, mammary gland and mammary tumor were obtained at autopsy. The mammary gland and mammary tumor were obtained as frozen blocks embedded for diagnosis, and term placenta was obtained as the intact tissue. This analysis was carried out as described under "Experimental Procedures" with 50 µg of total RNA loaded in each lane except for mammary gland where only 20 µg of total RNA was loaded.

The distribution of 9cRDH expression in human tissues was assessed by Northern blot analysis (FIG. 3) The transcript identified by Northern blot analysis is approximately 1.5 kb, a size that agrees well with that predicted by the full-length human 9cRDH cDNA clone. 9cRDH mRNA is most abundant in normal mammary tissue and is relatively abundant in kidney and the testis. Liver, heart, and adrenals each express 9cRDH mRNA at nearly equal levels, but these are lower than those of mammary tissue, kidney and testis. 9cRDH mRNA is present at low levels in lung, pancreas, and skeletal muscle. Interestingly, 9cRDH is only very weakly expressed in total RNA prepared from a human mammary tumor. We also asked whether 9cRDH activity could be detected in whole tissue homogenates prepared from rat liver, spleen, kidney, epididymis, and testis. As shown in Table I, 9cRDH specific activity was highest in the kidney followed by the testis, epididymis, liver, and spleen.

TABLE I

Specific activity levels of 9-cis-Retinol dehydrogenase in selected rat tissue homogenates

| Tissue | 9-cis-Retinaldehyde formed nmol/h/mg protein |
|---|---|
| Liver | 2.4 ± 0.4[a] |
| Kidney | 4.9 ± 0.1 |
| Spleen | 1.6 ± 0.3 |
| Testis | 3.6 ± 0.5 |
| Epididymis | 2.8 ± 1.0 |

[a]Values are expressed as the means ± S.D. for activity determinations for homogenates prepared from tissues from three animals

EXPERIMENTAL DISCUSSION

It is generally accepted that 9-cis-retinoic acid is a physiologically important molecule for mediating retinoid actions in regulating gene expression, but only limited information has been available regarding how 9-cis-retinoic acid or any 9-cis-retinoid is formed within tissues and cells. This is unlike the visual process where it is now well established that isomerization of all-trans-retinoids to 11-cis-retinoids is catalyzed by a specific enzyme and that the isomerization takes place at the level of the retinols and not the retinaldehydes (4). Because of the first reports in 1992 that 9-cis-retinoic acid is a ligand for the RXRs, several studies have explored possible pathways for 9-cis-retinoic acid formation. Urbach and Rando have reported that membranes prepared from bovine liver will catalyze non-enzymatically the isomerization of all-trans-retinoic acid to 9-cis-retinoic acid (19). This isomerization was shown to depend on free sulfhydryl groups present in the microsomes and not to involve the participation of an enzyme (19). Krinsky, Russell, and colleagues have reported that 9-cis-β-carotene serves as a precursor for 9-cis-retinoic acid in vivo in the rat (20) However, because rats maintained on carotenoid-free diets display normal health, the conversion of 9-cis-β-carotene to 9-cis-retinoic acid cannot be an essential pathway for formation of this retinoic acid isomer. In studies of retinaldehyde dehydrogenases purified from rat kidney (21, 22) and rat liver (23), the ability of these enzymes to catalyze the oxidation of 9-cisretinaldehyde to 9-cis-retinoic acid was taken to suggest that a pathway starting with 9-cis-retinol may be important for 9-cis—retinoic acid formation (21, 22). To further substantiate this possibility, Bhat, Lacroix, and colleagues demonstrated the presence of 9-cis-retinol in rat kidney at levels that were approximately 10% of that of all-trans-retinol (22). Our work characterizing a stereospecific 9cRDH activity and demonstration of the broad tissue distribution of this enzyme adds additional support to the hypothesis that 9-cis-retinoic acid is formed within tissues via a pathway that involves both 9-cis-retinol and 9-cis-retinaldehyde.

A search of the GenBank™ for DNA sequences homologous to that of 9cRDH revealed that the sequence of the 9cRDH cDNA is approximately 87% homologous to that of the full-length cDNA for bovine retinal pigment epithelium 11-cis-retinol dehydrogenase (27) and approximately 48% homologous to the coding region of the cDNA sequence for rat liver all-trans-retinol dehydrogenase, type II (13). At the amino acid level, the deduced amino acid sequence for 9cRDH is 89% identical to that of bovine 11-cis-retinol dehydrogenase (27) and 53% identical to that of rat liver all-trans-retinol dehydrogenase, type II (13). Like the bovine 11-cis-retinol dehydrogenase and the rat liver all-trans-retinol dehydrogenases, types I, II, and III, 9cRDH is a member of the family of short chain alcohol dehydrogenases. Moreover, 9cRDH shares many properties including pH optimum, insensitivity to inhibition by ethanol, and sensitivity to detergent inactivation with the other members of this protein family. Most importantly though, like these other short chain alcohol dehydrogenases, 9cRDH shows a marked stereospecificity for retinol substrates.

Based on work showing that a retinaldehyde dehydrogenase purified from rat kidney can catalyze the oxidation of both all-trans- and 9-cis-retinaldehyde and that 9-cis-retinol is present in relatively high levels in the rat kidney (21, 22), it has been hypothesized that 9-cis-retinoic acid is formed in the kidney through a two-step oxidation starting with 9-cis-retinol. The demonstration of 9cRDH in the kidney provides strong support for this hypothesis. Moreover, identification of this short chain alcohol dehydrogenase, 9cRDH, raises many additional interesting questions regarding the biochemical processes that are important for providing 9-cis-retinoids to tissue and cell. One such question concerns how 9-cis-retinoids are formed. Whether or not isomerization of all-trans-retinoic acid actually occurs nonenzymatically in living cells has not been addressed experimentally, although it is clear that some cell types do have the capacity to isomerize all-trans-retinoic acid to the 9-cis isomer (30). Another important question regarding 9-cis-retinoid formation concerns whether there are other short chain alcohol dehydrogenases present in tissues and cells distinct from 9cRDH that catalyze 9-cis-retinol oxidation. There are at least three short chain alcohol dehydrogenases that catalyze all-trans-retinol oxidation (11–14), and it would not seem unreasonable that multiple forms of 9cRDH may also exist. Perhaps most importantly, though, it is essential to gain an understanding of the specific physiologic role or roles played by each of these short chain alcohol dehydrogenases and by each of the alcohol dehydrogenases that catalyze oxidation of retinol to retinaldehyde. These enzymes may be redundant or they all may play significant roles in retinoic acid formation in specific and defined cellular and metabolic contexts. Although it is clear that many enzymes are able to catalyze retinol oxidation, convincing physiologic functions for these enzymes within living organisms remain elusive.

REFERENCES FOR FIRST SERIES OF EXPERIMENTS

1. Wolbach, S. B., and Howe, P. R. (1925) J. Exp. Med. 42, 753–778.
2. Gudas, L. J., Sporn, M. B., and Roberts, A. B. (1994) in The Retinoids, Biology, Chemistry, and Medicine (Sporn, M. B., Roberts, A. B., and Goodman, D. S., eds) pp. 443–520, Raven Press, New York.
3. Hofmann, C., and Eichele, G. (1994) in The Retinoids, Biology, Chemistry, and Medicine (Sporn, M. B., Roberts, A. B., and Goodman, D. S., eds) pp. 387–441, Raven Press, New York.
4. Saari, J. C. (1994) in The Retinoids, Biology, Chemistry, and Medicine (Sporn, M. B., Roberts, A. B, and Goodman, D. S., eds) pp. 351–386, Raven Press, New York.
5. Ross A. C., and Hammerling, U. L. (1994) in The Retinoids, Biology, Chemistry, and Medicine (Sporn, M. B., Roberts, A. B., and Goodman, D. S., eds) pp. 521–543, Raven Press, New York.
6. Mangelsdorf, D. J., Umesono, K., and Evans, R. M. (1994) in The Retinoids, Biology, Chemistry, and Medicine (Sporn, M B., Roberts, A. B., and Goodman, D. S., eds) pp. 319–350, Raven Press, New York.
7. Chambon, P. (1996) FASEB J. 10, 940–954.
8. Durster, G. (1996) Biochemistry 35, 12221–12227.
9. Napoli, J. (1996) FASEB J. 10, 993–1001.
10. Blaner, W. S., and Olson, J. A. (1994) in The Retinoids, Biology, Chemistry, and Medicine (Sporn, M. B., Roberts, A. B., and Goodman, D. S., eds) pp. 229–256, Raven Press, New York.
11. Boerman, M. H. E. M., and Napoli, J. L. (1995) Biochemistry 34, 7027–7037.
12. Boerman, M. H. E M., and Napoli, J. L. (1995) Arch. Biochem. Biophys. 321, 434–441.
13. Chai, X, Zhai, Y., Popescu, G., and Napoli, J. L. (1995) J. Biol. Chem. 270, 28408–28412.
14. Chai, X., and Napoli, J. L. (1996) Gene (Amst.) 169, 219–222.
15. Ang, H. L., Deltour, L., Hayzmizu, T. F., Zgombic-Knight, M., and Durster, G. (1996) J. Biol. Chem. 271, 9526–9534.
16. Levin, A. A., Sturzenbecker, L. J., Kazmer, S., Bosakowski, T., Huselton, C., Allenby, G., Speck, J., Kratzeisen, C. L., Rosenberger, M., Lovey, A., and Grippo, J R. (1992) Nature 355, 359–361.
17. Heyman, R. A, Mangelsdorf, D. J., Kyck, J A., Stein, R. B., Eichele, G., Evans, R. E., and Thaller, C. (1992) Cell 66, 397–406.
18. Pappas, R. S., Newcomer, M. E., and Ong, D. E (1993) Biol. Reprod. 48, 235–247.
19. Urbach, J., and Rando, R. R. (1995) Biochem. J. 299, 459–465.
20. Hebuterne, X., Wang, X.-D., Johnson, E. J., Krinsky, N. I., and Russell, R. M. (1995) J. Lipid Res. 36, 1264–1273.
21. Labrecque, J., Bhat, P. V, and Lacroix, A. (1993) Biochem. Cell Biol. 71, 85–89.
22. Labrecque, J., Dumas, F., Lacroix, A., and Bhat, P V. (1995) Biochem. J. 305, 681–684.
23. E l Akawi, Z., and Napoli, J. L. (1994) Biochemistry 33, 1938–1943.
24. Maniatis, T., Fritsch, E. F., and Sambrook, J. (1982) Molecular Cloning: A Laboratory Manual, 2nd Ed., pp. 7.37–7.84, Cold Spring Harbor Laboratory, Cold Spring Harbor, N.Y.
25. Blaner, W S., Das, S. R., Gouras, P, and Flood, M. T. (1987) J. Biol. Chem. 262, 53–58.
26. Furr, H. C., Barua, A. B., and Olson, J. A. (1994) in The Retinoids, Biology,Chemistry, and Medicine (Sporn, M. B., Roberts, A. B., and Goodman, D. S.,eds) pp. 179–210, Raven Press, New York.
27. Simon, A., Hellman, U., Wernstedt, C., and Eriksson, U. (1995) J. Biol. Chem. 270, 1107–1112.
28. Driessen, C. A., Janssen, B. P., Winkens, H. J., van Bugt, A. H. de Leeuw, T. L., and Janssen, J. J. (1995) Inuest. Ophthalmol. & Visual Sci. 36, 1988–1996.
29. Boleda, M. D., Saubi, N., Farres, J., and Pares, X. (1993) Arch. Biochem. Biophys. 307,85–90.
30. Takatsuka, J., Takahashi, N., and De Luca, L. M. (1996) Cancer Res. 58,675–678.

Second Series of Experiments

Recent Findings Concerning 9-cis Retinol Dehydrogenase Retinoic Acid Inhibits Human 9cRDH Activity. In order to understand whether retinoic acid can regulate 9-cis retinol dehydrogenase (9cRDH) activity, we carried out studies of the possible inhibitory effects of all-trans, 13-cis and 9-cis retinoic acid on human 9cRDH. The goal of the studies was to determine whether these retinoids regulate the activity of human 9cRDH. We were expecially interested in whether 9-cis retinoic acid, which is generated through oxidation of 9-cis retinaldehyde, the product of the 9cRDH reaction feedsback and inhibits 9cRDH activity. Indeed, as seen in Table II, these three different isomers of retinoic acid were potent inhibitors of 9cRDH activity. Especially striking is the inhibitory action of 13-cis retinoic acid. As seen in Table II, 13-cis retinoic acid inhibits 50% of 9cRDH activity when present at a concentration of 0.15 µM. This inhibitory concentration, although greater than physiologic concentrations by approximately 5-fold, is well within the range of plasma and tissue concentrations observed in humans and animal models receiving 13-cis retinoic acid for treatment of a number of clinical disorders. Both 9-cis and all-trans retinoic acid were also potent inhibitors of 9cRDH activity, although these two isomers are 15 to 30-times less potent than the 13-cis isomer. Since 13-cis retinoic acid is a far more potent inhibitor than the 9-cis and all-trans isomers, we asked whether the inhibitory effects of these isomers arises through isomerization to 13-cis retinoic acid during incubation (at 37° C. for 15 minutes) of the enzyme assay mixtures. As seen from Table III, this proved not to be the case. Although very small amounts of 13-cis retinoic acid were formed during the incubations, the concentration of 13-cis retinoic acid formed were not sufficient to account for the inhibitory actions of either all-trans or 9-cis retinoic acid.

In order to gain a better understanding of the specificity of this inhibition, we also investigated whether lipids with chemical structures similar to 1 3-cis retinoic acid also inhibited human 9cRDH. As shown in Table II, oleic acid, which has a cis double bond at the C-9 position of the 18 carbon fatty acid, was found to be a mild inhibitor of 9cRDH; approximately 100-fold less potent than 13-cis retinoic acid. Interestingly, the saturated fatty acid, palmitic acid, was not inhibitory towards 9cRDH. Taken together, this would suggest that a cis double bond is essential chemical feature for inhibition of human 9cRDH activity. The primary alcohols, oleyl alcohol, petroselinyl alcohol and all-trans retinol also did not inhibit 9cRDH activity. This suggests that that a carboxylic acid group is also necessary for 9cRDH inhibition.

The observation that 13-cis retinoic acid is a potent inhibitor of 9cRDH activity leads to several very important conclusions. First, since 13-cis retinoic acid is used clinically, it is possible that some of the toxicities observed in patients receiving 13-cis retinoic acid clinically may arise through the inhibition of 9cRDH activity. Considering that 13-cis retinoic acid is a poor transactivator of the retinoic acid receptors (RARs) and the retinoid X receptors (RXRs) and that it is generally assumed that 13-cis retinoic acid must be converted to all-trans retinoic acid in order to have activity, it has been difficult to understand why all of the toxicities observed for 13-cis retinoic acid do not overlap fully with those of all-trans retinoic acid. It seems possible that 13-cis retinoic acid is acting to down regulate 9cRDH activity and that this may in part account for some of the toxic actions of 13-cis retinoic acid. Since thousands of synthetic retinoids have been produced by the pharmaceutical industry, it is possible that assay of inhibitory effects on 9cRDH activity by these synthetic retinoids may serve as a rapid and useful in vitro assay for potential toxic effects in vivo by the synthetic retinoids. Secondly, considering the relatively low concentration of 13-cis retinoic acid needed to inhibit 9cRDH activity, it is also possible that 13-cis retinoic acid may play a role physiologically as a regulator of retinoic acid formation and degradation. If this working hypothesis proves correct, this may lead to the development of a new generation of drugs aimed at regulating retinoic acid formation in vivo.

Generation of Polyclonal Rabbit Antiserum Against Human 9cRDH. In order to investigate the cellular localization of human 9cRDH in tissues, we have generated a polyclonal antiserum against a synthetic peptide corresponding to amino acid residues 237 through 256. The specific sequence of this peptide is given in Table V. The amino acid residues were selected so as to have no overlap with other members of the family of short chain alcohol dehydrogenases, including the rat liver all-trans retinol dehydrogenases and the bovine retinal pigment epithelial 11-cis retinol dehydrogenase. The antiserum generated against this peptide is able to recognize a single protein band separated by SDS-polyacrylamide gel electrophoresis. The protein band recognized by Western blot analysis with this antiserum migrates with an approximate molecular weight of 32 kDa, the expected size of human 9cRDH. It should soon be possible to use this antiserum to identify the sites of 9cRDH expression in normal and diseased human tissues. Such identification could be useful in identifying disease states that may be either responsive or refractory to retinoic acid treatment.

Cloning and Expression of the Mouse Homolog for 9cRDH. We have recently obtained full length cDNA clones for the mouse homolog for 9cRDH. Three clones were obtained independently from mouse liver, kidney and testis cDNA libraries. Each of the clones have identical coding sequences which encode a protein which shares approximately 90% identity at the amino acid level with human 9cRDH. Interestingly, as can be seen from Table IV, the 5' noncoding regions of these cDNAs are different. It is possible that these differences are important in the regulation of 9cRDH expression.

TABLE II

ESTIMATED INHIBITOR CONCENTRATION RESULTING IN 50% INHIBITION OF HUMAN 9-CIS RETINOL DEHYDROGENASE ACTIVITY ($ID_{50}$)

|  | $Id_{50}$ (µM) |
| --- | --- |
| 13-cis Retinoic Acid | 0.15 |
| 9-cis Retinoic Acid | 2.6 |
| all-trans Retinoic Acid | 4.6 |
| all-trans Retinol | >10.0 |
| Oleic Acid | 15.0 |
| Palmitic Acid | >100.0 |
| Oleyl Alcohol | >100.0 |
| Petroselinyl Alcohol | >100.0 |

TABLE III

ISOMERIZATION OF RETINOIC ACIDS IN THE HUMAN 9-CIS RETINOL DEHYDROGENASE ASSAY

| Inhibitor | all-trans | 13-cis | 9-cis |
| --- | --- | --- | --- |
| 10 µM all-trans Retinoic Acid at start:: | 100% | — | — |
| all-trans Retinoic Acid at end: | 98.8% | 0.8% | 0.4% |
| 1 µM 13-cis Retinoic Acid at start: | — | 100% | — |
| 13-cis Retinoic Acid at end: | 1.6% | 98.4% | — |
| 10 µM 9-cis Retinoic Acid at start: | — | — | 100% |
| 9-cis Retinoic Acid at end: | 4.2% | 1.1% | 94.7% |

TABLE IV

SEQUENCE ANALYSIS OF cDNA CLONES FOR MOUSE 9-CIS RETINOL DEHYDROGENASE OBTAINED FROM LIVER, KIDNEY AND TESTIS cDNA LIBRARIES

| | |
|---|---|
| Liver: | CGCCAGTGTGCTGGAATTCGGCACGAGGCTTAGCTGTAGCTAG |
| Kidney: | ............................................ |
| Testis: | TGCCCATAATCTGTTTCACACAATAAGCCATAGCTTGCCAAGCA |
| | |
| Liver: | TGTGGGAGCCTGGGAAGTCTAGGAGCAAAGTCTCTCA<u>AGCAGA</u> |
| Kidney: | .........TGGCTCNGAGGCCAAGANTCGGACCATG<u>AGCAGA</u> |
| Testis: | TATAGTCTCATCTGCTCAGACCAGACATTTCCAGCTAAGTAAAT |
| | |
| Liver: | <u>CAGAAAGCTACAGCTTCACACATTGTGTTGCCTGCCAGCTTTCC</u> |
| Kidney: | <u>CAGAAAGCTXXAGCTTCACACATTGTGTTGCCTGCCAGCTTTCC</u> |
| Testis: | GTTAGGGGCCAAGGCTAAAGGGGTAGAGGAAATGACAAGTTTT |
| | |
| Liver: | <u>CCAGXXAGXXXXXGCTGCCCTCAGCAGGGCATCTCATCCCATC</u> |
| Kidney: | <u>CCAGXXAGCCTAGGCTGCCCTCAGCAGGGCATCTCATCCCATC</u> |
| Testis: | CCTGCCCAGCCTAA<u>GCTGCCCTCAGCAGGGCATCTCATCCCATC</u> |
| | |
| Liver: | ATGTGGCTGCCTCTGCTTCTGGGTGCCTTGCTGTGGGCAGTGCT |
| Kidney: | ATGTGGCTGCCTCTGCTTCTGGGTGCCTTGCTGTGGGCAGTGCT |
| Testis: | ATGTGGCTGCCTCTGCTTCTGGGTGCCTTGCTGTGGGCAGTGCT |
| | |
| Liver: | GTGGTTGCTCAGAGACCGGCAGAGCCTGCCGGCCA................ |
| Kidney: | GTGGTTGCTCAGAGACCGGCAGAGCCTGCCGGCCA................ |
| Testis: | GTGGTTGCTCAGAGACCGGCAGAGCCTGCCGGCCA................ |

TABLE V

SYNTHETIC PEPTIDE USED TO GENERATE RABBIT ANTISERUM AGAINST HUMAN 9-CIS RETINOL DEHYDROGENASE

| | |
|---|---|
| Sequence Chosen for Use in Immunization: | Amino Acid Residues 237 to 256 (319 total) |
| Sequence: | HYGGAFLKYLKMQQRIMNLI |

Third Series of Experiments

Introduction 9-cis-retinol dehydrogenase (9cRDH) has recently been identified and it is proposed that it plays an important role in the synthesis of the transcriptionally active retinoid, 9-cis-retinoic acid. There is little information available regarding either the biochemical properties of 9cRDH or its gene. Here reported are studies of the properties and expression of human and mouse 9cRDH and of the characteristics and location of the murine-9cRDH gene. These studies indicate that human and mouse 9cRDH have similar substrate specificities for cis-isomers of retinol and retinaldehyde and that both show marked sensitivity to inhibition by 13-cis-retinoic acid. h9cRDH and m9cRDH activities are inhibited by approximately 50% when 0.15 μM 13-cis-retinoic acid is included in the assay mixture (for substrate concentrations of 10 μM). This potent inhibition of 9cRDH activity is seen for 13-cis- but not for 9-cis- or all-trans-retinoic acids. Neither human nor mouse 9cRDH is able to use 3α-hydroxy- or 17β-hydroxysteroids as substrates. Immunoblot analysis using antiserum directed against a peptide from h9cRDH demonstrates 9cRDH expression in several human tissues obtained from an 11-week old fetus. In situ hybridization studies indicate that 9cRDH mRNA is expressed in the floor of the fourth ventricle and the roof plate of the neural tube in the 12.5 day mouse embryo. Adult mouse brain, liver, kidney and to a lesser extent small intestine and placenta were shown to express 9cRDH. The murine 9cRDH gene was found to consist of at least 5 exons and to span approximately 6 kb of genomic DNA. Backcross analysis mapped the mouse 9cRDH gene to the most distal region of mouse chromosome 10. Taken together, these data extend our understanding of the properties and distribution of 9cRDH and provide additional support for our hypothesis that 9cRDH plays an important role in 9-cis-retinoic acid formation.

The abbreviations used herein are defined as follows: RAR, retinoic acid receptor; RXR, retinoid X receptor; 9cRDH, 9-cis-retinol dehydrogenase; SCAD, short chain alcohol dehydrogenases; RDH, retinol dehydrogenase; 11cRDH, 11-cis-retinol dehydrogenase; HPLC, high performance liquid chromatography; MAP, multiple antigen peptide; and PBS, 10 mM sodium phosphate, pH 7.4, 150 mM NaCl.

Retinoids are acquired from the diet and are needed for maintaining the general health of higher animals and humans (1). They are required for normal vision, for maintaining normal growth and differentiation, for an uncompromised immune response, for normal male and female reproduction and for other essential biologic processes (1–5). Retinoids act primarily as ligands for transcription factors which modulate expression of a large number of genes including those encoding hormones, growth factors, transcription factors, membrane receptors, extracellular matrix proteins, structural proteins and enzymes involved in diverse metabolic processes (4, 5). The transcriptional regulatory actions of retinoids are thought to be mediated primarily through the actions of all-trans- and 9-cis-retinoic acid which respectively bind to members of the retinoic acid receptor (RAR) and retinoid X receptor (RXR) families of ligand dependent transcription factors (4). Since members of the RXR family of receptors are able to serve as partners in forming heterodimers with the vitamin D receptor, the thyroid hormone receptors, the peroxisomal proliferator activator receptors and several other ligand dependent transcription factors, 9-cis-retinoic acid likely plays an important role in regulating a broad-spectrum of hormonally responsive genes (4).

The metabolism of retinoic acid within tissues is complex and includes both the activating metabolism of retinol to retinoic acid and the oxidative and conjugative metabolism of retinoic acid to more polar metabolites (6, 7). Retinoic acid is formed from retinol through two enzymatic oxidations, in a manner analogous to ethanol oxidation. The first of these oxidation reactions involves the oxidation of retinol to retinaldehyde. Members of two families of alcohol dehydrogenases are actively being investigated as possible physiologically relevant candidates for in vivo catalysis of retinol oxidation (6, 7). The first family consists of the relatively abundant cytosolic class I and class IV alcohol dehydrogenases. Data that support in vivo involvement of these enzymes in retinoic acid formation include demonstrations of overlapping temporal and spatial patterns of retinoic acid presence and enzyme expression in tissues of the developing mouse embryo (8, 9) Several members of a second family of enzymes, the short-chain alcohol dehydrogenases (SCAD), are also being investigated, as possibly essential for retinoic acid formation (10–19). Members of the SCAD family also are thought to be importantly involved in steroid and eicosinoid metabolism (20, 21). At present, there is not general agreement regarding the importance of members of each of these enzyme families in catalyzing retinol oxidation in vivo (7–19). However, based on the relatively large number of enzymes that can catalyze retinol oxidation, it would appear likely that there is redundancy in the enzymatic machinery needed for retinoic acid formation.

Previously described was an enzyme, termed 9-cis-retinol dehydrogenase (9cRDH), that is present in several human tissues including mammary tissue, kidney, liver, and testis (19). Based on the substrate specificity of this enzyme, it was proposed that human 9cRDH plays an important role in the formation of 9-cis-retinoic acid, by catalyzing the oxidation of 9-cis-retinol to 9-cis-retinaldehyde. Others recently have reported the cloning of a sterospecific mouse retinol dehydrogenase (RDH) with 9-cis-retinol dehydrogenase activity and have characterized the expression pattern of this enzyme in some embryonic and adult mouse tissues (22, 23). This series of studies extends the prior studies of 9cRDH by providing detailed biochemical characterizations of human and mouse 9cRDH, by describing 9cRDH distribution in fetal human and mouse tissues and by characterizing the mouse gene for 9cRDH.

Experimental Procedures

Retinoids and chemicals. All-trans-retinol, all-trans-retinoic acid, 13-cis-retinoic acid, 9-cis-retinoic acid and 11-cis-retinaldehyde were obtained as gifts of Dr. Christian Eckhoff of Hoffmann-La Roche, Inc. (Nutley, N.J.). All-trans-, 13-cis- and 9-cis-retinaldehyde and 13-cis-retinol were purchased from Sigma Chemical Co. (St. Louis). 9-Cis- and 11-cis-retinol were synthesized through $NaBH_4$ reduction of the corresponding retinaldehyde (24). The resulting 9-cis- or 11-cis-retinol was purified by normal phase HPLC essentially as described for 11-cis-retinol purification (24).

Steroids used for the studies were purchased from Sigma. These include androsterone, testosterone, estrone, β-estradiol, 4-androstene-3,17dione, 5α-androstane-3,17dione, 5α-androstane-3α, 17βdiol, 5α-androstane-3β, 17βdiol, 5αandrostan-17βol-3one, cortisone, corticosterone, hydrocortisone, prednisone, and progesterone. NADH, $NAD^+$, citral, disulfuran, phenylarsine oxide, carbenoxolone, 4-methylpyrazole and 1,10-phenanthroline were also obtained from Sigma. Oleyl and petrosenlinyl alcohols and palmitic and oleic acids were obtained from Nu-Chek Chemicals (Elysian, Minn.).

HPLC and other organic solvents, all HPLC grade, were purchased from Fisher Chemical Company (Pittsburgh, Pa.). Other reagents used in these studies were purchased from standard commercial sources.

Enzymatic Assays. Assays for human and mouse 9cRDH were carried out essentially as were described previously for human 9cRDH (19). For expression of mouse 9cRDH a cDNA clone obtained from a mouse liver cDNA library was employed (see below). Recombinant human or mouse 9cRDH expressed in CHO cells was incubated in an assay mixture containing 10 µM 9-cis-retinol (added in 0.02 mL ethanol) and 2 mM NAD in 10 mM Hepes, pH 8.0, containing 150 mM KCl, 1 mM EDTA, and 50 µg phosphotidyl choline for 15 min at 37° C. (final assay volume of 0.6 ml) with agitation. This assay mixture was used routinely to measure oxidation of 9-cis-retinol to 9-cis-retinaldehyde and in studies assessing oxidation of 11-cis-, 13-cis- and all-trans-retinol to their corresponding aldehydes. For some experiments, the ability of human or mouse 9cRDH to catalyze the reduction of 9-cis-, 11-cis-, 13-cis- or all-trans-retinaldehyde was assessed. To assess these reduction reactions, incubations were carried out in 100 mM sodium acetate, pH 5.0, containing 50 µg phosphotidyl choline and 2 mM NADH (or 2 mM NADPH) in a final volume of 0.6 ml for 15 min at 37° C.

Immediately following incubation of the assay, the assay mixture was denatured with an equal volume of absolute ethanol (0.6 ml), and the retinoids extracted into 2.5 ml of hexane. Following one backwash of the hexane extract with 0.5 ml of deionized water, the hexane was evaporated to dryness under a gentle stream of $N_2$. The extracted retinoids were immediately redissolved in 120 µl of hexane and analyzed by normal phase HPLC as described below.

To investigate whether human or mouse 9cRDH will catalyze oxidations or reductions of 3α-hydroxy-, 11β-hydroxy- or 17β-hydroxysteroids, these steroids were incubated at 37° C. for 1.5 h in the assay media described above for assessing oxidation/reduction of 9-cis-retinol/9-cis-retinaldehyde. The Hepes $NAD^+$-containing assay buffer described above was employed to assess hydroxysteroid oxidation and to assess hydroxysteroid reduction the acetate buffer containing NADH (or NADPH) assay buffer (see above) was employed. Immediately following incubation, the steroids were extracted as described above for retinoids. The final hexane extract was evaporated to near dryness and this was spotted onto a silica high performance TLC plate (Whatman Inc., Clifton, N.J.) and developed in hexane/diethyl ether/acetic acid (70:30:1, v/v) or ethyl acetate/chloroform (25:75, v/v). Steroids were visualized by charring after treatment of the TLC plates with an areosol of 10% (v/v) $H_2SO_4$ in methanol.

Inhibition Studies of 9cRDH Activity. For the inhibition experiments, each potential inhibitor tested was added to the recombinant 9cRDH in 5 µl of ethanol in the presence of 2 mM $NAD^+$, 10 mM Hepes, pH 8.0, containing 150 mM KCl, 1 mM EDTA, and 50 µg phosphotidyl choline (assay incubation mixture lacking the retinoid substrate). This mixture was allowed to sit on ice for 5 minutes prior to adding substrate. Upon addition of 10 µM 9-cis-retinol (final concentration), the mixture was incubated for 15 minutes at 370° C. with agitation and extracted as described above for the standard enzyme assay. HPLC Procedures. Stereoisomers of both retinol and retinaldehyde were separated on a 4.6×15-mm Supelco (Belefonte, Pa.) LC-SI Supelcosil™ column using hexane:ethyl acetate:butanol (96.9:3:0.1 v/v) as the mobile phase flowing at 0.8 ml/min. A silica guard column (Supelco) preceded the running column. Retinols and retinaldehydes were detected using a Waters 996 Photodiode array detector at absorbances of 325 and 365 nm, respectively. Retention times for all-trans-, 9-cis-, 11-cis-, and 13-cis-retinols and corresponding retinaldehydes were established using the purified compounds obtained as described above. Quantities of each retinol and retinaldehyde isomer present in extracts were determined by comparisons of the integrated areas under the HPLC peaks with a standard curve constructed relating integrated peak area with known masses of each retinoid isomer. The concentration of each retinoid isomer were determined by UV-visible spectrophotometry using published extinction coefficients for each retinol, retinaldehyde or retinoic acid isomer (25).

Antibody production. A peptide corresponding to amino acids 236–257 of the primary sequence of human 9cRDH sequence (19) was synthesized by the Columbia University Howard Hughes Protein Core Facility. The peptide was linked to an eight armed matrix (26) and this multiple antigen peptide (MAP) served as the immunogen. The MAP was sent to Pocono Rabbit Farm & Laboratory, Inc., Canadensis, Pa., for antibody production. For this purpose, a New Zealand White rabbit was injected intradermally with 1 mg of MAP in Complete Freund's Adjuvant. One booster intradermal injection of 100 µg of MAP in Complete Freund's Adjuvant was given on day 14. On day 28, the rabbit was given a subcutaneous injection of 100 µg of the MAP in Incomplete Freund's was given. Test bleeds began 42 days after the initial injection, followed by injection of 50 µg of MAP in Incomplete Freund's Adjuvant on day 56 and every four weeks thereafter. Test bleeds were taken two weeks after each injection (days 42, 70 and 98). On day 126 after the initial immunization, the rabbit was exsanguinated.

Immunoblot analyses. For immunoblot analyses, tissues or cells were homogenized in 10 mM Tris-HCl, pH 7.4 using a Polytron homogenizer (Brinkmann Instruments, Westbury, N.Y.) Debris and unhomogenized materials were removed from the homogenate through centrifugation of the crude homogenate at 800×g at 4° C. for 10 min. To an aliquot of homogenate containing 100 µg total protein, 6×-SDS treatment buffer (0.35 M Tris-HCl pH 6.8, 10.28% SDS, 36% (v/v) glycerol, 0.6 M DTT, 0.012% (w/v) bromophenol blue) was added and, following brief vortexing, the mixture was boiled at 1000° C. for 10 min. The treated homogenate was loaded onto a 15% SDS-PAGE gel and electrophoresised at 150 mV until the tracking dye reached the bottom of the gel. Proteins were transferred from the 15% SDS-PAGE gel onto a nitrocellulose membrane at 30 volts and 4° C. for 12 hours. The nitrocellulose membrane was subsequently blocked with 5% non-fat dry milk in 10 mM sodium phosphate containing 150 mM NaCl at pH 7.4 (PBS) for 1 h, followed by incubation in the presence of the rabbit polyclonal anti-h9cRDH antiserum at a 1:5000 dilution in PBS containing 0.2% Tween 20. The membrane was washed 4-times with PBS containing 0.2% Tween 20 for 15 minutes and then incubated for 1 h at room temperature in PBS containing 0.2% Tween 20 and a 1:1000 dilution of a second antibody consisting of donkey-anti-rabbit IgG conjugated to alkaline phosphatase (Amersham, Chicago Ill.). After incubation with the secondary antiserum, the nitrocellulose membrane was again washed 4-times for 15 min each with PBS containing 0.2% Tween 20. All washes and incubations were carried out with constant orbital agitation. Immunoblots were visualized on photographic films using the ECL kit purchased from Amersham (Amersham, Chicago Ill.), following the supplier's instructions.

Human fetal tissues were obtained from several first trimester fetuses through the Laboratory for the Study of Human Embryos and Fetuses, University of Washington, Seattle, Wash. These consisted of mixed adrenal and small intestine tissue from an 11 week fetus, lung tissue from a 10 week fetus and brain and limb tissue from an 8 week old fetus. These tissue samples had been frozen at −70° C. prior to use for our studies. For immunoblot analysis, these fetal tissues were processed as described above.

Sources of mouse tissues, RNA and $^{32}$P-probes. Normal mouse tissues were obtained from adult Swiss Webster mice (Charles River, Wilmington, Del.). Embryos were obtained from timed pregnant Swiss Webster mice. Dissected tissues were frozen in liquid $N_2$ prior to RNA isolation. Tissues and embryos for in situ hybridization analyses were fixed in 4% paraformaldehyde in phosphate-buffered saline (PBS) at 4° C. overnight.

The cDNA corresponding to the human 9cRDH (19) was used as the probe for screening the mouse cDNA libraries. A cDNA corresponding to the murine 9cRDH was used as the probe for screening a mouse genomic DNA library and for northern blot and in situ hybridization analyses. DNA probes for the cDNA and genomic library screening were labeled with [α-$^{32}$P]dCTP using the random primer DNA labeling kit (Amersham, Arlington Heights, Ill.). Riboprobes were prepared using T7 or T3 RNA polymerases in the presence of [a-$^{32}$P]UTP for northern blot hybridization analysis and [a-$^{35}$S]UTP for in situ hybridization analysis. All radioactive nucleotides used in this study were obtained from New England Nuclear (Wilmington, Del.).

Screening of cDNA libraries. Two mouse cDNA libraries were screened to obtain a cDNA clone for mouse 9cRDH, an adult mouse testis cDNA library and a day 14 mouse testis cDNA library. The libraries were generated using the Uni-Zap XR cDNA synthesis kit (Stratagene, La Jolla, Calif.) and were the generous gift of Dr. Kunsoo Rhee (Columbia University) (27). The cDNA libraries were screened according to standard protocols (28). The hybridization conditions were: 500 mM NaCl, 50 mM Tris (pH 8.0), 5 mM EDTA, 1× Denhardt's solution, 100 ug/ml salmon sperm DNA, 1% SDS at 55° C. over night. The final washing conditions were: 0.2×SSC, 0.1% SDS at 55° C. 30 min. For each library, 6×10$^5$ plaques were screened. Positive clones were plaque purified twice and inserts from the tertiary screen were in vivo-excised following the protocol provided by Stratagene. The phagemids contained the cDNA at the EcoRI and XhoI site of pBluescript SK⁻. Clones isolated from these screens were sequenced using an Applied Biosystems Model 373A DNA sequencer (Applied Biosystems, Foster City, Calif.).

Screening of a genomic library. A genomic library from mouse strain 129SV/J (Stratagene, constructed in λ Fix II vector) was screened using a 1.4 kb cDNA corresponding to 9cRDH isolated from an adult mouse testis cDNA library. The conditions were identical to those used in the cDNA library screening except that the hybridization and final washing temperature was 65° C. λ DNA was prepared according to standard protocols (28). Briefly, after cell lysis, the culture was treated with DNase I and RNase A and centrifuged. The phage in the supernatant were precipitated by PEG 8000 and centrifuged. The phage particle were disrupted in SDS, EDTA at 65° C. and then phenol-extracted (2-times) and phenol-chloroform extracted. Single and double enzyme digestion was performed according to the manufacturer's recommended conditions.

Chromosome mapping. A genomic polymorphism in the murine 9cRDH gene was identified between samples of DNA from *M. musculus* strain C57Bl/6J and M. spretus. A small intron was selected as the marker region and a pair of primers was synthesized for use in PCR amplification of this intron. The Backcross DNA Panel and Service provided by The Jackson Laboratory (Bar Harbor, Me.) was used for mapping the chromosomal site of 9cRDH. PCR analysis using the primer pairs was performed on the panel DNA and the products were electrophoresised on agarose gels and stained with ethidium bromide. The presence of specific PCR products was noted and the data submitted to The Jackson Laboratory for chromosomal assignment.

Northern blot hybridization analysis. Total RNA was isolated using standard procedures (29). Samples consisting of 10 µg of total RNA were electrophoresesed on 0.8% agarose gels containing 2.2 M formaldehyde at 1 v/cm overnight. Ethidium bromide staining of the 18S and 28S RNAs was used to demonstrate equal loading for each sample. After electrophoresis the gels were soaked in 20×SSC for 1 h and blotted overnight onto a nitrocellulose membrane using 10×SSC. The RNA was transferred to nitrocellulose membranes and baked at 80° C. in a vacuum oven for 2 h. The cRNA probe was labeled using T7 RNA polymerase and [α-$^{32}$P]UTP. Hybridization was carried out at 65° C. in 5×SSC, 20 mM sodium phosphate buffer (pH 7.0), 60% formamide, 1% SDS, 5× Denhardt's solution, 100 µg/ml salmon sperm DNA, 100 µg/ml yeast RNA, and 7% dextran sulfate overnight. After hybridization, the final wash was at 80° C. in 0.2×SSC and 0.1% SDS for 1 h.

In situ hybridization analysis. Day 12.5 embryos were removed from Swiss Webster mice and fixed with 4% paraformaldehyde in phosphate buffered saline (PBS), pH 7.4 at 4° C. overnight according to standard procedures (30). Fixed tissues were washed sequentially for 0.5 h each in PBS, saline, saline/50% ethanol, and then 70% ethanol and stored in 70% ethanol until paraffin embedding. Sections of 6 µm thickness were cut, the paraffin was removed by xylene treatment and sections rehydrated through immersion in an ethanol series. In situ hybridization was performed according to standard procedures (31). For cRNA probe synthesis, sense and anti-sense probes were transcribed using either T3 or T7 RNA polymerase, and labeled using [a-$^{35}$S]UTP. Slides were exposed to emulsion (Kodak type NTB-2) for 2–4 weeks, developed, stained with hematoxylin and eosin, mounted and viewed in a Leitz photo-microscope under bright-field and epiluminescence optics.

Results

Generation and characterization of antiserum to human 9cRDH. In order to characterize the distribution of human 9cRDH in tissues and the biochemical properties of this enzyme, a rabbit polyclonal antibody that recognizes human 9cRDH was generated. This antiserum was made against a multiple antigen peptide consisting of amino acids 236 to 257 of the human 9cRDH (21 out of 319 amino acids) (19). The sequence of this peptide is provided in Table VI. The peptide was chosen to serve as an antigen for two reasons. First, this peptide shows the greatest number of amino acid differences when compared with other closely related members of the SCAD family which share homology with human 9cRDH (Table VI). Thus, for this region, the human 9cRDH shows 6 out of 21 amino acid differences with mouse 9cRDH (see below), 5 amino acid differences with bovine 11cRDH (15, 16), 15 differences with rat liver all-trans retinol dehydrogenase type I (13), 14 differences with rat liver all-trans retinol dehydrogenase, type II (14), 15 differences with rat liver all-trans retinol dehydrogenase, type III (12) and 15 differences with the mouse liver cis-retinol dehydrogenase (18). A second reason for selecting this peptide as an antigen was that computer analysis using an amphipathic profiler indicated that this sequence scored high on an antigenicity scale.

TABLE VI

Amino acid homologies of the peptide sequence used to generate antibodies to human 9cRDH[1,2].

| Enzyme | AA[3] | | AA[3] |
|---|---|---|---|
| h9cRDH | 236 | H Y G G A F L T K Y L K M Q Q R I M N L I | 257 |
| m9cRDH | 236 | H Y G E A F L D T Y L R V Q R R I M N L I | 257 |
| b11cRDH | 236 | L Y G E A F L T K Y L R V Q Q R I M N M I | 257 |
| rRoDH-I | 237 | I Y G E K F Q D S Y M K A M E S L V N T C | 258 |
| rRoDH-II | 237 | V Y G E N Y L A S Y L K M L N G L D Q R C | 258 |
| rRoDH-III | 237 | I Y G E K F R D S Y M K A M E S L V N M C | 258 |
| mCRAD | 237 | I Y G E K Y L A S Y L K R L N K L D K R C | 258 |

[1]Residues that are different from those of the human 9cRDH are underlined.
[2]Enzyme designations are: h9cRDH, human 9-cis-retinol dehydrogenase (19); m9cRDH, mouse 9-cis-retinol dehydrogenase (present report); b11cRDH, bovine 11-cis-retinol dehydrogenase (15); rRoDH-I, rat retinol dehydrogenase, type I(13); rRoDH-II, rat retinol dehydrogenase, type II(14); rRoDH-III, rat retinol dehydrogenase, type III (12); and mCRAD, cis-retinol dehydrogenase (18).
[3]AA provides the starting and ending amino acid residues.

Immunoblot analysis showed that the antiserum recognizes strongly and specifically recombinant human 9cRDH as a 32 kDa protein (the correct size predicted from the cDNA for human 9cRDH) (FIG. 5). Recognition of this protein band was effectively competed by preincubation of the antiserum with the peptide antigen (200 µg MAP in 20 ml blocking buffer). As can be seen from FIG. 5, neither sham-transfected CHO cell homogenates nor homogenates from CHO cells transfected with the mouse 9cRDH cDNA contained protein(s) recognized by this antiserum. Since the size of the protein recognized by the antiserum separated on the SDS-PAGE gel corresponds to a protein with a mass of 32 kDa, the mass of human 9cRDH predicted by its cDNA, it would appear that 9cRDH does not undergo substantial post-translational modification upon expression in CHO cells and further, that such modification is not essential for 9cRDH activity.

Upon incubation of recombinant human 9cRDH for 15 min at 37° C. with up to 25 µl whole rabbit antiserum followed immediately by human 9cRDH enzyme assay, no differences in 9cRDH activities were observed for the mixtures containing or not containing the antiserum (data not shown). Thus, the rabbit anti-human 9cRDH antiserum does not inhibit human 9cRDH enzymatic activity. This could suggest that the peptide used for generating the antiserum resides at a site on the human 9cRDH molecule removed from the catalytic center of the enzyme.

Immunoblot analysis of 9cRDH distribution in fetal human tissues. Using the anti-human 9cRDH antiserum described above, immunoblot analyses of the expression of 9cRDH in human fetal tissues were carried out. Immunoblot analysis of human fetal tissue homogenates indicates that 9cRDH is expressed in the first trimester of human pregnancy. A representative immunoblot for tissues from an 11 week-old human fetus is provided in FIG. 5. As can be seen from FIG. 5, 9cRDH is expressed in several fetal tissues including pooled samples of fetal adrenals+small intestine and small intestine+brain+lungs. Since only pooled human fetal tissues were available for this experiment, it was not possible to discriminate among which tissues expressed 9cRDH at 11 weeks gestation. Replicate immunoblot analyses of several tissues from a different 1'-week-old human fetus indicated that 9cRDH is also expressed during the first trimester in spinal cord but not muscle (data not shown).

Isolation of cDNAs for mouse 9cRDH. Since 9cRDH is expressed in the human adult testis, an adult mouse testis cDNA library and a day 14 mouse testis cDNA library for clones for mouse 9cRDH were chosen for screening. A total of approximately 106 plaques were screened over a series of two experiments. Six positive cDNA clones for mouse 9cRDH were identified and characterized upon screening the libraries with a probe generated from the cDNA for human 9cRDH. Sequence analysis revealed that all six clones were indeed murine homologues of human 9cRDH but were either incomplete or exhibited abnormal splicing. As is shown diagramatically in FIG. 6C, one of the testis cDNA clones has 58 bp of intron 3 and 222 bp of intron 1 unspliced (see details regarding the mouse 9cRDH gene below). This clone did not extend to the first exon. A second testis clone has 340 bp of unspliced intron 3 did not extend to exon 3. A third testis clone did not contain any intron sequences but was missing the translation initiation codon. All unspliced intron sequences belonged to the 3' region of the intron and were adjacent to the 5' end of the next exon. Also obtained were two cDNA clones from the mouse EST data bank, one derived from a liver cDNA library and one from a kidney library. Based on the human 9cRDH cDNA, the liver clone appeared to be nearly full-length (1281 bp). It has a 957 bp-coding region corresponding to a protein of 319 amino acids, a 123 bp 3' untranslated region, and a 199 bp 5' untranslated region. The kidney clone was nearly identical to this liver clone except that the first 5 bp of intron 1 were unspliced. Sequences for the mouse liver 9cRDH cDNA (Accession No. AF033196) and mouse kidney 9cRDH cDNA (Accession No. AF033195) have been deposited with, and are available through, the NCBI Genbank.

Figure 7B:
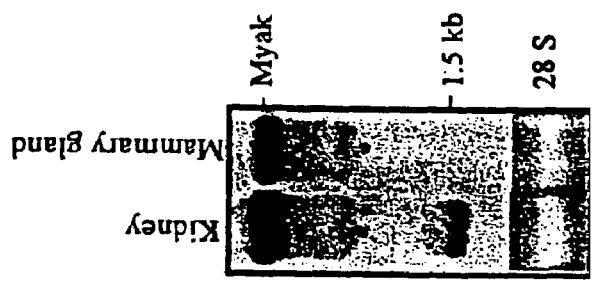
FIG. 7. Northern blot analysis of 9cRDH expression in mouse tissues. RNA was isolated from adult mouse brain, heart, kidney, lung, testis, ovary, placenta, uterus, liver, spleen, small intestine, a day 12.5 mouse embryo, and mammary gland. Each lane contains 10 µg of total RNA. For assessing 9cRDH expression in mouse mammary gland, kidney RNA was used as positive tissue control for 9cRDH expression and another gene, Myak, which is known to be expressed in mouse mammary tissue, was hybridized at the same time as a control for the quality of the mammary tissue RNA.
Figure 7A:
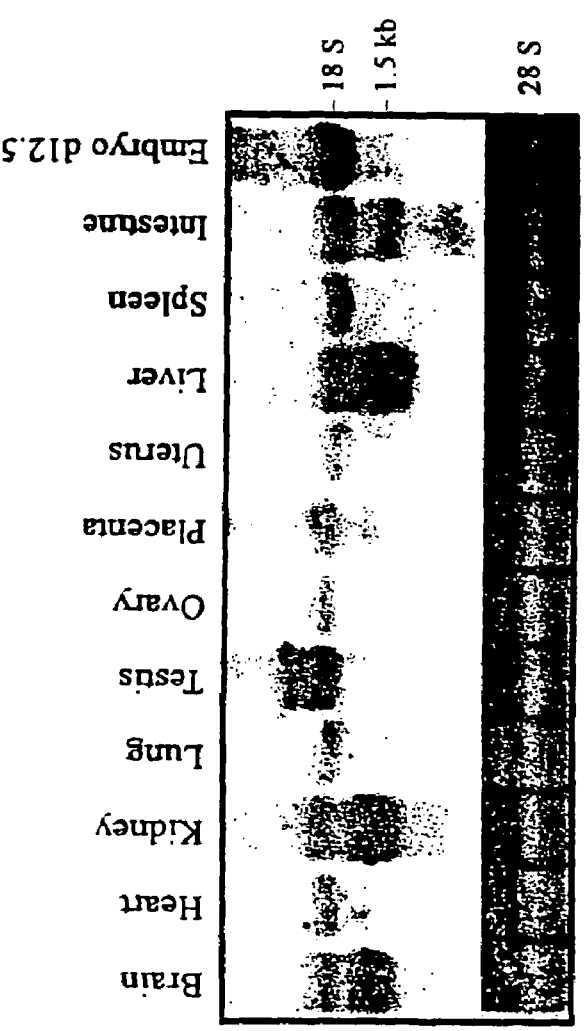

Isolation and characterization of the murine 9cRDH gene. To elucidate the organization of the mouse and human cDNAs and their corresponding genes, mouse 9cRDH genomic sequences were isolated. Approximately 106 plaques of a genomic library from mouse strain 129SV/J were screened over a series of two experiments using a probe generated with the mouse testis 9cRDH cDNA. Four potential genomic clones were identified, subcloned, mapped for restriction sites, and characterized with regard to the position of exons. The clones span approximately 30 kb of DNA in total. Two of the clones contained exons corresponding to the 5' region of the mouse 9cRDH cDNA; one contained 3' exons, and the fourth contained the entire 9cRDH gene. All of the coding exons for the mouse 9cRDH cDNA were mapped to the genomic clone and sequenced. Exon-intron boundaries were confirmed at the sequence level. The murine 9cRDH gene has at least five exons and spans approximately 6 kb of genomic DNA. The largest intron, intron 3, is approximately 3.5 kb and the smallest, intron 2, is 114 bp. The other introns include intron 1 of 554 bp and intron 4 of 198 bp. The sizes of the five exons are: exon 1, 167 bp (this exon may be incomplete); exon 2, 342 bp; exon 3, 259 bp; exon 4, 164 bp; and exon 5, 349 bp. The translation initiation codon is contained within exon 2. Although it is possible that additional exons exist in the 5' genomic DNA, they would not be very large as the cDNAs obtained for mouse 9cRDH are close in size to the transcripts observed in tissues examined to date (see below). The genomic organization data are summarized in FIGS. 6A and B. Northern blot analysis of 9cRDH expression in mouse tissues. Northern blot analysis of adult mouse tissues revealed that 9cRDH transcripts are most readily detected in RNA from kidney, liver, and brain and at somewhat lower levels in intestine and placenta (FIG. 7). The transcript identified by Northern blot analysis was approximately 1.5 kb, a size that agrees well with that predicted by the size of the longest of the murine 9cRDH cDNA clones. In testis, a band migrating between the 18S and 28S rRNAs (at approximately 3.5 kb) was detected. Given the heterogeneous cDNAs isolated from the testis libraries (see above), this transcript may arise from differential splicing.

In situ hybridization analysis of 9cRDH expression during mouse embryogenesis. Embryos were collected at day 12.5 of gestation (E12.5) and examined by in situ hybridization for the sites of expression of 9cRDH. Examination of sagittal and transverse sections through the thoracic region has revealed that 9cRDH expression was most readily detected in the floor of the fourth ventricle and the roof plate of the neural tube (FIG. 8). The region of expression appeared as a narrow stripe on the dorsal neural tube, which has closed at this position in the embryo at this stage of development.

Substrate specificity of mouse 9cRDH. The liver 9cRDH cDNA was expressed in CHO cells in order to characterize the biochemical properties of mouse 9cRDH. The specific activities of recombinant human and mouse 9cRDH expressed in CHO cells for 9-cis-, 13-cis-, 11-cis- and all-trans-retinol oxidation along with those obtained for 9-cis-, 13-cis-, 11-cis- and all-trans-retinaldehyde reduction are provided in Table VII. $NAD^+$ and NADH were much more effective than $NADP^+$ and NADPH in serving as cofactors for these reactions (data not shown). For no substrate, could equimolar concentrations $NADP^+$/NADPH support reaction rates greater than 10% of those observed for $NAD^+$/NADH. With regards to substrate and cofactor specificity, mouse 9cRDH is very similar to human 9cRDH (19). The sole substantial difference observed between the mouse and human enzymes, for the assay conditions that wree used, was that the mouse enzyme catalyzes 9-cis-retinol oxidation at 2-times the rate of oxidation of 11-cis-retinol. This is different from human 9cRDH which catalyzes 11-cis-retinol oxidation at a slightly greater rate than 9-cis-retinol oxidation (see Table VII). Interestingly, both human and mouse 9cRDH demonstrate a high activity towards 13-cis-retinaldehyde reduction but neither will catalyze significant rates of 13-cis-retinol oxidation.

TABLE VII

Substrate preference of human and mouse 9-cRDH for isomers of retinol and retinaldehyde.[1,2,3]

| Substrate | h9cRDH | m9cRDH |
|---|---|---|
| | pmol/min/mg protein | |
| 9-cis-retinol | 367 | 328 |
| 11-cis-retinol | 442 | 152 |
| 13-cis-retinol | 0.3 | 2.0 |
| all-trans-retinol | 0.5 | 0.6 |
| 9-cis-retinaldehyde | 268 | 420 |
| 11-cis-retinaldehyde | 1220 | 506 |
| 13-cis-retinaldehyde | 744 | 748 |
| all-trans-retinaldehyde | 1.1 | 1.3 |

[1]cDNAs for human (h9cRDH) and mouse (m9cRDH) 9cRDH were expressed in CHO cells and protein from CHO cell homogenates was used as the source of h9cRDH and m9cRDH activity.
[2]All assays were carried out under conditions (time = 15 min; protein = 150–180 μg/assay; and substrate = 10 μM) which gave linear rates of product formation.
[3]Data reported in this table represent the means obtained from duplicate assays carried out using the same CHO cell homogenate protein. Replicate assays were carried out on two or three separate occasions using different sources of transfected CHO cell proteins. These replicate determinations gave similar specific activity values to those reported.

Biochemical characterizations of human and mouse 9cRDH. Using recombinant human and mouse 9cRDH expressed in CHO cells as a source of enzymatic activity, a series of biochemical characterizations of the enzyme was carried out. Ffirst investigated was whether reagents which inhibit other SCADs or alcohol dehydrogenases also inhibit human or mouse 9cRDH activity. Study of the effects of phenylarsine oxide (15 μM final concentration), carbenoxolone (0.5 mM), 1,10-phenanthroline (1 mM), 4-methylpyrazole (1 mM), citral (1 mM final concentration), disulfuran (1 mM final concentration) and zinc acetate (1 mM final concentration) indicated that none of these compounds influenced recombinant human or mouse 9cRDH activity. In this regard, human and mouse RDH differ markedly from other members of the SCAD family that catalyze oxidation of all-trans-retinol (10, 11, and 18).

In order to understand whether natural retinoids can act as regulators of human and mouse 9cRDH activity, next examined was whether the different retinoic acid isomers are able to act as modulators of human and/or mouse 9cRDH activity. These findings are summarized in FIG. 9. As can be seen from FIG. 9, the all-trans-, 13-cis- and 9-cis-isomers of retinoic acid proved to be very potent inhibitors of both human and mouse 9cRDH activity whereas all-trans-retinol, oleic and palmitic acids, and oleyl and petrosenlinyl alcohols were only very weak inhibitors of this enzyme. By far, the most potent inhibitor proved to be 13-cis-retinoic acid. Approximately 50% of 9cRDH activity ($ID_{50}$) was abolished when 13-cis-retinoic acid was included in the assay mixture at concentrations of 0.15 μM, a concentration that is less than 2% of that of the 9-cis-retinol substrate concentration (10 μM). Although both 9-cis-retinoic acid ($ID_{50}$=2.6 μM) and all-trans-retinoic acid ($ID_{50}$=4.6 μM) inhibited strongly 9cRDH activity, these inhibitory effects were observed at concentrations that are an order of magnitude greater than for 13-cis-retinoic acid.

Because of the large differences in the extent of inhibition observed for 13-cis-, 9-cis-, and all-trans-retinoic acid, it seemed possible that the inhibition by the 9-cis-(18-times less potent than 13-cis-retinoic acid) and all-trans-isomers (30-times less potent than 13-cis-retinoic acid) could arise from isomerization to 13-cis-retinoic acid during incubation of the assay. To test this possibility, the degree of isomerization of retinoic acid which occurs under the assay conditions was measured. At a concentration of 10 μM retinoic acid (a concentration that results in 66 and 81% inhibition of 9cRDH activity for all-trans-, and 9-cis-retinoic acid, respectively), approximately 1% of all-trans-retinoic acid and 1.1% of 9-cis-retinoic acid isomerize to 13-cis-retinoic acid. This would translate to a final concentration (at the end of the 15 minute assay) of approximately 0.1 μM 13-cis-retinoic acid. This concentration of 13-cis-retinoic acid would be expected to inhibit approximately 40–50% of h9cRDH activity if the 13-cis-retinoic acid were present in the assay for the full 15 minute incubation. It is likely that the isomerization of all-trans- and 9-cis-retinoic acid occurs over the entire 15 minute incubation period. Hence, the 0.1 μM 13-cis-retinoic acid concentration arising from isomerization of the all-trans- and 9-cis-isomers could account for some of the inhibitory actions observed for the all-trans- and 9-cis-retinoic acid isomers. Nevertheless, isomerization to 13-cis-retinoic acid would not seem to account fully for the inhibitory properties of all-trans- or 9-cis-retinoic acid.

To gain further insights into the chemical properties responsible for 13-cis-retinoic acid inhibition of 9cRDH activity, the potential inhibitory properties of a variety of chemicals which share structural similarities with retinoic acid were tested. Among several compounds tested, only oleic acid, which has one cis double bond and a carboxylic acid group, weakly inhibited 9cRDH enzyme activity. Palmitic acid, which lacks the cis double bond, was not an inhibitor, nor were several fatty alcohols including petroselinyl alcohol and oleyl alcohol. Finally, all-trans-retinol also did not inhibit 9cRDH activity.

Biswas and Russell (32) have reported that rat liver all-trans-retinol dehydrogenase type I also uses several 3α-hydroxy- and 17β-hydroxysteroids as substrates. Chai et al. (18) also reported that hydroxysteroids are substrates for mouse liver cis-retinol dehydrogenase. Since human 9cRDH is approximately 50% identical to the rat liver enzymes and shares approximately 63% homology to mouse liver cis-retinol dehydrogenase, next investigated was whether these steroids might also be substrates for 9cRDH. To test this possibility it was determined whether human or mouse 9cRDH would catalyze oxidation of 5α-androstan-3α, 17β-diol, androsterone, testosterone or dihydrotestosterone to corresponding ketone products. Also investigated was whether human and/or mouse 9cRDH could catalyze reduction of the corresponding ketones. Neither human nor mouse 9cRDH were found to catalyze these reactions (data not shown). It is estimate, based on the lower limits for hydroxysteroid detection by TLC, that it would be possible to detect rates of hydroxysteroid oxidation as low as approximately 3 pmol/min/mg protein. This rate of hydroxysteroid oxidation is at least 2-orders of magnitude lower than Vmax values reported by Biswas and Russell (32) and Chai et al. (18) for oxidation of hydroxysteroids in their studies of enzymes that are able to oxidize both retinol and hydroxysteroids.

To gain additional insight into the possibility that human or mouse 9cRDH might possibly have some hydroxysteroid dehydrogenase activity, also tested was whether a relatively large number of 3α-hydroxy-, 11β-hydroxy- and 17β-hydroxysteroids (a larger number of hydroxysteroids than were tested as potential substrates) are able to inhibit either human and mouse 9cRDH activity. It was reasoned that if a hydroxysteroid was found to be inhibitory then this would suggest that the steroid may be a substrate for 9cRDH and worthy of further investigation. Hence, we asked whether androsterone, testosterone, estrone, β-estradiol, 4-androstene-3,17dione, 5α-androstane-3,17dione, 5α-androstane-3α, 17βdiol, 5α-androstane-3β, 17βdiol, or 5α-androstan-17βol-3one, cortisone, corticosterone, hydrocortisone, prednisone and progesterone can inhibit 9cRDH activity was investigated. For hydroxysteroid concentrations that were equimolar to the substrate concentration (10 µM), none of these hydroxysteroids inhibited either human or mouse 9cRDH activity when assayed in either the forward (retinol oxidation) or reverse (retinaldehyde reduction) directions.

Figure 10:
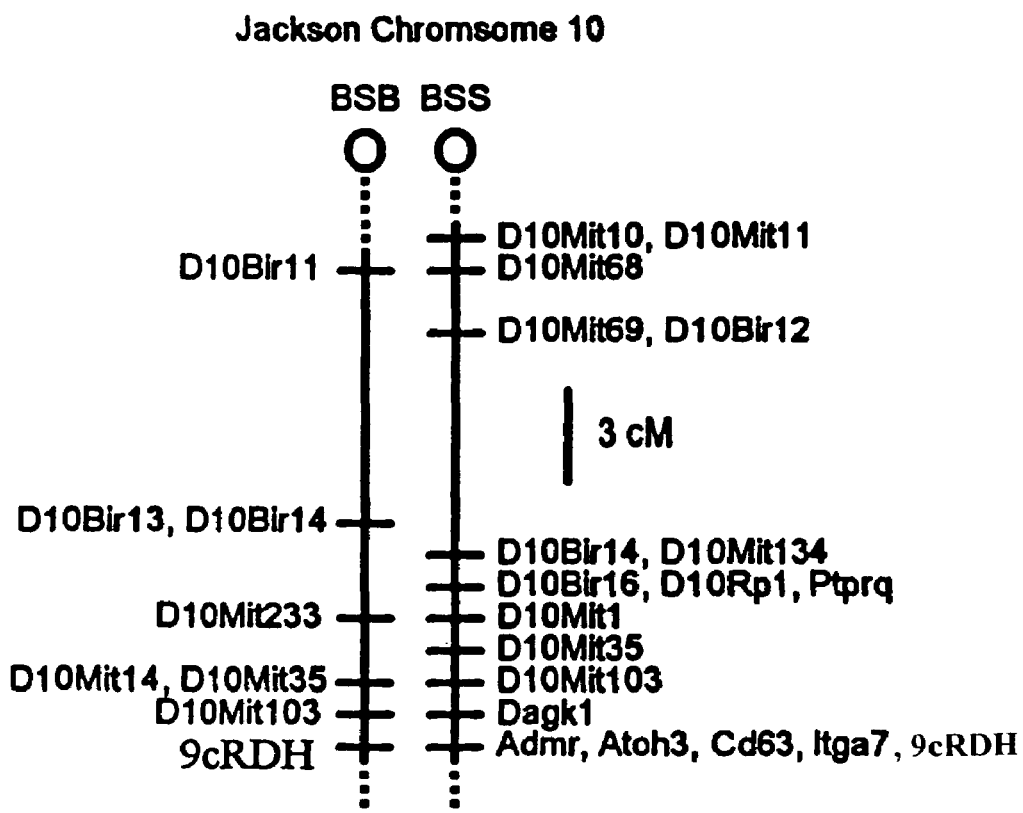

Chromosome mapping of the murine 9cRDH. To characterize more definitively the relationship of the mouse and human 9cRDHs to other retinol dehydrogenases and SCADs, the chromosomal location of 9cRDH in the mouse genome was mapped. The Jackson Laboratory interspecific backcross panels (C57BL/6J×M. spretus)F1×C57BL/6J (BSB) and (C57BL/6JEi×SPRET/Ei)F1×SPRET/Ei (BSS) were used to map the 9cRDH gene to its location on a mouse chromosome. To use these backcross panels, it is first necessary to find a polymorphism in 9cRDH between the two mouse species. For each backcross animal, some regions of its chromosomes are homozygous and some regions are heterozygous in a different pattern. If 9cRDH is located in the homozygous region, one band is produced; if it is located in a heterozygous region, two bands result. In order to use this approach, a PCR fragment length polymorphism search was first undertaken. As the exons are conserved, PCR primers were selected from the exons for this PCR screen. A polymorphism in the length of intron 4 between the mouse species C57BL/6J and M. spretus was observed. 188 animals were examined in order to identify with greater than 1 cM accuracy the chromosomal location of the 9cRDH gene. The data accumulated from the BSS and BSB panels indicated that the 9cRDH gene is located on the most distal region of mouse chromosome 10 (FIG. 10). This region is syntenic with human chromosome 12q, the region to which the human 11-cis retinol dehydrogenase (11cRDH) has been mapped previously (33).

DISCUSSION

It is generally accepted that 9-cis-retinoic acid is an important retinoid needed for regulating the actions of members of the RXR family of retinoid nuclear receptors (4, 5). There is only limited information available regarding how 9-cis-retinoic acid is formed and how it is oxidatively and/or conjugatively metabolized (6). Three possible pathways for 9-cis-retinoic acid formation have been proposed in the literature (6, 19, and 34–36). It is clear that 9-cis-retinoic acid can be formed through isomerization of all-trans-retinoic acid (6, 34, and 35). Reports demonstrating the involvement of thiol groups present in heat inactivated rat liver membranes in this isomerization (34) and demonstrating the ability of free sulfhydryl compounds to bring about isomerization (35) suggest that this process occurs without involvement of specific enzymes. Cleavage of. 9-cis-β-carotene, a carotenoid that is present in foods, has been proposed as a second pathway resulting in 9-cis-retinoic acid formation (36). This, however, cannot be an essential pathway for 9-cis-retinoic acid formation since animals maintained on a carotenoid-free diet are normal. Additionally, 9-cis-retinoic acid can be synthesized through oxidation of 9-cis-retinol to 9-cis-retinaldehyde followed by its oxidation to 9-cis-retinoic acid (19, 23). Several short and medium chain alcohol dehydrogenases able to catalyze 9-cis-retinol oxidation, and several aldehyde dehydrogenases able to catalyze 9-cis-retinaldehyde oxidation have been identified (6, 18, 19, and 23). Furthermore, 9-cis-retinol has been found in tissues where these enzymes are present (37). The cloning and characterization of a $NAD^+$-requiring human enzyme, 9cRDH, which catalyzes 9-cis- but not all-trans-retinol oxidation has been reported previously (19). The data presented in this report extend the investigations of 9cRDH actions in 9-cis-retinoic acid formation by providing information about the biochemical properties of human and mouse 9cRDH, about the tissue distribution of human and mouse 9cRDH and about the organization and location of the mouse 9cRDH gene.

These studies indicate that human and mouse 9cRDH have strikingly similar biochemical properties. The cDNA for mouse 9cRDH shares 85.5% homology with the human 9cRDH cDNA. At the amino acid level, mouse and human 9cRDH are 87.1% identical. Both human and mouse 9cRDH will catalyze the $NAD^+$-dependent oxidations of 9-cis-, 11-cis- and 13-cis-retinol and the NADH-dependent reductions of 9-cis-, 11-cis- and 13-cis-retinaldehyde (see Table VII). $NADP^+$ and NADPH can substitute for the unphosphorylated cofactors but these will only support 10% or less of the maximal reaction velocities observed for $NAD^+$ or NADH. Neither human nor mouse 9cRDH will catalyze significant oxidation of all-trans-retinol or reduction of all-trans-retinaldehyde. Human and mouse 9cRDH are not inhibited by ethanol or zinc chelators (data not shown) and both human and mouse 9cRDH are potently inhibited by 13-cis-retinoic acid, at concentrations as low as 0.05 µM, and by 9-cis- and all-trans-retinoic acid at concentrations in the 1 to 5 µM range but not significantly by fatty acids or fatty alcohols. Similarly, human and mouse 9cRDH do not appear to catalyze hydroxysteroid oxidation/reduction and are not inhibited by a large number of hydroxysteroids. Based on these very similar biochemical characteristics, it is believed that the mouse cDNA described above encodes a protein that is truly the mouse homolog of the human 9cRDH. Moreover, the catalytic properties of 9cRDH seem to be remarkably conserved across these two species, suggesting a highly defined physiologic role for the enzyme.

Figure 9A:
FIG. 9. Effects of all-trans-retinoic acid, 13-cis-retinoic acid, 9-cis-retinoic acid, all-trans-retinol, oleic acid, palmitic acid, oleyl alcohol and petroselinyl alcohol on human (FIG. 9A) and mouse (FIG. 9B) 9-cis-RDH activity. Assays were carried out for 15 minutes at 37° C. using 50 µg CHO cell homogenate protein per assay at a concentration of 9-cis-retinol substrate of 10 µM.
Figure 9B:
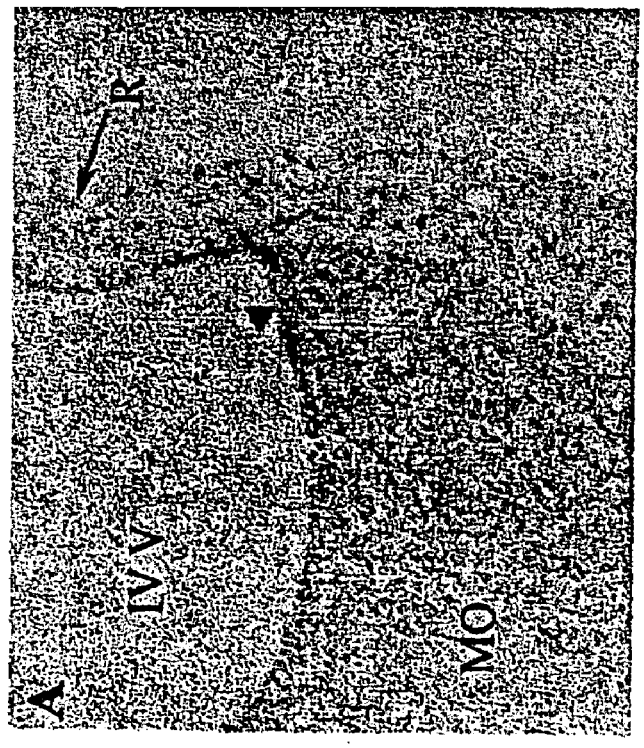

Both human and mouse 9cRDH share a great sensitivity to inhibition by 13-cis-retinoic acid (see FIG. 9). Both all-trans- and 9-cis-retinoic acid are at least one order of magnitude less potent inhibitors of 9cRDH activity. Approximately 50% of human 9cRDH activity is inhibited at 13-cis-retinoic acid concentrations around 0.1 µM. This is a concentration which is only 5- to 10-times greater than the normal physiologic concentrations of 13-cis-retinoic acid reported for rat and mouse tissues (38, 39). It is possible, considering the less than one order of magnitude difference in the concentrations of 13-cis-retinoic acid needed to inhibit 9cRDH and those that are present physiologically in blood and tissues, that fluxes in 13-cis-retinoic acid concentration could play a direct role in regulating 9cRDH activity under normal physiologic conditions. Since the concentrations of 13-cis-retinoic acid reached in the blood and tissues of both animals and humans receiving 13-cis-retinoic acid pharmacologically can reach 10 µM or greater (38, 39), it is probable that 9cRDH inhibition will be observed upon pharmacological use of 13-cis-retinoic acid. Considering that 9cRDH is expressed in the first trimester human fetus (at least by week 8), inhibition of embryonic 9cRDH upon pharmacological administration of 13-cis-retinoic acid might represent one of the many biochemical actions which give rise to the known teratogenic effects of 13-cis-retinoic acid in humans (38–40).

In addition to its actions on 9cRDH activity, the literature indicates that 13-cis-retinoic acid can act as an inhibitor of several enzymes proposed to be important for retinol and hydroxysteroid oxidation. It is well established that both all-trans- and 13-cis-retinoic acid administration to frogs can act in vivo to block the visual cycle through a mechanism proposed to involve the 11-cis-retinol dehydrogenase (11CRDH) known to be present in the RPE (41). Biswas and Russell have demonstrated that 13-cis-retinoic acid can inhibit the activity of rat liver and human prostate 17β-hydroxysteroid dehydrogenase (which is identical to retinol dehydrogenase, type I) in vitro (32). Interestingly, 9-cis-retinoic acid is an even more potent inhibitor of this enzyme than the 13-cis-isomer ($K_i$ for 13-cis-retinoic acid of 4 μM compared to a $K_i$ of 0.4 μM for 9-cis-retinoic acid) (32). Recently, Pares and colleagues have demonstrated in vitro inhibition by 13-cis-retinoic acid of purified human alcohol dehydrogenase type IV, an enzyme which has retinol dehydrogenase activity (42). However, for all of these studies, the concentration of 13-cis-retinoic acid needed to bring about significant inhibition of retinol oxidation was in the μM range. The inhibitory potency of 13-cis-retinoic acid for both human and mouse 9cRDH is at least an order of magnitude lower than that needed to bring about significant inhibition of these other enzymes. Taken together though, these data are consistent with the hypothesis that 13-cis-retinoic acid may act as a regulator of enzymes that catalyze formation of physiologically active retinoids and steroids.

Although the biochemical properties of human and mouse 9cRDH are very similar, the tissue distribution of 9cRDH in the mouse is not identical to that of the human enzyme. One very striking difference between 9cRDH mRNA expression in the human and the mouse can be seen with mammary tissue (see FIG. 7). Mouse mammary tissue is essentially devoid of 9cRDH mRNA (FIG. 7). This is unlike the human situation where mammary tissue is the tissue site where 9cRDH is most highly expressed (19). Another striking difference in this pattern is seen for the testis. In the human, the testis shows a level of expression for 9cRDH mRNA that is exceeded by only mammary tissue and kidney (19). However, as assessed by Northern blot (FIG. 7), the mouse testis either does not express detectable 9cRDH mRNA or expresses an alternatively spliced species. It seems probable, considering the findings described above in the Results section regarding identification of alternatively processed 9cRDH cDNAs in testis cDNA libraries, that mouse testis does express 9cRDH mRNA, but as an alternatively spliced form. The human heart, lung and placenta all express 9cRDH mRNA, albeit at relatively low levels, whereas no expression of mouse 9cRDH mRNA can be detected in these tissues by Northern analysis. Thus, it would seem that 9cRDH is more broadly and/or more highly expressed in the human than in the mouse. This would suggest that there may be differences across species in how tissues synthesize/obtain 9-cis-retinoic acid. Although it would be expected that these differences would have only a minor impact on whole body retinoid metabolism, these may be of significance for understanding known species differences in the levels of different retinoic acid isomers and their metabolites present in tissues and blood (43, 44).

The data and the data of others raise an important question regarding 9cRDH and its identity (19, 23, 24, and 33). 9cRDH activity was first identified through expression and enzymatic assay of a cDNA clone obtained from a human mammary tissue cDNA library (19). Two decades ago, Bonting and colleagues identified an enzyme, 11cRDH, in the bovine retinal pigment epithelium which catalyzed the formation of the visual pigment 11-cis-retinaldehyde from 11-cis-retinol (45). Later reports by other investigators concerning this ocular enzyme indicated that the bovine enzyme will not catalyze 9-cis-retinol oxidation (46). In 1995, two groups reported the independent cloning of the cDNA for bovine 11cRDH. (15, 16). Both indicated that 11cRDH mRNA could be detected only in the retinal pigment epithelium (15, 16) and one group added that a monoclonal antibody against bovine 11cRDH did not recognize proteins present in extraocular tissues like the liver and kidney (16) (two sites of 9cRDH expression in the mouse and human (19)). With the publication of the description of the genomic clone for human 11cRDH (33), it seemed likely that human 11cRDH and human 9cRDH were very similar, if not identical. The amino acid sequences predicted by the human 11cRDH genomic clone differed in only one amino acid from that predicted by the human mammary 9cRDH cDNA (19, 33). Alternatively, it was also possible that the gene described as human 11cRDH was actually that of human 9cRDH since no measures of the enzymatic activity of the expressed cDNA clone for this gene were reported (33). The group reporting the genomic clone for human 11cRDH (and the earlier cloning of a bovine 11cRDH cDNA (15)) is the same group that recently described the cloning of mouse 9cRDH in Romert et al. (22). In the text of Romert et al. (22), these investigators express the believe that their 9cRDH is distinct from 11cRDH. The recent report of Driessen et al. (23), another group that reported cloning a cDNA for bovine 11cRDH (16), indicates that these investigators believe that 9cRDH and 11cRDH are the same enzyme, and that the earlier eye literature had been incomplete in its characterization of the tissue distribution and substrate specificities of 11cRDH (15, 16, 33, 45, 46). Although the present studies have not worked with ocular tissue, nor with recombinant preparations acknowledged to have 11cRDH activity, based on the cDNA cloning data therein, the biochemical properties of human and mouse 9cRDH and the genomic structure of the 9cRDH gene (see below), the view put forth by Driessen et al. (23) that 9cRDH and 11cRDH are indeed the same protein is supported.

The mouse gene for 9cRDH was mapped to the most distal region of mouse chromosome 10 (FIG. 10). This region of mouse chromosome 10 was also recently proposed to be the site of the mouse 11cRDH gene by Driessen et al. (23). Although these investigators reported the chromosomal location of 11cRDH, they have published only limited information characterizing this gene. Specifically, Driessen et al. (23) have indicated that the gene is composed of 5 exons and they have provided some information about the approximate sizes of each exon. In addition, Driessen et al. (23) reported that the gene is probably a single copy gene. Based on this information from the literature and the data here on the structure and location of the mouse 9cRDH gene, it would appear that the same gene as Driessen et al. has been cloned here (23). This too is consistent with the conclusion reached above that 9cRDH and 11cRDH are the same enzyme and moreover, this adds much weight to this conclusion.

In summary, characterized here is the tissue distribution of 9cRDH in adult and fetal mouse and fetal human tissues along with some of the biochemical properties of human and mouse 9cRDH. In addition, reported is on the gene structure for mouse 9cRDH. The demonstration of 9cRDH expression in first trimester human embryos and at mid-gestation in mouse embryos coupled with the observation that 13-cis-retinoic acid is a specific and highly potent inhibitor of 9cRDH activity raises the possibility that one biochemical basis for the toxic actions of 13-cis-retinoic acid may arise from its effect on 9cRDH activity. It is clear from these studies that human and mouse 9cRDH both will utilize 9-cis-retinol but not all-trans-retinol or a number of 3α-hydroxy-, 11α-hydroxy- or 17β-hydroxysteroids or fatty alcohols as substrates. Overall, these findings along with literature reports of the presence of 9-cis-retinol in some tissues that express 9cRDH (37) are consistent with the earlier suggestion (19) that 9cRDH plays a physiologic role in the formation of 9-cis-retinoic acid. Nevertheless, the physiologic importance of 9cRDH in a 9-cis-retinol utilizing metabolic pathway for generating 9-cis-retinoic acid will require further investigation to establish conclusively.

REFERENCES FOR THE THIRD SERIES OF EXPERIMENTS

1. Goodman, D. S. (1984) *N. Eng. J. Med* 310, 1023–1031
2. Saari, J. C. (1994) in *The Retinoids: Biology, Chemistry and Medicine* (Sporn, M. B., Roberts, A. B., and Goodman, D. S. eds) Raven Press, Ltd. New York
3. Hofmann, C. and Eichele, G. (1994) in *The Retinoids, Biology, Chemistry, and Medicine* (Sporn, M. B., Roberts, A. B., and Goodman, D. S. eds) pp. 387–442, Raven Press, New York
4. Mangelsdorf, D. M., Umesono, K., and Evans, R. M. (1994) in *The Retinoids: Biology, Chemistry, and Medicine* (Sporn, M. B., Roberts, A. B., and Goodman, D. S. eds) pp. 319–350, Raven Press, New York
5. Gudas, L. J., Sporn, M. B., and Roberts, A. B. (1994) in *The Retinoids: Biology, Chemistry, and Medicine* (Sporn, M. B., Roberts, A. B., and Goodman, D. S. eds) pp. 443–520, Raven Press, Ltd., New York
6. Blaner, W. S. and Olson, J. A. (1994) in *The Retinoids: Biology, Chemistry, and Medicine* (Sporn, M. B., Roberts, A. B., and Goodman, D. S. eds) pp. 229–255, Raven Press, Ltd. New York
7. Duester, G. (1996) *Biochemistry* 35, 12221–12227
8. Ang, H. L., Deltour, L., Hayamizu, T. F., Zgombic-Knight, M., and Duester, G. (1996) *J. Biol. Chem.* 271, 9526–9534
9. Ang, H. L., Deltour., L., Zgombic-Knight, M., Wagner, M. A., and Duester, G. (1996) *Alcohol. Clin. Exp. Res.* 20, 1050–1064
10. Boerman, M. H. E. M. and Napoli, J. L. (1995) *Arch. Biochem. Biophys.* 321, 434–441
11. Boerman, M. H. E. M. and Napoli, J. L. (1995) *Biochemistry* 34, 7027–7037
12. Chai, X. and Napoli, J. L. (1996) *Gene* 169, 219–222
13. Chai, X., Boerman, M. H. E. M., Zhai, Y., and Napoli, J. L. (1995) *J. Biol. Chem.* 270, 3900–3904
14. Chai, X., Zhai, Y., Popescu, G., and Napoli, J. L. (1995) *J. Biol. Chem.* 270, 28408–28412
15. Simon, A., Hellman, U., Wernstedt, C., and Eriksson, U. (1995) *J. Biol. Chem.* 270, 1107–1112
16. Driessen, C. A., Janssen, B. P., Winkens, H. J., van Vugt, A. H., de Leeuw, T. L., and Janssen, J. J. (1995) *Invest. Ophthalmol. Vis. Sci.* 36, 1988–1996
17. Boerman, M. H. E. M. and Napoli, J. L. (1996) *J. Biol. Chem.* 271, 5610–5616
18. Chai, X., Zhai, Y., and Napoli, J. L. (1997) *J. Biol. Chem.* 272, 33125–33131
19. Mertz, J. R., Shang, E., Piantedosi, R., Wei, S., Wolgemuth, D. J., and Blaner, W. S. (1997) *J. Biol. Chem.* 272, 11744–11749
20. Tsigelny, I. And Baker, M. E. (1996) *Biochem. Biophys. Res. Comm.* 226, 118–127
21. Baker, M. E. (1995) *BioEssays* 18, 63–70.
22. Romert, A., Tuvendal, P., Simon, A., Dencker, L. and Eriksson, U. (1998) *Proc. Natl. Acad. Sci. USA* 95, 4404–4409
23. Driessen, C. A. G. G., Winkens, H. J., Kuhlmann, E. D., Janssen, A. P. M., van Vugt, A. H. M., Deutman, A. F. and Janssen, J. J. M. (1998) *FEBS Lett.* 428, 135–140
24. Blaner, W. S., Das, S. R., Gouras, P., and Flood, M. D. (1987) *J. Biol. Chem.* 262, 53–58
25. Furr, H. C., Barua, A. B., and Olson, J. A. (1994) in *The Retinoids, Biology, Chemistry, and Medicine* (Sporn, M. B., Roberts, A. B., and Goodman, D. S. eds) pp. 179–210, Raven Press, New York
26. Mertz, J. R., Banda, P. W. and Kierszenbaum, A. L. (1995) *Mol. Reprod. Dev.* 41, 374–383
27. Rhee, K., and Wolgemuth, D. J. (1997) *Development* 124, 2167–2177
28. Maniatis, T., Fritsch, E. F., and Sambrook, J. (1982) *Molecular Cloning: A Laboratory Manual*, 2nd Ed., Cold Spring Harbor Laboratory, Cold Spring Harbor, N.Y.
29. Chomczynski, P. and Sacchi, N. (1987) *Anal. Biochem.* 162, 156–159
30. Besset, V., Rhee, K. and Wolgemuth D. J. (1998) *Mol. Reprod. Devel.*, in press.
31. Chapman, D. L. and Wolgemuth, D. J. (1992) *Mol. Reprod. Devel.* 33, 259–269
32. Biswas, M. G. and Russell, D. W. (1997) *J. Biol. Chem.* 272, 15959–15966
33. Simon, A., Lagercrantz, J., Bajalica-Lagercrantz, S. and Eriksson, U. (1996) *Genomics* 36, 424–430 Urbach and Rando, (1994) *Biochem. J.* 299, 459–465
35. Shih, T. W., Lin, T. H., Shealy, Y. F. and Hill D. L. (1997) *Drug Metab. Dispos.* 25, 27–32
36. Wang, X-D., Krinsky, N. I., Benotti, P. N. and Russell, R. M. (1994) *Arch. Biochem. Biophys.* 313, 150–155
37. Ben-Amotz, A., Mokady, S. and Avron, M. (1988) Br. *J. Nutr.* 59, 443–449
38. Sass, J. O., Masgrau, E., Saurat, J-H. and Nau, H. (1995) *Drug Metab. Dispos.* 23, 887–891
39. Collins, M. D., Tzimas, G., Hummler, H., Burgen, H. and Nau, H. (1992) *Toxicol. Appl. Pharmacol.* 127, 132–144
40. Soprano, D. R. and Soprano, K. J. (1995) *Ann. Rev. Nutr.* 15, 111–132
41. Law, W. C. and Rando, R. R. (1989) *Biochem. Biophys. Res. Comm.* 161, 825–829
42. Allali-Hassani, A., Perabla, J. M., Martras, S., Farres, J., Pares, X. (1998) *FEBS Letters* 426, 362–366
43. Tzimas, G., Sass, J. O., Wittfoht, W., Elmazar, M. M. A., Ehlers, K. and Nau, H. (1994) *Drug Meabol. Dispos.* 22, 928–936
44. Marchetti, M-N., Sampol, E., Bun, H., Scoma, H., Lacareue, B. and Durand, A. (1997) *Drug Metabol. Dispos.* 25, 637–646
45. Lion, F., Rotmans, J. P., Daemen, F. J. M., and Bonting, S. L. (1975) *Biochim. Biophys. Acta* 384, 283–293.
46. Suzuki, Y., Ishiguro, S-I., and Tamai, M. (1993) *Biochim. Biophys. Acta* 1163, 201–208

What is claimed is:

1. An isolated nucleic acid molecule encoding a 9-cis-retinol dehydrogenase having the amino acid sequence of SEQ ID NO:2.

2. The isolated nucleic acid molecule of claim 1, wherein the nucleic acid molecule is a DNA molecule.

3. The isolated DNA molecule of claim 2, wherein the DNA molecule comprises consecutive nucleotides 114–1070 of the nucleotide sequence of SEQ ID NO:1.

4. The isolated DNA molecule of claim 2, wherein the DNA molecule is a cDNA molecule.

5. The isolated DNA molecule of claim 2, wherein the DNA molecule is a genomic DNA molecule.

6. The isolated nucleic acid molecule of claim 1, wherein the nucleic acid molecule is an RNA molecule.

7. A composition comprising an isolated nucleic acid molecule encoding a 9-cis-retinol dehydrogenase having the amino acid sequence of SEQ ID NO:2 and a promoter of RNA transcription operatively linked to said nucleic acid molecule.

8. A vector comprising the isolated nucleic acid molecule of claim 1.

9. A vector of claim 8, wherein the vector is a plasmid.

10. The plasmid of claim 9 designated pCDNA3-1 (ATCC Accession No. 209285).

11. An isolated host cell transfected with the plasmid of claim 10.

12. The host cell of claim 11, wherein the cell is selected from a group consisting of a bacterial cell, a plant cell, an insect cell and a mammalian cell.

13. A method of producing a polypeptide having 9-cis-retinol dehydrogenase activity; which comprises growing host cells of claim 12 to produce the polypeptide and recovering the polypeptide produced.

* * * * *